(12) United States Patent
Gouailhardou et al.

(10) Patent No.: US 12,251,563 B2
(45) Date of Patent: *Mar. 18, 2025

(54) APPARATUS, SYSTEMS AND METHODS FOR MONITORING SYMPTOMS OF NEUROLOGICAL CONDITIONS

(71) Applicant: Neurode Pty Ltd, Dover Heights (AU)

(72) Inventors: Nathalie Gouailhardou, Dover Heights (AU); Damian Sofrevski, Dover Heights (AU)

(73) Assignee: Neurode Pty Ltd, Dover Heights (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/395,005

(22) Filed: Dec. 22, 2023

(65) Prior Publication Data
US 2024/0226551 A1   Jul. 11, 2024

Related U.S. Application Data

(63) Continuation of application No. 18/453,146, filed on Aug. 21, 2023, now Pat. No. 11,931,574, which is a
(Continued)

(30) Foreign Application Priority Data

Feb. 22, 2021   (AU) ................................ 2021900473
Dec. 23, 2021   (AU) ................................ 2021904220

(51) Int. Cl.
*A61N 1/36*   (2006.01)
*A61B 5/00*   (2006.01)
(Continued)

(52) U.S. Cl.
CPC ...... *A61N 1/36034* (2017.08); *A61B 5/14552* (2013.01); *A61B 5/6803* (2013.01);
(Continued)

(58) Field of Classification Search
CPC .................. A61N 1/36034; A61N 1/36031
(Continued)

(56) References Cited

U.S. PATENT DOCUMENTS 9,014,811 B2   4/2015   Pal et al.
9,042,201 B2   5/2015   Tyler et al.
(Continued)

FOREIGN PATENT DOCUMENTS

CN   104042228 A   9/2014
CN   111195393 A   5/2020
(Continued)

OTHER PUBLICATIONS

Cavaleiro et al., "Memory and Cognition-Related Neuroplasticity Enhancement by Transcranial Direct Current Stimulation in Rodents: A Systematic Review," Neural Plasticity, vol. 2020, 2020, 23 pages.
(Continued)

*Primary Examiner* — Nadia A Mahmood
(74) *Attorney, Agent, or Firm* — COOLEY LLP

(57) ABSTRACT

A system for controlling delivery of electrical stimulation to a subject. The system comprises a control device configured to send stimulation instructions to an electrical stimulation generator to cause the electrical stimulation generator to deliver transcranial electrical stimulation to one or more electrodes arranged to be positioned in proximity to a targeted region of the brain of the subject. The stimulation instructions comprise stimulation parameter value(s). The control device is configured to receive sensor data from optical sensor(s) arranged to be positioned in proximity to the targeted region and transmit updated stimulation instructions comprising updated simulation parameter value(s) to the electrical stimulation generator to cause the electrical stimulation generator to modify characteristic(s) of the stimulation. The system is configured to analyse the sensor
(Continued)

data to determine an activity measure and determine updated stimulation parameter value(s) based on the determined activity measure.

30 Claims, 17 Drawing Sheets

Related U.S. Application Data continuation of application No. PCT/AU2022/050136, filed on Feb. 22, 2022.

(51) Int. Cl.
 *A61B 5/1455* (2006.01)
 *A61N 1/04* (2006.01)
(52) U.S. Cl.
 CPC ......... *A61N 1/0456* (2013.01); *A61N 1/0484* (2013.01); *A61N 1/36031* (2017.08)
(58) Field of Classification Search
 USPC ........................................................ 607/59
 See application file for complete search history.

(56) References Cited

U.S. PATENT DOCUMENTS

| | | | |
|---|---|---|---|
| 9,114,274 B2 | 8/2015 | Kwon et al. |
| 9,233,244 B2 | 1/2016 | Pal et al. |
| 9,333,334 B2 | 5/2016 | Jeffery et al. |
| 9,393,401 B2 | 7/2016 | Goldwasser et al. |
| 9,393,430 B2 | 7/2016 | Demers et al. |
| 9,399,126 B2 | 7/2016 | Pal et al. |
| 9,440,070 B2 | 9/2016 | Goldwasser et al. |
| 9,474,891 B2 | 10/2016 | Demers et al. |
| 9,517,351 B2 | 12/2016 | Charlesworth et al. |
| D785,186 S | 4/2017 | Morenstein et al. |
| D787,686 S | 5/2017 | Jeffery et al. |
| 9,729,252 B2 | 8/2017 | Tyler et al. |
| 9,878,155 B1 | 1/2018 | Phillips et al. |
| 9,956,405 B2 | 5/2018 | Goldwasser et al. |
| 9,968,780 B2 | 5/2018 | Pal et al. |
| 10,046,162 B1 | 8/2018 | Pilly et al. |
| 10,071,245 B1 | 9/2018 | Phillips et al. |
| 10,092,753 B1 | 10/2018 | Howard et al. |
| 10,238,870 B2 | 3/2019 | Pilly et al. |
| 10,293,161 B2 | 5/2019 | Charlesworth et al. |
| 10,307,592 B1 | 6/2019 | Pilly et al. |
| 10,357,654 B1 | 7/2019 | Pilly et al. |
| 10,376,697 B2 | 8/2019 | Ziegler et al. |
| 10,396,905 B2 | 8/2019 | Tyler et al. |
| 10,413,724 B2 | 9/2019 | Choe et al. |
| 10,413,757 B2 | 9/2019 | Sato et al. |
| 10,420,937 B2 | 9/2019 | Pilly et al. |
| 10,426,945 B2 | 10/2019 | Tyler et al. |
| 10,485,972 B2 | 11/2019 | Pal et al. |
| 10,537,703 B2 | 1/2020 | Tyler et al. |
| 10,596,372 B2 | 3/2020 | Howard et al. |
| 10,646,708 B2 | 5/2020 | Goldwasser et al. |
| 10,716,514 B1 | 7/2020 | Ketz et al. |
| 10,720,076 B1 | 7/2020 | Pilly et al. |
| 10,736,561 B2 | 8/2020 | Howard et al. |
| 10,744,321 B2 | 8/2020 | Pilly et al. |
| 10,796,596 B2 | 10/2020 | Skorheim et al. |
| 10,814,131 B2 | 10/2020 | Goldwasser et al. |
| 10,835,176 B2 | 11/2020 | Mohammadrezazade et al. |
| 10,850,099 B2 | 12/2020 | Skorheim et al. |
| 10,918,862 B1 | 2/2021 | Choe et al. |
| 11,052,252 B1 | 7/2021 | Howard et al. |
| 11,207,489 B2 | 12/2021 | Patel et al. |
| 11,235,148 B2 | 2/2022 | Charlesworth et al. |
| 11,278,722 B2 | 3/2022 | Howard et al. |
| 11,278,724 B2 | 3/2022 | Law et al. |
| 11,285,319 B1 | 3/2022 | Hubbard et al. |
| 11,285,320 B1 | 3/2022 | Choe et al. |
| 11,288,977 B1 | 3/2022 | Howard et al. |
| 11,331,483 B1 | 5/2022 | Ziegler et al. |
| 11,338,136 B2 | 5/2022 | Jeong et al. |
| 11,344,723 B1 | 5/2022 | Roach et al. |
| 11,534,608 B2 | 12/2022 | Tyler et al. |
| 11,931,574 B2 | 3/2024 | Gouailhardou et al. |
| 2013/0225953 A1 | 8/2013 | Oliviero et al. |
| 2015/0174418 A1 | 6/2015 | Tyler et al. |
| 2017/0197081 A1 | 7/2017 | Charlesworth et al. |
| 2017/0312518 A1 | 11/2017 | Ziegler et al. |
| 2019/0021657 A1 | 1/2019 | Mohammadrezazade et al. |
| 2019/0151654 A1 | 5/2019 | Wingeier et al. |
| 2020/0155061 A1 | 5/2020 | Pradeep |
| 2020/0289054 A1 | 9/2020 | Muvvala |
| 2021/0023369 A1 | 1/2021 | Jeong et al. |
| 2021/0113835 A1 | 4/2021 | Wingeier |
| 2024/0017064 A1 | 1/2024 | Gouailhardou et al. |

FOREIGN PATENT DOCUMENTS

| | | |
|---|---|---|
| EP | 3106202 A1 | 12/2016 |
| JP | 2010233746 A | 10/2010 |
| JP | 2010240298 A | 10/2010 |
| JP | 2012509121 A | 4/2012 |
| JP | 2016189955 A | 11/2016 |
| JP | 2017055886 A | 3/2017 |
| JP | 2018508321 A | 3/2018 |
| KR | 102100696 B1 | 4/2020 |
| KR | 102278547 B1 | 7/2021 |
| KR | 102538311 B1 | 5/2023 |
| WO | WO-2007109124 A2 | 9/2007 |
| WO | WO-2011106660 A1 | 9/2011 |
| WO | WO-2014210595 A1 | 12/2014 |
| WO | WO-2016145232 A2 | 9/2016 |
| WO | WO-2018081134 A1 | 5/2018 |
| WO | WO-2018125376 A1 | 7/2018 |
| WO | WO-2020081609 A1 | 4/2020 |
| WO | WO-2022174312 A1 | 8/2022 |

OTHER PUBLICATIONS

Chhatbar et al., "Evidence of transcranial direct current stimulation-generated electric fields at subthalamic level in human brain in vivo," Brain Stimulation, vol. 11, Issue 4, Jul.-Aug. 2018, pp. 727-733.
Cocco et al., "Plasma BDNF Levels Following Transcranial Direct Current Stimulation Allow Prediction of Synaptic Plasticity and Memory Deficits in 3xTg-AD Mice," Front. Cell Dev. Biol., vol. 8, Jul. 3, 2020, 12 pages.
Islam et al., "Increase in the calcium level following anodal polarization in the rat brain," Brain Research, vol. 684, Issue 2, Jul. 3, 1995, pp. 206-208.
Kuo et al., "Effects of transcranial electrical stimulation on cognition," Clinical EEG and Neuroscience, 43(3), 2012, pp. 192-199.
Liebetanz et al., "Pharmacological approach to the mechanics of transcranial DC-stimulation-induced after-effects of human motor cortex excitability," Brain, vol. 125, 2002, pp. 2238-2247.
Molavi et al., "Wavelet-based motion artifact removal for functional near-infrared spectroscopy," Physiol. Meas., vol. 33, No. 2, Jan. 25, 2012, p. 259.
Non-Final Office Action for U.S. Appl. No. 18/453,146, dated Nov. 3, 2023, 8 pages.
Polania et al., "Modulating functional connectivity patterns and topological functional organization of the human brain with transcranial direct current stimulation," Hum Brain Mapp., 32(8), Aug. 2011 (Epub Jul. 6, 2010), pp. 1236-1249.
Scholkamm et al., "How to detect and reduce movement artifacts in near-infrared imaging using moving standard deviation and spline interpolation," Physiol. Meas., vol. 31, No. 5, May 2010, pp. 649-662.
Shatz, "The Developing Brain," Scientific American, vol. 267, No. 3, Sep. 1992, pp. 60-67.
Voroslakos et al., "Direct effects of transcranial electric stimulation on brain circuits in rats and humans," Nature Communications, vol. 9, Article No. 483, Feb. 2, 2018, 17 pages.

(56) References Cited

OTHER PUBLICATIONS

Extended European Search Report for European Application No. 22755421.9, dated Dec. 12, 2024, 7 pages.

800

Send stimulation instruction to an electrical stimulation generator to cause the electrical stimulation generator to deliver transcranial electrical stimulation to one or more electrodes arranged to be positioned on the head of the subject
805

Receive recorded data from one or more sensors arranged to be positioned in proximity to the targeted region 810

Analyse the response data to determine an effectiveness/activity measure
815

Modify the stimulation instructions based on the determined effectiveness/ activity measure
820

Transmit updated stimulation instructions to the electrical generator to cause the electrical generator to modify one or more characteristics of the stimulation
825

Fig. 8

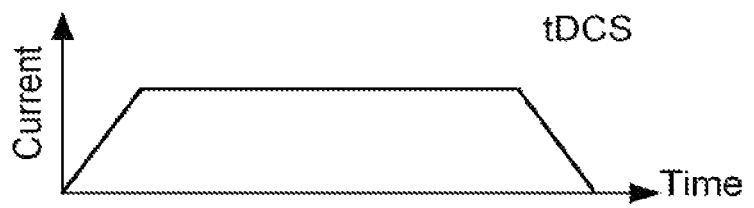
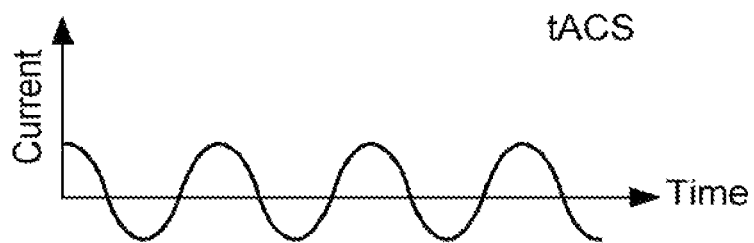
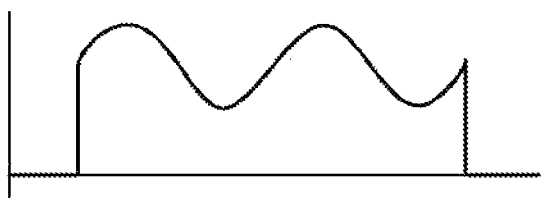
Fig. 9A

APPARATUS, SYSTEMS AND METHODS FOR MONITORING SYMPTOMS OF NEUROLOGICAL CONDITIONS

CROSS-REFERENCE TO RELATED APPLICATIONS

This application is a continuation of U.S. patent application Ser. No. 18/453,146, filed Aug. 21, 2023, which is a continuation of International Application No. PCT/AU2022/050136, filed Feb. 22, 2022, which claims the benefit of Australia Application No. 2021900473, filed Feb. 22, 2021, and Australia Application No. 2021904220 filed Dec. 23, 2021, the disclosure of each of which are hereby incorporated by reference in their entireties.

TECHNICAL FIELD

Embodiments generally relate to methods, apparatus and systems for monitoring, and in some embodiments, treatment of symptoms of neurological conditions in subjects, and in particular, symptoms of neurobehavioural disorders, such as attention deficit hyperactivity disorder (ADHD).

BACKGROUND

Subjects with ADHD tend to exhibit symptoms such as difficulty paying attention, controlling impulsive behaviours and/or may be overly or hyperactive. There are three main types of ADHD: predominantly inattentive presentation, where the subject has difficulty in following instructions and paying attention, is easily distracted and disorganised; predominantly hyperactive-impulsive presentation, where the subject fidgets, is restless, and impulsive; and combined presentation, where the subject exhibits symptoms of both types.

Techniques for assessing ADHD symptoms include psychometric tests measuring executive function performance such as testing working memory, attention, and impulse control, and ADHD symptoms may manifest as reduced performance in these tests.

Electrical brain stimulation is known to have prominent effects on cognitive processes, with various different effects depending on the type of stimulation applied. According to Min-Fang Kuo and Michael A. Nitsche, 'Effects of transcranial electrical stimulation on cognition' (2012) 43(3) Clinical EEG and Neuroscience 192-199, (the entire content of which is incorporated herein by reference), non-invasive electrical brain stimulation techniques may amplify the neurophysiological processes required during cognition and/or may mimic the physiological process of cognition, and further, that different types of stimulation may produce different responses. For example, transcranial direct current stimulation (tDCS) may induce physiological changes that resemble neuroplastic alterations of cortical function, which are thought to be key to learning and memory formation. Many studies have shown the beneficial effects of tDCS on task performance. Furthermore, Kuo and Nitsche (2012) observe that other techniques such as alternating current stimulation (tACS) and random noise stimulation (tRNS) may modulate other cortical activity depending on the frequency of the electrical stimulation.

It is desired to address or ameliorate one or more shortcomings or disadvantages associated with prior techniques for treatment of neurological conditions in subjects, such as ADHD and other neurobehavioural disorders, or at least provide a useful alternative thereto.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

Some embodiments relate to a system for controlling delivery of electrical stimulation to a subject, the system comprising: a control device configured to: send stimulation instructions to an electrical stimulation generator to cause the electrical stimulation generator to deliver transcranial electrical stimulation to one or more electrodes arranged to be positioned in proximity to a targeted region of the brain of the subject, wherein the stimulation instructions comprise at least one stimulation parameter value: receive sensor data from one or more optical sensors arranged to be positioned in proximity to the targeted region; and transmit updated stimulation instructions comprising one or more updated simulation parameter values to the electrical stimulation generator to cause the electrical stimulation generator to modify one or more characteristics of the stimulation: wherein the system is further configured to: analyse the sensor data to determine an activity measure; and determine the one or more updated stimulation parameter values based on the determined activity measure.

The sensor data may comprise pre-stimulation sensor data acquired prior to the delivery of stimulation to the one or more electrodes, during-stimulation sensor data acquired while the stimulation was being delivered to the one or more electrodes, and after-stimulation sensor data acquired after the stimulation was delivered to the one or more electrodes, and where the system is configured to: determine, from the pre-stimulation sensor data, during-stimulation sensor data and post-stimulation sensor data, respectively, pre-stimulation, during-stimulation and post stimulation values for one or more features; for each of the one or more features, determine a relative change in the value of the feature from (i) the pre-stimulation value to the post-stimulation value, (ii) the pre-stimulation value to the during-stimulation value, and iii) the during-stimulation value to the post-stimulation value: providing the relative changes in value of the one or more features and the stimulation parameter value to an activity determination model; and determine by the activity determination model, the activity measure.

The activity measure may be indicative of sufficient stimulation having been delivered to the subject.

The one or more features may comprise: functional connectivity between pairs of optical sensor channels and/or statistical measures of data acquired from optical sensor channels.

The one or more features may be extracted from sensor data acquired from pairs of optical channels around and/or between stimulating electrodes of the one or more electrodes.

The sensor data may comprise data acquired from the subject's left lateral prefrontal cortex, the subject's medial prefrontal cortex, and/or a boundary region between the subject's medial prefrontal and left lateral prefrontal The sensor data may comprise data acquired from the subject's right lateral prefrontal cortex, the subject's medial prefrontal cortex, and/or a boundary region between the subject's medial prefrontal and right lateral prefrontal.

The system being configured to determine the one or more updated stimulation parameter values based on the determined activity measure may comprise: responsive to determining that the activity measure is less than a threshold value, increasing the stimulation parameter value and reapplying the stimulation at the increased stimulation parameter value; and responsive to determining that the activity measure has reached the threshold value, determining the stimulation parameter value as a user-specific calibrated stimulation parameter.

The system may further comprise a head mountable array carrying the optical sensors, and wherein the optical sensors are functional near infrared spectroscopy sensors (fNIRS). The head mountable array may further carry the one or more electrodes.

The system may further comprise: an optical sensor module coupled to the one or more optical sensors, the optical sensor module configured to cause light to be emitted from a respective emitter of the one or more optical sensors, and to receive a signal indicative of reflected light from a respective detector of the of the one or more optical sensors, wherein the signal is indicative of cerebral haemodynamic response in relation to neural activities in the targeted region: wherein the optical sensor module is configured to provide the sensor data to the control device, the sensor data being based on the signals received from the respective one or more sensors; and wherein the optical sensor module is configured to operate in response to instructions received from the control device.

The control device may be configured to cause the optical sensor module to switch the emitter of the one or more optical sensors on and off at a relatively high frequency to create a lock-in-amplifier effect to improve the signal to noise ratio (SNR) of the respective detected reflected light signals.

Each of the one or more optical sensors may comprise an emitter and a first and second detectors and form two detector channels, and wherein the control device is configured to demodulate the signal of the detector channels of each of the optical sensors.

The sensor data from the plurality of functional channels may be down sampled.

The sensor data may comprise measured data including one or more of: (i) reflected light intensity at two distinctive wavelengths detected by the one or more sensors; (ii) oxygenated haemoglobin (HbO) concentration; (iii) deoxygenated haemoglobin (HbR) concentration; (iv) total haemoglobin (ThB) concentration; and (v) relative changes in any of measures (i) to (iv).

The control device may be configured to cause the stimulation generator to supply one or more of: (i) transcranial direct current stimulation (tDCS); (ii) transcranial alternating current stimulation (tACS); (iii) transcranial random noise stimulation (tRNS); (iv) transcranial pulse current stimulation (tPCS): (v) transcranial random noise stimulation (tRNS); and (vi) and oscillating tDCS (otDCS).

The stimulation instructions may include one or more of: (i) voltage; (ii) current; (iii) frequency; (iv) duration; and (v) offset.

The control device may be configured to cause the electrical stimulation generator to deliver a relatively short pulse of electrical stimulation to the one or more electrodes, and to cause the optical sensor module to record the reflected signals from the respective sensors after the relatively short pulse of electrical stimulation has been delivered the one or more electrodes.

The control device may be configured to cause the electrical stimulation generator to deliver a relatively long session of electrical stimulation to the one or more electrodes, and to cause the optical sensor module to record the reflected signals from the respective sensors while the electrical stimulation is being delivered to the one or more electrodes.

The control device may be configured to receive the recorded data from the one or more optical sensors before, during and/or after the delivery of the electrical stimulation to the one or more electrodes.

The control device may be configured to continually monitor the brain activity of the subject.

The control device may be configured to instigate a session in response to instructions received from a cognitive performance monitoring application deployed on computing device in communication with the control device.

The system may further comprise a computing device or server in communication with the control device across a communications network, and wherein the computing device or server is configured to: receive the sensor data from the control device; analyse the sensor data to determine the activity measure; determine the one or more updated stimulation parameter values based on the determined activity measure; and transmit the updated stimulation parameter values to the control device.

The control device may be configured to transmit the sensor data to a computing device or server for processing, and to receive the updated stimulation parameter values from the respective computing device or server.

Some embodiments relate to a system for determining stimulation parameters for controlling delivery of electrical stimulation to a subject, the system comprising: one or more processors; and memory comprising executable instructions, which when executed by the one or more processors, causes the system to: receive sensor data from the control device, the sensor data derived from one or more optical sensors positioned in proximity to a targeted region of a subject's head: analyse the sensor data to determine an activity measure; determine the one or more updated stimulation parameter values based on the determined activity measure, wherein the updated stimulation parameter values are indicative of characteristics of transcranial electrical stimulation to be delivered to the subject by an electrical stimulation generator under the control of the control device; and transmit the updated stimulation parameter values to the control device.

The system may further comprise an activity determination model configured to receive as inputs, features extracted from the sensor data and to provide as an output, the activity measure.

The control device may be configured to allow for selection of a subset of the electrodes to be used when administering stimulation to thereby tailor the control device to suit a particular subject's head size. The control device may be configured to receive a head size indication from the subject via a user interface and to determine the subset of electrodes to be used based on the head size indication. The control device may be configured to: deliver at least a first test signal to each of one or more subsets of electrodes of the array: analyse a test response detected by respective sensor modules; determine a suitable subset of electrodes for the subject based on the detected test responses; and select the suitable subset of electrodes for use in administering the stimulation to the head of the subject.

The system may further comprise a positioning feedback module configured to assist the subject in correct placement of the array relative to the subject's head. The positioning feedback module may be configured to: determine one or more images of the subject donning the array of the control device; detect a position of one or more facial features of the subject within the one or more images: detect a position of the array within the one or more images relative to the determined facial features: compare a determined position of the array to a target position; and responsive to determining that the position of the array falls within an acceptable range, determine the array to be correctly placed; and responsive to determining that the position of the array falls within an acceptable range, determine the array to be incorrectly placed, provide feedback to the subject via a user interface to assist them to reposition the array with a view to achieving the target position.

Some embodiments relate to a method for controlling delivery of electrical stimulation to a subject, the method comprising: sending stimulation instructions to an electrical stimulation generator to cause the electrical stimulation generator to deliver transcranial electrical stimulation to one or more electrodes arranged to be positioned in proximity to a targeted region of the brain of the subject, wherein the stimulation instructions comprise at least one stimulation parameter value: receiving sensor data from one or more optical sensors arranged to be positioned in proximity to the targeted region: analysing the sensor data to determine an activity measure: determining one or more updated stimulation parameter values based on the determined activity measure; and transmitting updated stimulation instructions comprising the one or more updated simulation parameter values to the electrical stimulation generator to cause the electrical stimulation generator to modify one or more characteristics of the stimulation.

Some embodiments relate to a method for determining stimulation parameters for controlling delivery of electrical stimulation to a subject, the method comprising: receiving sensor data from a control device, the sensor data derived from one or more optical sensors positioned in proximity to a targeted region of a subject's head: analysing the sensor data to determine an activity measure: determining the one or more updated stimulation parameter values based on the determined activity measure, wherein the updated stimulation parameter values are indicative of characteristics of transcranial electrical stimulation to be delivered to the subject by an electrical stimulation generator under the control of the control device; and transmitting the updated stimulation parameter values to the control device.

Some embodiments relate to a non-transitory machine-readable medium storing instructions which, when executed by one or more processors, cause a computing device to perform the methods disclosed.

Some embodiments relate to a system for inferring symptom severity and/or behavioural progress of a subject undergoing treatment for one or more symptoms of a neurological condition, the system comprising: a control device configured to receive sensor data from one or more optical sensors arranged to be positioned in proximity to a targeted region of the brain of the subject: wherein the system is further configured to: determine task data comprising one or more scores associated with the subject's performance in undertaking one or more respective tasks; determine a symptom severity or progress measure based on the sensor data and the task data; and output the symptom severity and/or progress measure.

The symptom severity and/or progress measure may comprise a plurality of scores, each indicative of a severity level of a behaviour or experiences associated with the neurological condition The neurological condition may be ADHD, and the symptom severity and/or progress measure comprises a score for one or more of: (i) an overall ADHD rating scale score. (ii) an ADHD core symptom score, (iii) an inattention score, (iv) a hyperactivity score, and (v) an impulsivity score.

In some embodiments, the system comprises a symptom severity and/or progress determination model configured to determine the symptom severity and/or progress measure based on the task data and the sensor data, wherein the symptom severity and/or progress determination model has been trained using data derived from a clinical population.

In some embodiments, the system comprises a feature extraction module configured to determine one or more features values from the sensor data, and to provide the feature values to the symptom severity and/or progress determination model. The one or more feature values may be indicative of functional connectivity between pairs of optical sensor channels and/or statistical measures of data acquired from optical sensor channels.

The one or more feature values derived from sensor data acquired from optical channels configured to measure activity at the right lateral prefrontal cortex may be provided to the symptom severity and/or progress determination model to determine an overall ADHD symptom severity measure. Feature values based on reaction time and omission error metrics of the task data may be provided to the symptom severity and/or progress determination model to determine the overall ADHD symptom severity measure.

The one or more feature values derived from sensor data acquired from optical channels configured to measure activity at the right lateral prefrontal cortex may be provided to the symptom severity and/or progress determination model to determine a ADHD core symptom severity measure.

The one or more feature values derived from sensor data acquired from optical channels configured to measure activity at the subject's medial prefrontal cortex, and/or at a medial prefrontal cortex toward, overlapping or bordering on the subject's left lateral prefrontal cortex may be provided to the symptom severity and/or progress determination model to determine an inattention severity measure. Feature values based on reaction time and omission error metrics of the task data may be provided to the symptom severity and/or progress determination model to determine the inattention severity measure.

The one or more feature values derived from sensor data acquired from optical channels configured to measure activity at the subject's right lateral prefrontal cortex, the left lateral prefrontal cortex, and/or the region overlapping with the left lateral prefrontal cortex and the medial prefrontal cortex may be provided to the symptom severity and/or progress determination model to determine a hyperactivity severity measure.

The one or more feature values derived from sensor data acquired from optical channels configured to measure activity at the subject's medial prefrontal cortex, and/or the medial prefrontal cortex toward, overlapping or bordering on the subject's right lateral prefrontal cortex may be provided to the symptom severity and/or progress determination model to determine an impulsivity severity measure. Feature values based on reaction time metrics of the task data may be provided to the symptom severity and/or progress determination model to determine the impulsivity severity measure.

The system may further comprise a head mountable array carrying the optical sensors, and wherein the optical sensors are functional near infrared spectroscopy sensors (fNIRS). The system may further comprise: an optical sensor module coupled to the one or more optical sensors, the optical sensor module configured to cause light to be emitted from a respective emitter of the one or more optical sensors, and to receive a signal indicative of reflected light from a respective detector of the of the one or more optical sensors, wherein the signal is indicative of cerebral haemodynamic response in relation to neural activities in the targeted region: wherein the optical sensor module is configured to provide the sensor data to the control device, the sensor data being based on the signals received from the respective one or more sensors; and wherein the optical sensor module is configured to operate in response to instructions received from the control device.

The control device may be configured to cause the optical sensor module to switch the emitter of the one or more optical sensors on and off at a relatively high frequency to create a lock-in-amplifier effect to improve the signal to noise ratio (SNR) of the respective detected reflected light signals. Each of the one or more optical sensors may comprise an emitter and a first and second detectors and form two detector channels, and wherein the control device is configured to demodulate the signal of the detector channels of each of the optical sensors.

The sensor data from the plurality of functional channels may be down sampled.

The sensor data may comprise measured data including one or more of: (i) reflected light intensity at two distinctive wavelengths detected by the one or more sensors; (ii) oxygenated haemoglobin (HbO) concentration; (iii) deoxygenated haemoglobin (HbR) concentration; (iv) total haemoglobin (ThB) concentration; and (v) relative changes in any of measures (i) to (iv).

The system may be configured to determine a quality measure indicative of a quality of each detector channel of the one or more optical sensors, and responsive to the quality measure falling below a quality threshold, excluding sensor data from the respective detector channel when determining the symptom severity or progress measure.

The system may be configured to determine a subset of the sensor data comprising task associated sensor data acquired while the subject was performing a task based on timestamped sensor data and timestamped task data. The system may further comprise a feature extraction module configured to extract one or more features from the task associated sensor data, and wherein determining the symptom severity or progress measure based on the sensor data and the task data comprises determining the symptom severity or progress measure based on the one or more features and task data.

The system may comprise a cognitive performance monitoring application configured to assess the subject performing one or more specific tasks: allocate the one or more task scores to the subject based on their performance in undertaking the task, wherein the task data comprises the one or more task scores.

The control device may be configured to send stimulation instructions to an electrical stimulation generator to cause the electrical stimulation generator to deliver transcranial electrical stimulation to one or more electrodes arranged to be positioned in proximity to the targeted region of the brain of the subject.

The head mountable array may further carry the one or more electrodes.

The system may further comprise a computing device or server in communication with the control device across a communications network, and wherein the computing device or server is configured to: receive the sensor data from the control device; determine the task data; determine the symptom severity or progress measure based on the sensor data and the task data; and output the symptom severity or progress measure. The control device may be configured to transmit the sensor data to the computing device or server.

The control device may be configured to allow for selection of a subset of the electrodes of the array to be used when administering stimulation to thereby tailor the control device to suit a particular subject's head size. The control device may be configured to receive a head size indication from the subject via a user interface and to determine the subset of electrodes to be used based on the head size indication. The control device may be configured to: deliver at least a first test signal to each of one or more subsets of electrodes of the array; analyse a test response detected by respective sensor modules; determine a suitable subset of electrodes for the subject based on the detected test responses; and select the suitable subset of electrodes for use in administering the stimulation to the head of the subject.

The system may further comprise a positioning feedback module configured to assist the subject in correct placement of the array relative to the subject's head. The positioning feedback module may be configured to: determine one or more images of the subject donning the array of the system: detect a position of one or more facial features of the subject within the one or more images: detect a position of the array within the one or more images relative to the determined facial features: compare a determined position of the array to a target position; and responsive to determining that the position of the array falls within an acceptable range, determine the array to be correctly placed; and responsive to determining that the position of the array falls within an acceptable range, determine the array to be incorrectly placed, provide feedback to the subject via a user interface to assist them to reposition the array with a view to achieving the target position.

Some embodiments relate to a system for inferring symptom severity and/or behavioural progress of a subject undergoing treatment for one or more symptoms of a neurological condition, the system configured to: receive sensor data from a control device, the sensor data derived from one or more optical sensors positioned in proximity to a targeted region of a subject's head; determine task data comprising one or more scores associated with the subject's performance in undertaking one or more respective tasks; determine a symptom severity or progress measure based on the sensor data and the task data; and output the symptom severity or progress measure.

Some embodiments relate to a method for inferring behavioural progress of a subject undergoing treatment for one or more symptoms of a neurological condition, the method comprising: receiving sensor data from one or more optical sensors arranged to be positioned in proximity to a targeted region of the brain of the subject: determining task data comprising one or more scores associated with the subject's performance in undertaking one or more respective tasks: determining a symptom severity or progress measure based on the sensor data and the task data; and outputting the symptom severity and/or progress measure.

Some embodiments relate to a method for inferring symptom severity and/or behavioural progress of a subject undergoing treatment for one or more symptoms of a neurological condition, the method comprising: receiving sensor data from a control device, the sensor data derived from one or more optical sensors positioned in proximity to a targeted region of a subject's head: determining task data comprising one or more scores associated with the subject's performance in undertaking one or more respective tasks: determining a symptom severity or progress measure based on the sensor data and the task data; and outputting the symptom severity and/or progress measure.

Some embodiments relate to a server arranged to communicate across a communications network with a control device for detecting brain activity of a subject, the server configured to: receive sensor data from the control device, the sensor data indicative of reflected light intensity at two distinctive wavelengths detected by one or more sensors coupled to the control device while the sensors are positioned in proximity to a targeted region of a subject's brain, and while the subject was undertaking a specific task: receive one or more task scores from a cognitive assessment application deployed on a computing device associated with the subject, wherein the cognitive assessment application is configured to assess the subject performing the specific task and allocate the one or more task scores to the subject based on their performance: provide, as an input to a symptom severity or progress determination model, the sensor data and the one or more task scores; and determine, as an output of the symptom severity or progress determination model, a symptom severity or progress measure, the symptom severity or progress measure being indicative of severity of the symptom of the neurological condition or the progress the subject is making in treating symptoms of neurological condition.

Some embodiments may relate to a computer implemented method of inferring behavioural progress of a subject undergoing treatment for one or more symptoms of a neurological condition, the method comprising: receiving sensor data from the control device, the sensor data indicative of reflected light intensity at two distinctive wavelengths detected by one or more sensors coupled to the control device while the sensors positioned in proximity to a targeted region of a subject's brain, and while the subject was undertaking a specific task; receiving one or more task scores from a cognitive assessment application deployed on a computing device associated with the subject, wherein the cognitive assessment application is configured to assess the subject performing the specific task and allocate the one or more task scores to the subject based on their performance: providing, as an input to a symptom severity or progress determination model, the sensor data and the one or more task scores; and determining, as an output of the symptom severity or progress determination model, a symptom severity or progress measure, the symptom severity or progress measure being indicative of the severity of the symptom of the neurological condition or the progress the subject is making in treating symptoms of neurological condition.

Some embodiments relate to a non-transitory machine-readable medium storing instructions which, when executed by one or more processors, cause a computing device to perform the methods disclosed.

Some embodiments relate to a head-mountable apparatus comprising: an array comprising a plurality of optical sensor components disposed along a length of the array, each optical sensor component comprising an emitter and a first and second detector, wherein the emitter is disposed in proximity to the first detector to form a first relatively short channel, and the emitter is disposed at a relatively greater distance from the second detector to form a first relatively long channel: an optical sensor module configured to cause light to be emitted from selected emitters of the optical sensor components and to receive signals indicative of reflected light from the first and second detectors of selected optical sensor components, wherein the signals are indicative of cerebral haemodynamic response in relation to neural activities in regions targeted by emitter detector pairs; and wherein the array further comprises a plurality of electrodes, each electrode disposed between a pair of neighbouring optical sensor components. Both the emitter and the first detector may be disposed toward a first end of the array and the second detector is disposed at a second end of the array, The one or more electrodes may be configured to deliver electrical stimulation to the subject. The one or more electrodes may be configured to determine an electroencephalogram (EEG) signal from the subject.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Various ones of the appended drawings merely illustrate example embodiments of the present disclosure and cannot be considered as limiting its scope.

FIG. 8 depicts a process flow of a method of controlling delivery of transcranial electrical stimulation, according to some embodiments:

FIG. 9A is a graphical depiction of a combined electrical current comprising transcranial direct current stimulation (tDCS) and transcranial alternating current stimulation (tACS) against time, the combined electrical current being supplied by an electrical stimulation source of the system of FIG. 2, according to some embodiments;

DETAILED DESCRIPTION

Figure 1:
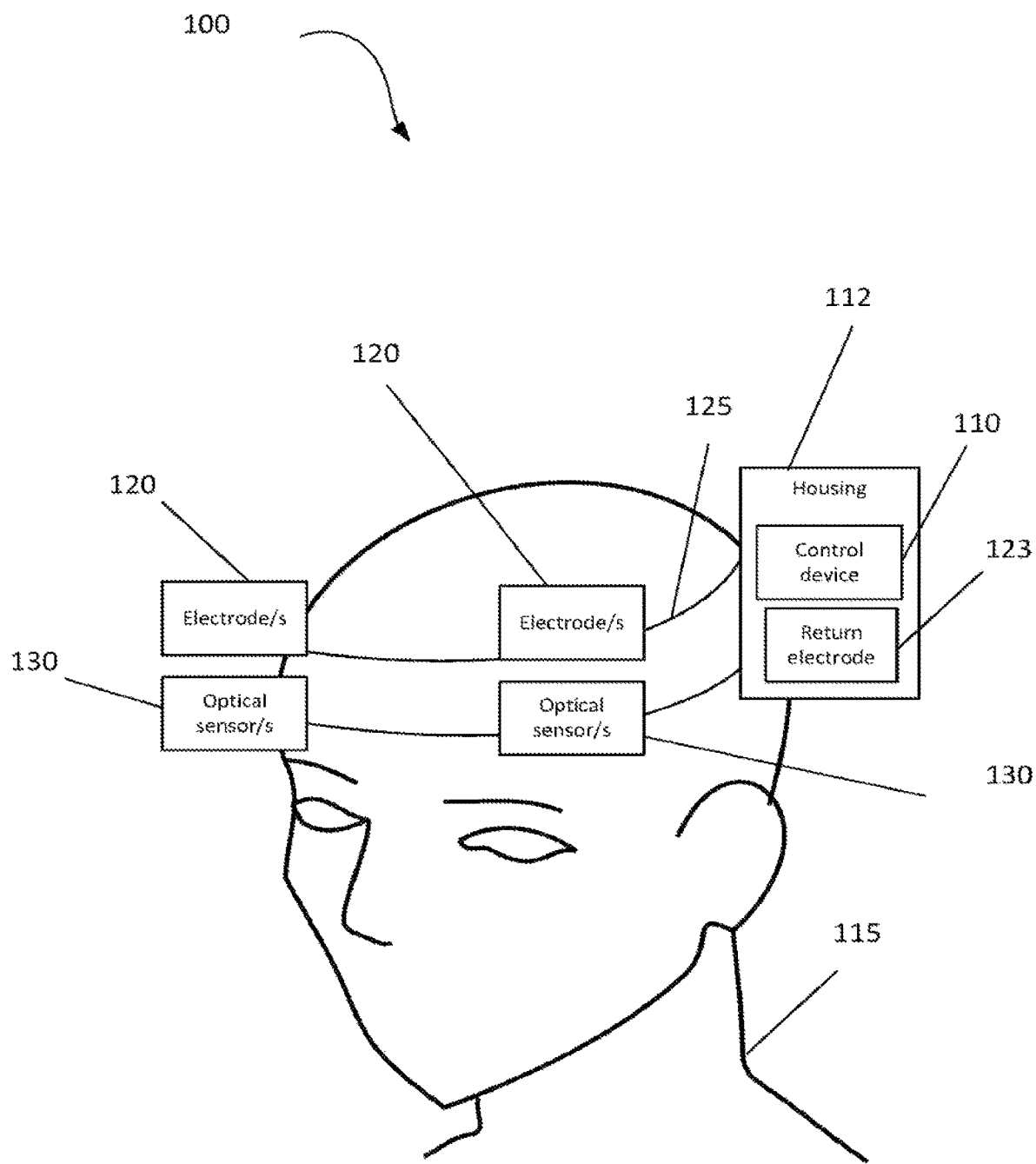
FIG. 1 depicts a schematic of an apparatus for monitoring and/or treating symptoms of neurological conditions placed on a user, according to some embodiments.

Embodiments generally relate to methods and systems for monitoring and in some embodiments, treatment of symptoms of neurological conditions in subjects, and in particular, neurobehavioural disorders, such as attention deficit hyperactivity disorder (ADHD).

Application of electrical stimulation to the brain of a subject with neurobehavioural disorders is effective in inducing physiological changes that over time result in neuroplastic alterations of cortical function, which are thought to be key to learning and memory formation. However, the extent and duration of stimulation required to improve cognitive performance in such subjects for a specific period of time, for example, while performing a task, may vary from task to task and from subject to subject. Some described embodiments disclose techniques for controlling the delivery of electrical stimulation to a subject, and adjusting parameter(s) of the electrical stimulation based on the subject's measured brain activity, which may improve in response to the electrical stimulation.

In some embodiments, a system is provided for controlling delivery of electrical stimulation to a subject's brain and monitoring or detecting a cerebral haemodynamic response in relation to neural activities. In some embodiments, a system is provided for detecting a cerebral haemodynamic response in relation to neural activities. The system is further configured to determine an activity measure based on the cerebral haemodynamic response and adjust one or more parameters of the simulation based on the activity measure. Accordingly, in some embodiments, the system provides for "closed loop" monitoring of brain activity which allows for confirmation that the stimulation applied did in fact reach the brain of the subject, and determination of whether it is producing the desired effect. It can also allow action to be taken in the case that the current is not getting through or if the current that is getting through is not sufficient to produce the desired effect. For example, electrodes used to deliver the stimulation may be adjusted and/or stimulation parameters changed to improve the application of the stimulation and the result achieved. This can improve patient outcomes.

The system, or at least a part of the system, comprises a head-worn or head mountable apparatus, such as a headset, carrying electrodes for delivering the stimulation and/or sensors for monitoring the brain's activities. The subject may be asked to perform specific tasks or cognitive assessments while wearing the head-worn apparatus to target specific areas of the brain. In some embodiments, a cognitive performance monitoring application deployed on a computing device (such as a smart phone) may be configured to cooperate with the system to coordinate the task to be performed with the operation of the system.

In some embodiments, the system, or the apparatus of the system, comprises a control device is arranged to detect or monitor activity in the targeted areas via a plurality of optical sensors or optodes, such as functional near infrared spectroscopy sensors (fNIRS), positioned in key locations on the subject's head. For example, the head-worn apparatus may be configured to appropriately position the sensors relative to the subject's head. Performance of specific tasks by the subject will result in activity in particular parts of the subject's brain and this activity is detected and monitored by the control device via the sensors.

The control device causes transcranial electrical stimulation to be delivered (by an electrical stimulation generator) to a plurality of electrodes placed at or near a specific location on the subject's head, such as the frontal region of the head (forehead), so as to stimulate specific regions of the brain with a view to treating or producing a beneficial effect on the symptoms of neurobehavioural disorders such as ADHD. Stimulation in specific regions of the brain increases the likelihood of neuronal firing (Chhatbar et al., 2018: Vöröslakos ct al., 2018; Islam, Aftabuddin, Moriwaki, Hattori & Hori, 1995: Polania, Nitsche & Paulus, 2010). Repeated neuronal firing in this way has been found to increase the strength of neuronal connections via long term potentiation and the upregulation of Brain derived neurotrophic factors (Liebetanz, Nitsche, Tergau & Paulus, 2002: Cocco et al., 2020; Cavaleiro, Martins, Gonçalves & Castelo-Branco, 2020). This is in line with Hebbian theory of learning and neuroplasticity, which states that cells that fire together wire together (Hebb, 1949; Shatz, 1992).

Neuronal excitability of the subject changes in response to the application of the electrical stimulation and variations in cortical activity can be detected by the control device via the sensors. The system is configured to analyse measured data (cerebral haemodynamic response data) from the optical sensors, which may be positioned in proximity to the electrode(s), the measured data being based on or comprising optical signal(s) from the respective sensor(s). For example, the optical signals may be indicative of the intensity of the reflected light at two or more distinct wavelengths, and the measured data may comprise the optical signals, and/or curves indicative of the concentration changes of oxygenated haemoglobin (HbO), deoxygenated haemoglobin (HbR) and/or a combination of the two (total haemoglobin ThB). Based on the analysis, the system determines an activity measure indicative of the activity of the region of the brain being targeted, which may have been impacted by the stimulation, determines value(s) for stimulation parameter(s) based on the activity measure, and transmits stimulation instructions comprising the stimulation parameter(s) to the electrical simulation generator to modify or adjust simulation being or to be delivered to the subject via the electrodes.

In some embodiments, the control device of the system is configured to analyse the measured data. The control device may be further configured to determine the activity measure indicative of the activity of the region of the brain being targeted, determine value(s) for stimulation parameter(s) based on the activity measure, and transmit stimulation instructions comprising the stimulation parameter(s) to the electrical simulation generator to modify or adjust simulation being or to be delivered to the subject via the electrodes.

In some embodiments, the control device may be configured to provide or stream measured data to a computing device or a server, for example, via a wireless communications network, such as Bluetooth. The computing device or server may be configured to determine the activity measure indicative of the activity of the region of the brain being targeted and determine value(s) for stimulation parameter(s) based on the activity measure. The computing device or server may transmit stimulation instructions comprising the stimulation parameter(s) to control device to cause the control device to cause the electrical simulation generator to modify or adjust simulation being or to be delivered to the subject via the electrodes.

The activity measure may be derived from feature(s) or characteristic(s) extracted from the optical signals received from the sensors, and which may be indicative of biomarker(s) associated with a change in cortical activity. For example, when a subject starts undertaking a task and/or is subjected to delivered electrical stimulation, the neural activity that results causes physiological changes in the local network of blood vessels in the brain of the subject, which may cause changes in cerebral blood volume per unit of brain tissue (CBV), the rate of cerebral blood flow, and the concentration of oxyhemoglobin and deoxyhemoglobin. The optical signals detected are indicative of these cerebral haemodynamic responses in relation to the activity.

In some embodiments, the system (for example, the control device, computing device or server) may employ a univariate or multivariate activity determination model configured to receive as inputs, feature(s) extracted from the sensor signal(s), and to provide as an output, the activity measure. For example, the activity measure may be indicative of whether or not, or a confidence score associated with whether or not, sufficient stimulation has been delivered to the subject to achieve a desired level of activity at the target area. The activity measure may be indicative of whether the user's brain activity is deemed to be sufficiently active, underactive, overactive, too responsive, sufficiently responsive, or under responsive.

In such embodiments, the system may determine stimulation parameters, or changes to stimulation parameters based on the activity measure. In some embodiments, the system may employ a univariate or multivariate stimulation control determination model configured to receive, as an input, the activity measure and in some embodiments, the previously applied stimulation parameters, and to provide as an output, updated stimulation parameter value(s). The stimulation parameter(s) may be simply an on/off parameter value, or may include values for parameters such as frequency, duration, amplitude etc. The control device transmits stimulation instructions comprising the stimulation parameter(s) to the electrical stimulation generator to adjust the stimulation being delivered to the patient, for example, to cause cessation of the stimulation, or by adjusting characteristic(s) of the stimulation. In some embodiments, the computing device or server may transmit the stimulation instructions to the control device.

In some embodiments, the activity determination model and/or the stimulation control determination model may be trained on data derived from the subject such that the control device is configured to provide customised treatment to the specific subject. By customising the model(s) for the user, the model(s) tend to be more accurate, resulting in an improved control device. In some embodiments, a global model for the activity determination model and/or the stimulation control determination model may be trained on a global dataset comprising examples from a plurality of subjects. The global dataset may be filtered to include examples derived from subject having some or more factors in common with a candidate subject, such as age and sex. The trained global model(s) may then be refined based on data associated with or collected from the candidate subject to provide a customised, user specific model(s). By training the model(s) on a global dataset, and refining the trained global model based on user specific data, the resulting customised, user specific model(s) can be determined based on a relatively small set of candidate subject data.

In some embodiments, a subject performs tasks or activities to activate specific regions of the brain with a view to targeting the effect of stimulation to the regions of the brain activated by those tasks. Such tasks may focus on behaviours or symptoms such as working memory, attention, and/or impulse control. Scores relating to those task (task data), and sensor data recorded before, during and after the tasks are performed may be analysed by the system to determine a symptom severity or progress measure. In some embodiments, the system may be configured to determine a severity score for a plurality of symptoms, behaviours and/or experiences of a neurobehavioural disorder.

The symptom severity or progress measure may be derived from feature(s) or characteristic(s) extracted from the optical signals received from the sensors, and which may be indicative of biomarker(s) associated with a change in cortical activity. For example, when a subject starts undertaking a task, the neural activity that results causes physiological changes in the local network of blood vessels in the brain of the subject, which may cause changes in cerebral blood volume per unit of brain tissue (CBV), the rate of cerebral blood flow, and the concentration of oxyhemoglobin and deoxyhemoglobin. The optical signals detected are indicative of these cerebral haemodynamic responses in relation to the activity.

In some embodiments, the system (for example, the control device, computing device or server) may employ a univariate or multivariate symptom severity or progress determination model configured to receive as inputs, feature(s) extracted from the sensor signal(s), and task data, and to provide as an output, the symptom severity or progress measure. The progress measure may be indicative of the symptom severity relative to a previous predicted symptom severity and thus, the progress the subject is making in treating symptoms of neurological condition. For example, where the symptom severity or progress determination model 327 is configured to determine the symptom severity or progress of characteristics or behaviours associated with ADHD, the symptom severity or progress determination model 327 may provide, as an output, values for one or more of: an overall ADHD rating scale score, an ADHD core symptom score, an inattention score, a hyperactivity score, and an impulsivity score.

In some embodiments, information associated with a session for treating or monitoring symptoms of neurobehavioural disorders being undertaken by a subject may be transmitted to the cognitive performance monitoring or assessment application or other application deployed on the subject's computing device, such as notifications relating to the process, or metrics of their physical condition and/or performance during the session.

The system can be used by users on ad hoc basis, for example, to assist in stimulating particular areas or regions of the brain when performing a task, and may thereby improve the immediate performance of the user in performing the task. Accordingly, the system can provide short-term benefits to user. For example, a child may elect to use the system when doing their homework. In some embodiments, the system can be used to assist in monitoring particular areas or regions of the brain when performing a task, and may thereby provide information about the user's neural activity at particular areas or regions of the brain when performing the task. The system can be used on a regular basis, as part of treatment plan, for example, and may thereby improve the longer term cognitive performance of user's by increasing the strength of neuronal connections via long term potentiation and the upregulation of brain derived neurotrophic factors.

FIG. 1 depicts an embodiment of an apparatus 100 for monitoring and/or treatment of symptoms of neurobehavioural disorders, such as ADHD. In some embodiments, the symptoms being targeted working memory, attention, and/or impulse control.

Figure 4:
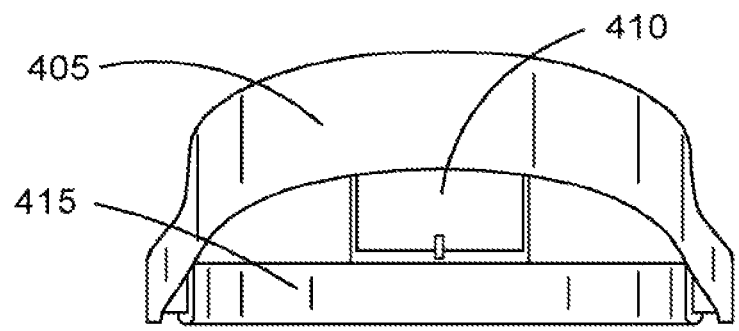
FIGS. 4, 5 and 6 depict a front view and perspective views, respectively, of a mount of the apparatus of FIG. 1, according to some embodiments.
Figure 5:
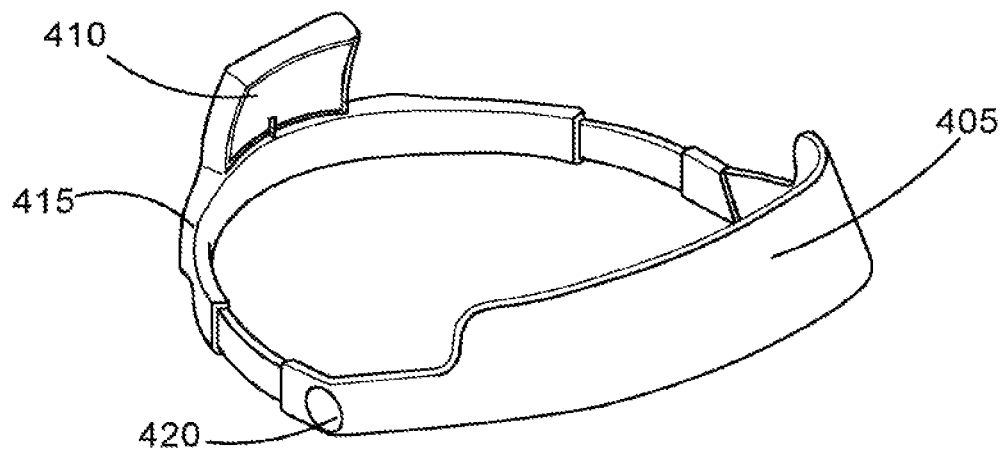
Figure 6:
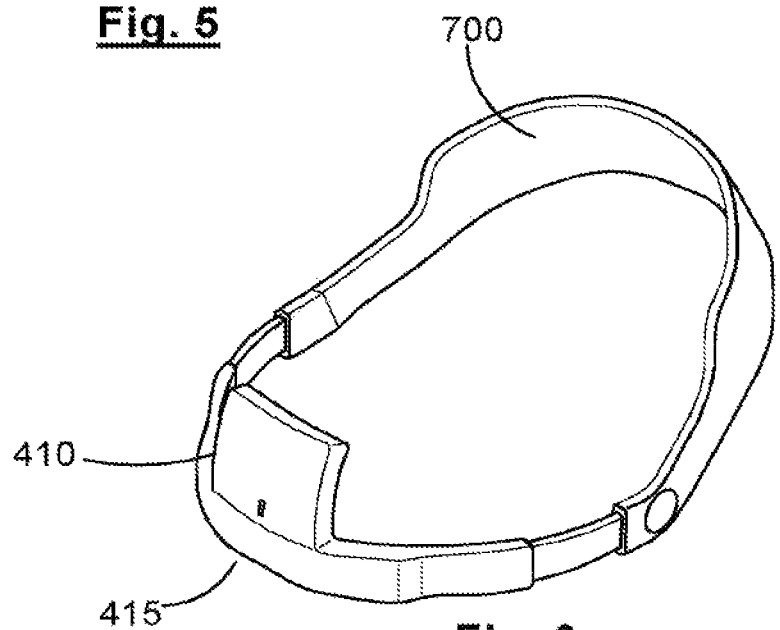

In some embodiments, and as illustrated, the apparatus 100 may comprise a mount 125 configured to be worn on the head by a subject or user 115. For example, the mount 125 may be a head mounted band or cap. A further example of embodiment of the mount 125 of the apparatus 100 is illustrated in FIGS. 4, 5 and 6, as discussed in more detail below. The apparatus 100 may be a portable or wearable headset.

The apparatus 100 may comprise one or more electrodes 120 configured to be attached near to or on the head of the user 115 in a target area or region of interest. In some embodiments, and as illustrated, the electrodes 120 may be arranged relative to one another in an array, and/or may be carried by the mount 125. The electrode(s) may be configured to receive electrical stimulation from an electrical stimulation generator or source 350 (FIG. 3) under control of a control device 110, and deliver transcranial electrical stimulation or transcranial neurostimulation to the target area of the brain of the user 115. For example, the electrode(s) 120 may be configured to deliver a supplied electrical current such as transcranial direct current stimulation (tDCS), transcranial alternating current stimulation (tACS), and/or transcranial random noise stimulation (tRNS) to the target area. The electrodes 120 may comprise a number of individually attachable electrodes, or more than one electrode in an array configuration. Application of electrical stimulation to the brain affects brain activity, and accordingly, the configured location or position of the electrode(s) 120 relative to one another, and relative to the head and brain of the user 115 when the apparatus 100 is worn by the user 115, allows for specific regions of the brain to be targeted by the stimulation.

Figure 7A:
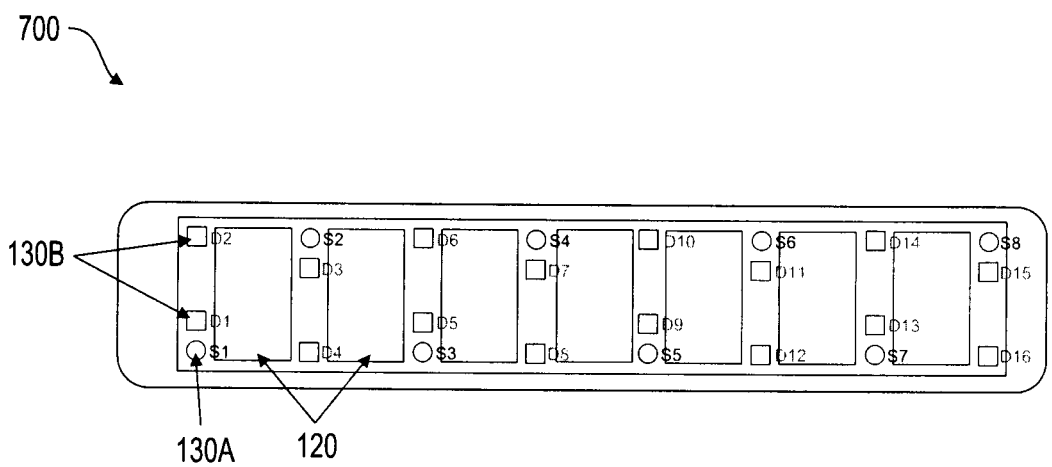
FIG. 7a depicts an electrode and optical sensor mount array of the apparatus of FIG. 1, according to some embodiments.
Figure 7B:
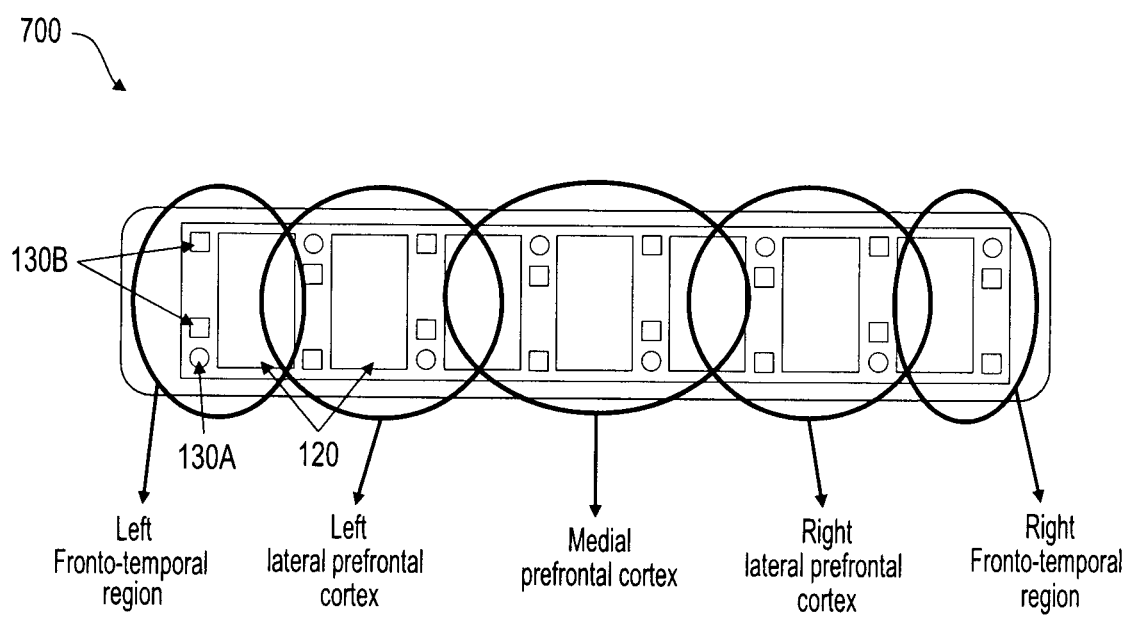
FIG. 7b depicts an electrode and optical sensor mount array of the apparatus of FIG. 1, according to some embodiments.

The apparatus 100 further comprises one or more optical sensors 130. The optical sensor(s) 130 may comprise functional near infrared spectroscopy sensors (fNIRS), configured to emit near-infrared light (typically with a wavelength of 650-1000 nm) and measure a cerebral haemodynamic response associated with cerebral activity. Specifically, the optical sensor(s) 130 is configured to emit light at two or more different wavelengths. To this end, each optical sensor 130 comprises a light emitter 130A and corresponding light detector(s) 130B (FIGS. 7a and 7b). The light emitter 130A and light detector 130B pairs are arranged or placed ipsi-laterally on the mount 125, as shown in FIGS. 7a and 7b, and/or otherwise on user's head, so recorded measurements are due to back-scattered (reflected) light following elliptical pathways. The reflected light detected by optical sensor(s) 130 is indicative of concentration changes of oxygenated haemoglobin (HbO) and deoxygenated haemoglobin (HbR), and these sensed signals (or measured information derived from the recorded data) are provided to the control device 110 for analysis. Functional near infrared spectroscopy sensors (fNIRS) indirectly measure neuronal activity in the brain's cortex via neuro-vascular coupling by quantifying haemoglobin-concentration changes in the brain based on optical intensity measurements, as described in Noman Nascer and Keum-ShikHong, 'fNIRS-based brain-computer interfaces: a review' (2015) Frontiers in Human Neuroscience, the entire content of which is incorporated herein by reference.

The optical sensors 130 may be configured to record changes in blood oxygenation in a certain region of the brain of a user 115, depending on the placement of the sensor(s) relative to the user's brain. Blood oxygen changes reflect changes in brain activity as it represents the energy needs of that area of the brain, whether increased due to increased neuronal activity, or decreased, due to decreased neuronal activity, shown by the metabolism of oxygen. This may be achieved by the analysis of the raw signal on the basis of light reflection and absorption, and/or converting the raw signals into a hemodynamic response.

When the apparatus 100 is applied to a subject's head, the optical sensors 130 are configured to measure brain activity at a location or position of the brain of the subject that is midway, or at the midpoint between a light emitter 130A and light detector 130B pair. Typically, an optimal or maximum of electrical stimulation being delivered to the brain of the subject via each electrode 120 is at a point directly underneath the respective electrode 120. Accordingly, the optical sensors 130 are configured to measure brain activity around and between stimulating electrodes. By configuring the placement of the optical sensor(s) 130, that is the light emitter 130A and light detector 130B pair, relative to respective electrode(s) 120, specific sites or locations of the brain of the subject can be targeted with stimulation and associated (or responsive) brain activity measured. An example of an arrangement of the optical sensors 130 and electrodes 120 is described in more detail below with reference to FIGS. 7a, 7b, and 12.

When the array 700 of the apparatus 100 is placed on a user's head, light detector pairs D1, D2 and light emitter S1 are directed to the part of the left front-temporal region of a user's brain: light detector pairs D3, D4, and D5, D6, and, and light emitters S2 and S3 are directed to the left lateral prefrontal cortex of a user's brain: light detector pair D7, D8 and D9, D10, and light emitters S4 and S5 are directed to the medial prefrontal cortex of a user's brain; light detector pairs D11, D12, and D13, D14, and light emitters S6 and S7 are directed to the right lateral prefrontal cortex of a user's brain; and light detector pair D15, D16, and light emitter S8 are directed to the right fronto-temporal region of a user's brain.

The use of fNIRS sensors as the optical sensors 130 may allow for a relatively low cost, portability, safety, accuracy and/or ease of use when compared to other sensors. In particular, fNIRS sensors are less sensitive to movement artefact than other blood oxygenation sensors, such as magnetic resonance imaging (MRI). fNIRS sensors are also less susceptible to electrical noise and movement artefact compared to other electrical sensors, such as electroencephalograms (EEGs). Accordingly, the use of fNIRS sensors as optical sensors 130 allows for the sensors 130 to be placed relatively close to the electrical stimulation site of the electrodes 120, and thereby provide an improved reading. Furthermore, fNIRS sensors have a relatively higher spatial resolution compared to EEG, and in the described embodiments exhibits higher signal quality. And further, fNIRS sensors allow for the measurement and recording of activity data while stimulation is being delivered, which is difficult to do accurately and effectively with EEGs. This is because neural signals are very small in amplitude and can be overshadowed by other signals and noise. The stimulation generator delivers electrical current, which is picked up by the EEG and the amplitude of the stimulation signal is many order of magnitude larger than the neural signal. If attempting to record EEG while applying electrical stimulation, most of the EEG signal will result from the electrical stimulation and the neural response can be difficult to detect. Furthermore, the stimulation can saturate the EEG sensors making it impossible to see any neural signal. As a result, using EEG to record data while stimulation is being applied is difficult, prone to failure due to the relatively high chance of saturation of the sensors, and involves complex signal processing to attempt to recover the neuronal signals. Accordingly, the use of fNIRS sensors as the optical sensors 130 allows for a more efficient determination of improved signal quality with greater confidence of accuracy.

Figure 3:
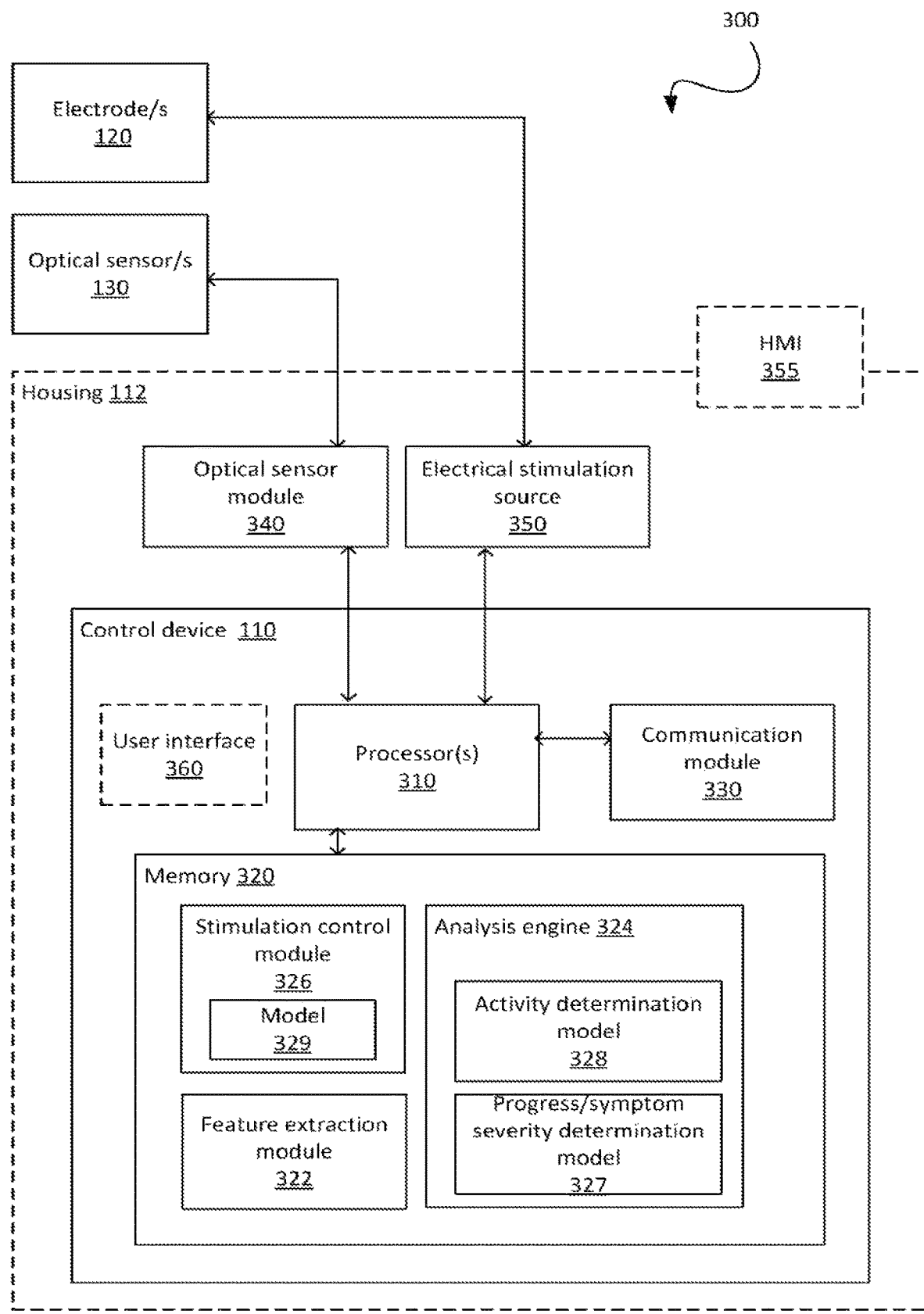
FIG. 3 depicts a block diagram of the apparatus of FIG. 1, according to some embodiments.

The apparatus 100 further comprises the control device 110. As illustrated, the control device 110 may be housed in housing 112. The housing 112 may further comprise an optical sensor module 340 and/or the electrical stimulation source 350 (FIG. 3). The housing 112 may also comprise an electrode (back electrode) 123, which acts as a return electrode pad for the electrodes 120. As discussed in more detail below with reference to FIG. 3, the control device 110 may be configured to transmit stimulation instructions, which may include stimulation parameter value(s) to the electrical stimulation source 350 to cause the electrical stimulation source 350 to deliver transcranial electrical stimulation to the electrode(s) 120, and to target areas of the brain via the electrode(s) 120. The control device 110 may be configured to receive response data, such as response signals, from the sensor(s) 130 via the optical sensor module 340. In some embodiments, the electrodes 120 may be configured to determine a measure of electrical stimulation being delivered to the subject, for example to determine a measure of brain activity of the subject. For example, in such embodiments, the electrodes 120 may be configured to determine or receive an electroencephalogram (EEG) signal.

As illustrated, the control device 110 and/or housing 112 may be mounted at a rear portion of the mount 125 relative to the sensors 130, or at the front portion of the mount 125 relative to the sensors 130. In some embodiments, the control device 110 may be formed as part of the mount 125. For example, the control device 110 and/or housing 112 may be arranged to be position near or at the forehead or near or at the back of the head of the subject when the apparatus 100 is mounted to the subject's head.

Figure 2:
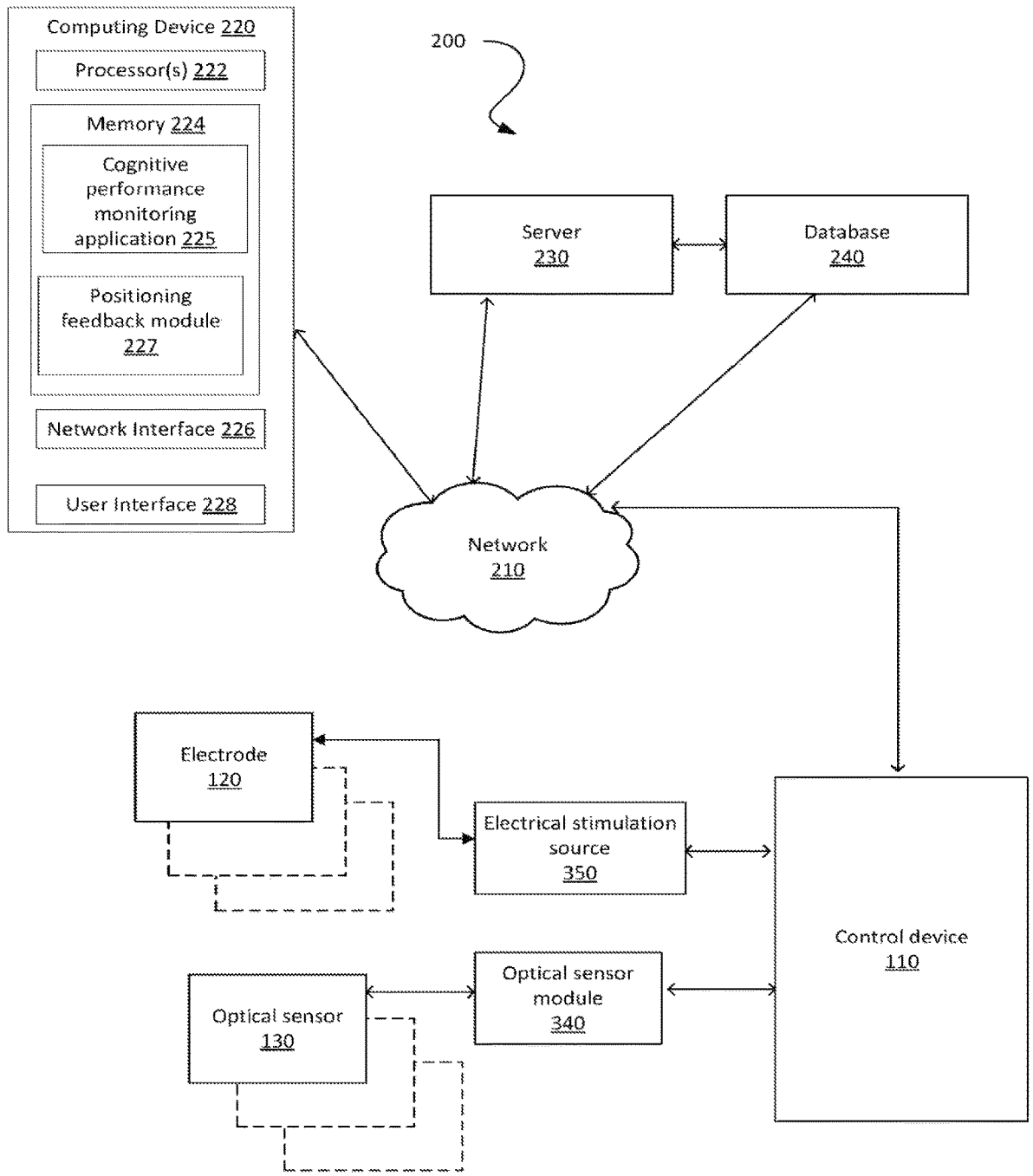
FIG. 2 depicts a block diagram view of system architecture for monitoring and/or treating symptoms of neurological conditions and comprising the device of FIG. 1, according to some embodiments.

FIG. 2 depicts a block diagram of system architecture 200 for controlling delivery of transcranial electrical stimulation to a subject and/or monitoring neural activity of the subject, according to some embodiments. The control device 110 may be in communication with a server 230, one or more computing devices 220, and/or database 240 over a communications network 210.

The network 210 may comprise at least a portion of one or more networks having one or more nodes that transmit, receive, forward, generate, buffer, store, route, switch, process, or a combination thereof, etc. one or more messages, packets, signals, some combination thereof, or so forth. The network 210 may include, for example, one or more of: a wireless network, a wired network, an internet, an intranet, a public network, a packet-switched network, a circuit-switched network, an ad hoc network, an infrastructure network, a public-switched telephone network (PSTN), a cable network, a cellular network, a satellite network, a fiber optic network, some combination thereof, or so forth.

Server 230 may comprise one or more processors or computing devices configured to share data or resources among multiple network devices. Server 230 may comprise a physical server, virtual server, or one or more physical or virtual servers in combination.

Database 240 may comprise a data store configured to store data from network devices over network 210. Database 240 may comprise a virtual data store in a memory of a computing device, connected to network 210 by server 230 or directly to the network 210.

The electrical stimulation source 350 is configured to receive instructions from the control device 110 to provide electrical stimulation to the one or more electrodes 120 in response to the instructions. In some embodiments, the electrical stimulation source 350 may provide information or live monitoring feedback of the electrical stimulation being applied to the control device 110 to allow the control device 110 to monitor and/or control characteristics of the electrical stimulation being provided or supplied to the electrodes 120. For example, the control device 110 may be configured to monitor the performance of the electrical stimulation source 350 to ensure that it is operating as instructed and within acceptable safety limits. The electrical stimulation source 350 may also be configured to modify stimulation parameters or characteristics of electrical stimulation applied, based on instructions received from the control device 110.

The electrical stimulation source 350 may be configured to supply electrical current such as transcranial direct current stimulation (tDCS), transcranial alternating current stimulation (tACS), and/or transcranial random noise stimulation (tRNS) to a user 115 through the one or more electrodes 120. In some embodiments, a combination of two or more stimulation types may be used, for example, where the current is positive, but also alternates.

This may provide beneficial effects of both tDCS and tACS. A graphical depiction of a combined electrical current comprising tDCS and tACS against time is depicted in FIG. 9A. In some embodiments, the electrical stimulation source 350 may be configured to provide stimulation in the frequency range of between 0.1-10 khz. The amplitude peak to peak amplitude may be in the range 0.5-4 mA.

Figure 9B:
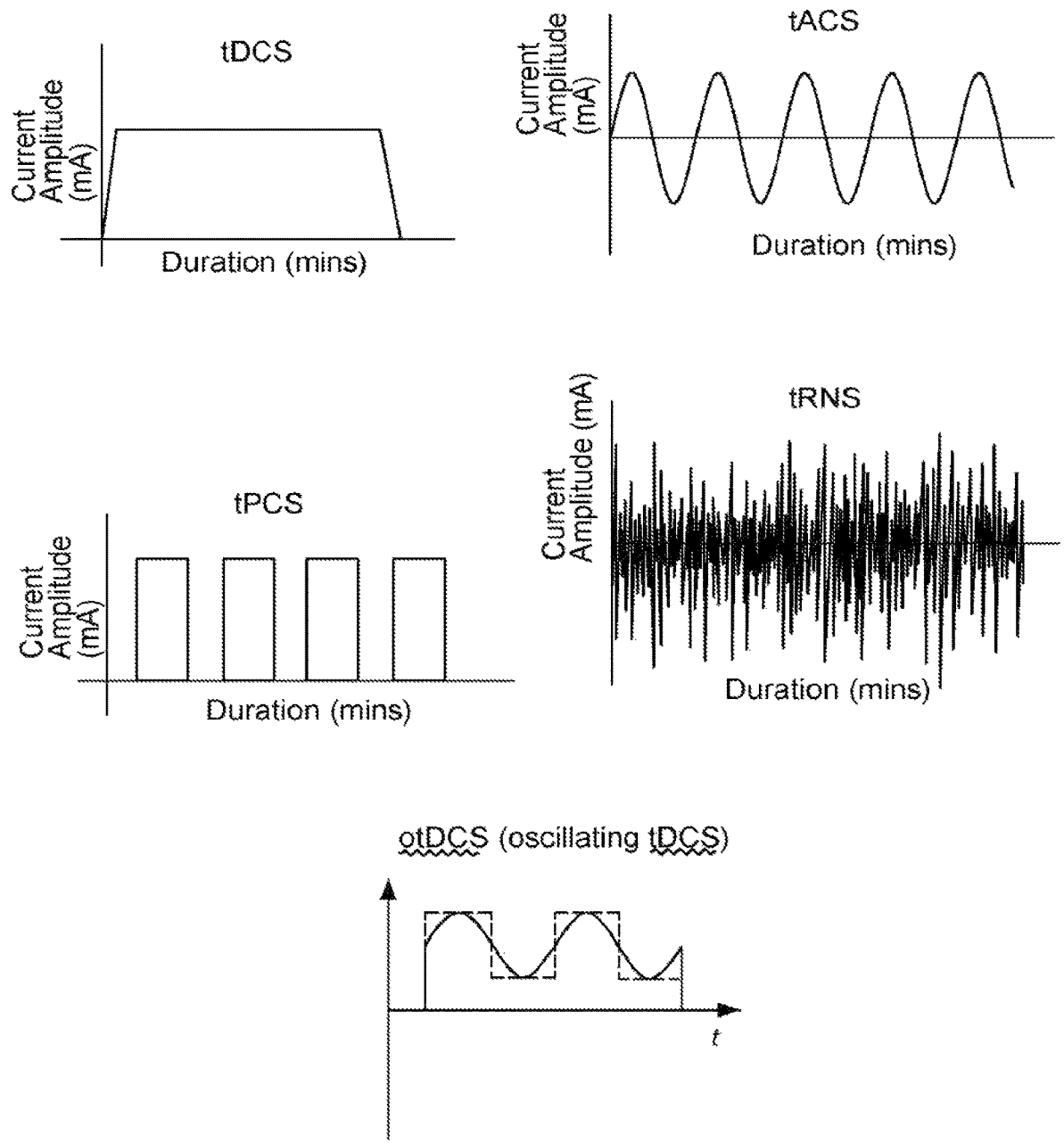
FIG. 9B is a graphical depiction of electrical currents comprising transcranial direct current stimulation (tDCS), transcranial alternating current stimulation (tACS), transcranial pulse current stimulation (tPCS), transcranial random noise stimulation (tRNS), and oscillating tDCS (otDCS) against time.

FIG. 9B is a graphical depiction of electrical currents comprising transcranial direct current stimulation (tDCS), transcranial alternating current stimulation (tACS), transcranial pulse current stimulation (tPCS), transcranial random noise stimulation (tRNS), and oscillating tDCS (otDCS) against time. In some embodiments, an otDCS signal may be generated by the combination of tDCS, tACS, and tPCS. In some embodiments, a combination of any of the depicted signal types may be used to provide transcranial stimulation (such as the combination of tDCS and tACS as seen in FIG. 9A). In some embodiments, a combination of tDCS, tACS, and/or tRNS is used to provide transcranial stimulation, or a combination of otDCS and tRNS. The electrical stimulation source 350 may be used to provide stimulation corresponding to any of the depicted signal types of FIG. 9A and FIG. 9B, by the electrode/s 120. The type of stimulation applied may be selected by a user using computing device 220, which issues instructions to the control device 110 over network 210.

The control device 110 may be configured to receive signals or measurements indicative of neuronal activity from the optical sensor module 340. The optical sensor module 340 is configured to be connected to the optical sensor(s) 130. The optical sensor module 340 may comprise an fNIRS recording module. In response to receiving instructions from the control device 110, the optical sensor module 340 is configured to cause light to be emitted from the light emitter 130A, and to receive a signal indicative of the detected or measured reflected light from the detector 130B. For example, the optical sensor module 340 may modulate instructions or signal received from the control device 110 and provide a composite signal (instructions or input signal imposed on a carrier wave) to the emitter 130A to cause the emitter to emit light with specific characteristics. In some embodiments, the reflected light signal detected by the detector 130B is demodulated by the optical sensor module 340 and the recorded data or measurements are provided to the control device 110. In other embodiments, the control device 110 may demodulate the detected reflected light signal. In some embodiments, the optical sensor module 340 may provide information or live monitoring feedback of the emitting and detecting to the control device 110 to allow the control device 110 to monitor and/or control operation of the optical sensor module 340 and the sensors 130.

In some embodiments, the optical sensor module(s) 340 may be configured to create a lock-in-amplifier effect to improve the signal to noise ratio (SNR) of the detected reflected light signal. For example, the optical sensor module 340 may be configured to modulate instructions or signal received from the control device 110 and provide a composite signal (instructions or input signal imposed on a carrier wave) to the emitter 130A to cause the emitter to emit light with specific characteristics. For example, the optical sensor module 340 may be configured to switch the emitter 130A of the respective optical sensor module 340 on and off at a relatively high frequency—the flashing frequency. In other words, the emitter(s) 130A are modulated at the flashing frequency. For example, the flashing frequency may be greater than or equal to 100 hz, for example, 125 hz. As a result, the data or signal detected by the respective detector(s) 130B is moved to a frequency around the flashing frequency. As there is often more noise at lower frequencies than higher frequencies in an analogue signal measurement, by moving the response signal to a relatively higher frequency, the SNR of the response signal may be increased.

The sampling rate used by the control device to determine sensor data from the response signal detected by the detector(s) 130B must be at least twice that of the highest frequency component of the detected response signal (Nyquist's theorem). However, the higher the sampling rate, the more difficult it tends to be to obtain reliable samples, the more samples acquired and/or the less time the processor 310 of the control device 110 has to perform other processing tasks. Accordingly, in some embodiments, a sampling rate of 4 times the highest frequency component of the emitter signal(s) 130A is chosen. For example, the flashing frequency may be 125 hz, and the sampling rate may be 500 hz, for example.

In some embodiment, the control device 110 may be a wireless device, configured to communicate with the computing device and/or server, for example, wirelessly. In some embodiment, the control device 110 may be Bluetooth enabled.

As mentioned above, sampling at a relatively high frequency results in the acquisition of a correspondingly relatively high number of data samples. For example, consider an embodiment, where the apparatus 100 carries eight optical sensors 130 (or optical sensor components 130), each providing a short channel and a long channel): (500 samples/s)*(3 Bytes/channel/s)*(16 detector channels (i.e. detectors 130B))=24 kBytes/s. Such a data rate would be too high to make use of low energy Bluetooth protocol BLE 5.0 (Typically, up to about 5 kBytes/s can be transmitted over BLE 5.0). Accordingly, down sampling and/or demodulation may be required to wirelessly transmit acquired data at this rate to the computing device, server, or other computer using some wireless technologies such as low energy Bluetooth. In some embodiments, the data rate can be reduced by demodulating the detected response signal. For example, the 16 detector channels may be split into a greater number of functional channels, such as 44 functional channels. In some embodiments, 36 long channels and 8 short channels are used. For example, the apparatus 100 of FIG. 7 with the central electrode removed or omitted may be used. The arrangement of the long and short channels is discussed below in more detail with reference to FIG. 12. The data may also be down sampled to a 10 Hz sampling rate. In this example, a new data rate is almost 10% of the original rate, while still preserving the useful information: (10 samples/s)*(6 Bytes/channel/s)*(44 channels)=2.64 kBytes/s/. Accordingly, sensor data may be acquired at a relatively high precision (for example, 3 Bytes per sample).

The apparatus 100 may comprise a plurality of functional channels, such as 44 functional channels, each comprising a pair of data channels. The functional channels may comprise an emitter and detector pair. The depth of measurement into the head achievable by the emitter detector pairs depends on the distance between the emitter and detector of a pair. In some embodiments, the functional channels may comprise long or short channels. Long channels may comprise a functional channel pair where the source and detector are spaced apart from one another at a relatively larger distance. For example, with long channels, the emitter and detector pair may be spaced apart from one another by approximately 3 cm apart. Short channels may comprise a functional channel pair where the emitter and detector are spaced apart from one another at a relatively smaller distance, such as approximately 1 cm apart. The long and short functional channels may be separated to take different measurements. Short channels, may be used to measure blood oxygenation in the scalp, due to the shorter distance between source and detector. Long channels may be used to measure blood oxygenation from both the scalp and the brain of a subject. In some embodiments, measurement of blood oxygenation from the scalp may be an unwanted effect. In such embodiments, short channels may be used to determine and allow for subtraction of the unwanted effect from the measurement determined by a respective long channel during data analysis. In some embodiments, the 44 function channels may comprise 8 short function channels and 36 long function channels.

In some embodiments, it may be preferable for any assessment and processing of the acquired sensor data to be performed on a computing device or server other than the control device 110. For example, the processor 310 of the control device 110 may not be powerful enough to perform the additional data processing while also performing its other tasks. The control device 110 may use low power components, and may not require a large battery to be used for an extended period of time. The recorded sensor data may be sent to an external device for additional processing and local/cloud storage. The control device may be a wireless headset used for recording the sensor data, and the assessment and processing of acquired sensor data may be performed on computing device 220, or server 230.

In some embodiments, the control device 110 is configured to cooperate with the electrical stimulation source 350 and optical sensor module 340 to provide closed loop stimulation and/or monitoring of brain activity of the subject. The closed loop monitoring allows for informed application of stimulation to treat specific symptoms of neurological conditions, such as neurobehavioural disorders.

In some embodiments, the control device 110 is configured to instruct the electrical stimulation source 350 to provide electrical stimulation to the electrode(s) 120 in the form of short pulses. Each short pulse signal may be characterised by an amplitude, frequency, duration and offset. In some embodiments, each short pulse is delivered one at a time. After the delivery of each pulse to the electrode(s), the optical sensor module 340 is configured to record the brain activity via the sensor(s) 130 and to provide the recording or measurement to the control device 110 for assessment. As discussed in more detail below with reference to FIG. 3, the control device 110 determines an activity measure based on the information received from the optical sensor module 340. For example, in some embodiments, the activity measure may be an indication that the user's brain activity is determined to be sufficiently active, underactive, overactive, too responsive, sufficiently responsive, or under responsive. Depending on the activity of the brain and purpose of the stimulation, the control device 110 may instruct the electrical stimulation source 350 and to deliver more pulses, having the same or different characteristics.

In some embodiments, the control device 110 is configured to instruct the electrical stimulation source 350 to provide electrical stimulation to the electrode(s) 120 in the form of a single relatively long session. The electrical stimulation signal may be characterised by an amplitude, frequency and offset. The optical sensor module 340 is configured to record the brain activity via the sensor(s) 130 during the application of the stimulation to the electrode(s) and to provide the recording or measurement to the control device 110 for assessment in real time (i.e., concurrently, or while the brain is being stimulated). The control device 110 determines an activity measure based on the information received from the optical sensor module 340. For example, in some embodiments, the activity measure may be an indication that the user's brain activity is determined to be sufficiently active, underactive, overactive, too responsive, sufficiently responsive, or under responsive. Depending on the activity of the brain and purpose of the stimulation, the control device 110 may instruct the electrical stimulation source 350 and to adjust stimulation parameters of the electrical stimulation being delivered (i.e. the characteristics of the signal). For example, the control device 110 may cause the electrical stimulation source 350 to cease providing electrical stimulation to the electrode(s) 120, or to adjust one or more of the characteristics of the signal being provided to the electrode(s) 120.

The control device 110 may be configured to transmit data received from the electrical stimulation source 350, or the optical sensor module 340, or data generated by the control device 110 itself, to the server 230 for further processing or to database 240 for storage. The control device 110 may also be arranged to receive instructions or data from the server 230. For example, the server 230 may be configured to transmit configuration instructions or updates to the control device 110 to modify how the control device 110 operates.

The control device 110 may also send information to and receive information from computing device(s) 220. The computing device(s) 220 may comprise a computer, smartphone device, laptop, tablet or other suitable device. The computing device(s) 220 may comprise one or more processors 222 and memory 224 storing instructions (e.g. program code) which when executed by the processor(s) 222 causes the computing device(s) 220 to cooperate with the control device 110 and perform processes according to the described methods. The computing device 220 may be a computing device associated with the user, or may for example, be a computing device of the user's clinician, or other clinician.

The computing device(s) 220 comprises a network interface 226 to facilitate communication with the components of the communications network 210. The computer device(s) 220 may also comprise a user interface 228 to allow the user to interact with a cognitive performance monitoring application 225 and other applications or functionality provided by the computing device(s) 220.

Memory 224 comprises the cognitive performance monitoring or cognitive assessment application 225. In some embodiments, the cognitive performance monitoring application 225, when executed by processor(s) 222, enables the computing device 220 to cooperate with the control system 110 to monitor the cognitive performance of the subject as the subject undergoes treatment using the apparatus 100 or the subject is monitored using the apparatus 100, and in some embodiments, to control the operation of the control device 110. The cognitive performance monitoring application 225 be downloaded or otherwise deployed on the subject's computing device 220.

In some embodiments, the cognitive performance monitoring application 225 may be arranged to receive and store data from the control device 110 about the progress of the user, which may be displayed to the user and/or provided to server 230, or another computing device 220. In some embodiments, the cognitive performance monitoring application 225 may be configured to receive and track behavioural data, such as sleep data, mindfulness activities, exercise, diet and/or other information that may have an impact on the cognitive performance of the individual. For example, the user may input such information via the user interface 228 or the cognitive performance monitoring application 225 may be configured to cooperate with other applications running on the computing device 220, such as a pedometer, or on other user devices, such as a smart watch. An authorised clinician may be provided with access to the cognitive performance monitoring application 225 deployed on the user's computing device 220, or to a file associated with the user stored in database 240 or server 230.

In some embodiments, the cognitive performance monitoring application 225 may comprise one or more games, tasks, activities or applications that may be performed by the user when undertaking treatment using the apparatus 100 to activate specific regions of the brain with a view to targeting the effect of stimulation to the regions of the brain activated by those tasks and monitor the resulting effect of stimulation using the apparatus 100. In some embodiments, the tasks of the cognitive performance monitoring application 225 may be performed by the user to activate specific regions of the brain (without delivering electrical stimulation to the brain) with a view to monitoring or measuring the resulting neural activity using the apparatus 100. For example, such paired activities may focus on tasks involving working memory, attention, and/or impulse control. In some embodiments, the application 225 further comprises a series of task-based activities and/or psychometric tests to be completed, independent of, or during an electrical stimulation session. This may provide a beneficial effect of a standardised baseline set of activities, allowing for more consistent analysis of the brain activity of the user 115, and may offer a consistent baseline on which models of the control device 110 or computing device 220 may be trained. The cognitive performance monitoring application 225 may also provide clinicians and/or users with feedback on the user's performance over time, which may be used in determining treatment options, plans and/or operating parameters of the control device 110. Having user's track their performance and ideally improvements over time, can motivate and encourage them to engage with and adhere to the treatment.

The cognitive performance monitoring application 225 may receive inputs from the user via the user interface 228. The input may relate to instructions for performing the paired tasks. The input may relate to instructions for operation of the control device 110, including sending/receiving instructions to and from the control device 110. The computing device 220 may be further configured to display information to the user about the apparatus 100, including data associated with the one or more electrodes 120 or the one or more optical sensors 130, data from the control device 110, or data from the server 230 and database 240.

In some embodiments, the cognitive performance monitoring application 225 may be responsive to user input, for example, via user interface 228, to transmit an instruction to activate or start the control device 110 and begin the delivery of the stimulation to the electrodes and/or the monitoring of the effect of the stimulation on the regions being targeted. Similarly, the cognitive performance monitoring application 225 may pause or deactivate the electrical stimulation sessions and/or the recording of sensor data by sending instructions to the control device 110. In other words, the cognitive performance monitoring application 225 may be used to control the operation of the control device 110 of the apparatus 100. In some embodiments, the cognitive performance monitoring application 225 may be configured to transmit task data to the control device 110 or to the server 230. In some embodiments, the control device 110 or server 230 may receive the task data from the control device 110. In some embodiments, the control device 110, the server 230 and/or the computing device 220 may receive supplemental task data from elsewhere, for example, via user input using user interface 360. The task data may be indicative of the type of task to be performed by the user during the session or while undergoing the treatment. The control device 110, computing device 220 or server 230 may use the task data to determine one or more stimulation parameter value(s), and/or to determine the activity measure. For example, stimulation required and thresholds and/or features for determining activity measures and/or stimulation parameter value(s) may vary from task to task. In some embodiments, the task data may comprise one or more scores achieved by the user in performing the task and which may be used by the control device 110 in combination with the measured data to infer behavioural progress of the subject. For example, the scores may be indicative of the accuracy and/or reaction times associate with performing the task. In other embodiments, recorded data and/or activity measures and task data including scores may be transmitted to the server 230 (such as a remote server) for processing to infer behavioural progress of the subject.

FIG. 3 depicts a schematic diagram of a system 300 for controlling the delivery of transcranial electrical stimulation and/or monitoring of brain activity, according to some embodiments. In this figure, the functional components of the control device 110 of FIG. 2 are depicted in greater detail. However, it will be appreciated that in other embodiments, one or more of the functional components of the control device 110 may be deployed on other devices or systems, such as the computing device 220 and/or the server 230.

The control device 110 may be housed within a housing 112. The housing 112 may further comprise the optical sensor module 340 and/or the electrical stimulation source 350. In some embodiments, the electrical stimulation source 350 and/or the optical sensor module 340 may be external to the housing 112. The housing 112 may further comprise a human machine interface (HMI) 355 configured to switch the electrical stimulation and/or optical sensing supplied to a user 115 on or off manually. In some embodiments the HMI 355 may be configured to switch the system 300 between an active state, a passive state, and a powered off state.

The control device 110 comprises one or more processors 310 and memory 320 storing instructions (e.g. program code) which when executed by the processor(s) 310 causes the control device 110 to function according to the described methods. The processor(s) 310 may comprise one or more microprocessors, central processing units (CPUs), graphical/graphics processing units (GPUs), application specific instruction set processors (ASIPs), application specific integrated circuits (ASICs), field programmable gate arrays (FPGAs) or other processors capable of reading and executing instruction code. Processor 310 may include additional processing circuitry. For example, processor 310 may include multiple processing chips, a digital signal processor (DSP), analog-to digital or digital-to analog conversion circuitry, or other circuitry or processing chips that have processing capability to perform the functions described herein. Processor 310 may execute all processing functions described herein locally on control device 110 or may execute some processing functions locally and outsource other processing functions to another processing system, such as server 230 or the computing device 220.

Memory 320 may comprise one or more volatile or non-volatile memory types. For example, memory 320 may comprise one or more of random access memory (RAM), read-only memory (ROM), electrically erasable programmable read-only memory (EEPROM) or flash memory. Memory 320 is configured to store program code accessible by the processor(s) 310. The program code comprises executable program code modules. In other words, memory 320 is configured to store executable code modules configured to be executable by the processor(s) 310. The executable code modules, when executed by the processor(s) 310 cause the control device 110 to perform certain functionality, as described in more detail below.

Memory 320 may comprise a feature extraction module 322, an analysis engine 324 and/or a stimulation control module 326.

The feature extraction module 322 comprises executable program code, which when executed by the processor(s) 310, causes the control device 110 to identify or extract characteristics or features of signals or data recorded by and received from the optical sensor module 340. The signals measured or calculated by the optical sensor module 340 or control device 110 may include changes in Hbo and Hbr, the Hbo and Hbr curves, as well as combinations of them, including total haemoglobin ThB (ThB=Hbo+Hbr).

The features may be characteristic or indicative of biomarkers associated with cognitive function or performance or cortical activity. In some embodiments, the feature extraction module 322 is configured to determine one or more of:
- a peak amplitude;
- a peak width;
- a number of peaks, for example, for a bimodal signal;
- a slope of a portion of the signal;
- an autoregressive moving average (ARMA) coefficient;
- a rise time of an amplitude or slope;
- a baseline activity;
- a baseline trend;
- a number of zero crossings;
- a haemoglobin value, such as the HbO and HbR correlation;
- rise time for a peak;
- a ratio of HbO to HbR for amplitude, width, slope, or other characteristics;
- a change in total blood volume;
- signal morphology; and
- area under the curve.

In other embodiments, other signal features or characteristics may be extracted. The feature extraction module 322 provides the extracted features as inputs to the analysis engine 324. In some embodiments, the feature extraction module 322 may be deployed on the server 230 and/or the computing device 220.

In some embodiments, the feature(s) comprise or are indicative of functional connectivity between pairs of channels of the apparatus 100—i.e., the statistical dependence and/or similarity between pairs of data from neighbouring or distinct regions of the brain. In some embodiments, the feature(s) comprise or are indicative of statistics applied to data derived from one or more channels.

For example, the feature(s) used by the activity determination model 328 to determine an activity measure may be extracted from sensor data acquired from a subject's left lateral prefrontal cortex, the medial prefrontal cortex, and/or a boundary between medial prefrontal and left lateral prefrontal. The feature(s) used by the symptom severity or progress determination model 327 to determine an overall ADHD symptom severity measure may be extracted from sensor data acquired from a subject's right lateral prefrontal cortex. The reaction time and omission error metric from the task data may also be used to determine input features to the symptom severity or progress determination model 327 to determine an overall ADHD symptom severity measure.

The feature(s) used by the symptom severity or progress determination model 327 to determine a primary ADHD core symptom score may be extracted from sensor data acquired from a subject's right lateral prefrontal cortex.

The feature(s) used by the symptom severity or progress determination model 327 to determine an inattention score may be extracted from sensor data acquired from a subject's medial prefrontal cortex, and/or a bordering region of the medial prefrontal cortex and the left lateral prefrontal cortex. The reaction time and omission error metrics from the task data may also be used to determine input features to the symptom severity or progress determination model 327 to determine an inattention severity measure.

The feature(s) used by the symptom severity or progress determination model 327 to determine a hyperactivity score may be extracted from sensor data acquired from a subject's right lateral prefrontal cortex, the left lateral prefrontal cortex, and/or the region overlapping with the left lateral prefrontal cortex and the medial prefrontal cortex.

The feature(s) used by the symptom severity or progress determination model 327 to determine an impulsivity severity measure may be extracted from sensor data acquired from a subject's medial prefrontal cortex, and/or the medial prefrontal cortex toward, overlapping or bordering on the subject's right lateral prefrontal cortex. Feature values based on reaction time metrics of the task data may be provided to the symptom severity and/or progress determination model to determine the impulsivity severity measure.

The analysis engine 324 may comprise executable program code, which when executed by the control device 110 is configured to determine an activity measure indicative of the user or subject's measured brain activity at the targeted region based on the cerebral haemodynamic response(s) measured by the optical sensor module 340. The analysis engine 324 may comprise executable program code, which when executed by the control device 110 is configured to determine a symptom severity measure indicative of the symptom of the neurological condition or a progress measure indicative of progress the subject is making in treating symptoms of neurological condition based on measured brain activity at the targeted region based on the cerebral haemodynamic response(s) measured by the optical sensor module 340 and task data, as may be collected by the cognitive performance monitoring application 225. In other words, the analysis engine 324 infers executive function performance from recorded fNIRS data, and in some embodiments, also from task data.

In some embodiments, feature(s) detected from a plurality of the sensors 130 may be analysed in combination, or with respect to one another, to determine a pattern of behaviour or activity. For example, if successive sensors or channels show a positive amplitude, but the sensors surrounding those positive sensors show a distinctly negative amplitude, that could a biomarker indicative of oxygenated blood moving from one area, to another (for example, such that is described in the "blood stealing hypothesis").

In some embodiments, the analysis engine 324 comprises a univariate or multivariate activity determination model 328. The activity determination model 328 may be a machine learning model. The activity determination model 328 may be configured to receive as inputs, feature(s) extracted from the sensor signal(s) and to provide as an output, the activity measure. For example, the activity measure may be indicative of whether the targeted region of the brain is exhibiting sufficient activity levels, and in addition, whether or not sufficient stimulation has been delivered to the subject to achieve a desired level of activity at the target area. This may involve comparing the activity measure to a threshold value. In other embodiments, the activity measure may be a confidence score associated with whether or not sufficient activity is occurring in the targeted region. In some embodiments, the activity determination model 328 may employ techniques such as general linear model analysis, beta value or regression analysis, logistic regression, linear regression, neural networks, and the comparison of activity in one channel of signals to another.

In some embodiments, the analysis engine 324 provides the activity measure as an input to the stimulation control module 326. The stimulation control module 326 may employ a univariate or multivariate model(s) 329. The stimulation control module 326 may be a machine learning model. The stimulation control module 326 may be configured to receive, as an input, the activity measure, and to provide as an output, stimulation parameter value(s). The stimulation parameter(s) may be simply an on/off parameter value, or may include values for parameters such as frequency, duration, amplitude etc.

In some embodiments, the analysis engine 324 or the activity determination model 328 of the analysis engine 324 may be deployed on the server 230 and/or the computing device 220. In such embodiments, the server 230 and/or on the computing device 220 may be configured to determine the activity measure and provide the activity measure to control device 110, which may then determine the stimulation parameter value(s). In some embodiments, the stimulation control module 326 may be deployed on the server 230 and/or the computing device 220 and the server 230 and/or the computing device 220 may be configured to provide the stimulation parameter value(s) to the control device 110 to control the stimulation being delivered to the subject.

In some embodiments, the control device 110 transmits stimulation instructions comprising the stimulation parameter(s) to the electrical stimulation source 350 to adjust the stimulation being delivered to the patient, for example, to cause cessation of the stimulation, or by adjusting characteristic(s) of the stimulation signal.

In some embodiments, the analysis engine 324 comprises a univariate or multivariate symptom severity or progress determination model 327. The symptom severity determination model 327 or progress determination model 327 may be a machine learning model. The symptom severity or progress determination model 327 may be configured to receive as inputs, one or more characteristics or feature(s) extracted from the recorded data or the measured data, and one or more scores associated with respective tasks performed by the subject while the data was recorded, and to provide as an output, a symptom severity measure or a progress measure. For example, the scores may be indicative of the accuracy and/or reaction times associated with performing the task. Multiple sets of data, each comprising sensor data and related score(s) for a particular task, may be used to determine the symptom severity measure or progress measure. For example, the sets of data may span a particular time period. In some embodiments, a baseline or initial set of data is determined and progress is assessed against that baseline. In some embodiments, a determined progress measure is determined relative to a most recently determined progress measure or symptom severity measure. In some embodiments, the symptom severity or progress determination model 327 may comprise one or more sub-models configured to infer behavioural progress with respect to a specific task. In other embodiments, the symptom severity or progress determination model 327 may be configured to receive scores associated with a plurality of respective tests as inputs. The symptom severity or progress determination model 327 may be configured to provide a symptom severity indication or value associated with one or more symptoms. For example, where the symptom severity or progress determination model 327 is configured to determine the symptom severity or progress of characteristics or behaviours associated with ADHD, the symptom severity or progress determination model 327 may provide, as an output, values for one or more of: an overall ADHD rating scale score, an ADHD core symptom score, an inattention score, a hyperactivity score, and an impulsivity score.

In some embodiments, the symptom severity or determination model 327 may be deployed on a server 230, such as a remote server or a computing device 220 such as a smartphone, and the server 230 and/or on the computing device 220 may be configured to determine the symptom severity or progress measure. For example, the server 230 and/or on the computing device 220 may be configured to receive or determine the task data, including for example, the scores, and the recorded or measured data from the control device 110 or feature extraction module 322 and/or the cognitive performance monitoring application 225.

The system 300 comprises a network interface or communication module 330 to facilitate communications with components of the system 300 across the network 210, such as the computing device(s) 220, database 240 and/or other systems or servers 230. The communications module 330 may comprise a combination of network interface hardware and network interface software suitable for establishing, maintaining and facilitating communication over a relevant communication channel. The communications module 330 may comprise a wireless Ethernet interface, SIM card module, Bluetooth connection, or other appropriate wireless adapter allowing wireless communication over network 210. For example, in some embodiments, the control device 110 and the computing device 220 are arranged to communicate with one another via Bluetooth. In some embodiments, a wired communication means is used.

For example, in some embodiments, the system and/or control device 110 may be a wireless system or device, such as a wireless headset. In such embodiments, components of the system 300 and/or control device 110 may be selected or configured specifically for low power operation, to allow for extended usage without requiring relatively larger batteries, for example. This may allow for the overall device or system size to be reduced, which may be cheaper to manufacture.

The activity determination model 328 and/or the symptom severity or progress determination model 327 may be based on models such as logistic regression, linear regression and neural networks, for example, which have been trained to infer activity measures from the fNIRS data. In some embodiments, the activity determination model 328 and/or the symptom severity or progress determination model 327 are trained using a supervised machine learning approach using training dataset, which has been divided into a training data subset and a testing data subset. The training dataset comprises data for a plurality of individuals who completed a clinically relevant neurobehavioural disorder rating scale questionnaire, and performed psychometric tests measuring executive function performance while the optical sensor module 340 recorded the fNIRS data. Accordingly, the training data comprises example data for each of a plurality of individuals. The example data includes results of psychometric test(s), (and in some embodiments the types of tests) and the associated fNIRS data recorded while the respective test(s) were being performed.

In some embodiments, the activity determination model 328 and/or symptom severity or progress determination model 327 may be trained with the use of unsupervised machine learning to help undercover any additional relationships between the optical signal data, task data (e.g. psychometric test results), and/or stimulation parameters. The activity determination model 328 and/or symptom severity or progress determination model 327 may also form the basis of feedback provided to medical professionals in the treating of the user 115. In this way, consistent feedback may be provided to the clinician to assist in assessing progress of the user and/or to make treatment decisions, and in some embodiments, to reconfigure the control device 110. In some embodiments, the activity determination model 328 may comprises one or more sub-models configured to infer brain activity with respect to a specific task. In other embodiments, the activity determination model 328 may be configured to receive scores associated with a plurality of respective tests as inputs.

In some embodiments, the stimulation control model 329 may be determined or trained based on an assessment or evaluation of the efficacy of different stimulation parameters experimentally. For example, the stimulation control model 329 may comprise models such as logistic regression, linear regression and/or neural networks trained using a supervised machine learning approach. In some embodiments, a similar psychometric test(s) may be performed on participants, with and without stimulation being applied, and observing and recording statistical changes in performance. By simulating many different stimulation configurations and experimentally evaluating the most promising ones, a decision will be made on the most appropriate montage and stimulation parameters (amplitude and type/frequency of stimulation, for example).

In some embodiments, one or more of the stimulation control module 326, model 329, activity determination model 328, symptom severity (or) progress determination model 327, and feature extraction module may be located within memory 224 of the computing device 220 and be executed by the processor 222 of computing device 220.

FIG. 4 is an example of the apparatus 100, according to some embodiments. The apparatus 100 comprises a front band 405, configured for placement at the front of the head of the user 115, and a rear band 415 with a back electrode mount 410, configured for placement at the back of the head of the user 115. The front band 405 may be pivoted about a point 420 as depicted in FIG. 5, and the back band may be adjustable to accommodate different head sizes of a user 115. The back piece 415 may be configured to house or support the control device 110, thereby acting as the housing 112 in FIG. 2. The return electrode 123 may also be disposed on the back piece 415. In some embodiments, back piece 410 may be omitted. Front band 405 may further comprise an elongate array 700, as depicted in FIG. 7, arranged to carry or mount the electrode(s) 120, which in this embodiments are disposed in a spaced apart manner along a length of the array 700. The array 700 may carry or mount the optical sensor(s) 130 (or optical sensor components), and more specifically, the light emitter 130A and the detectors 130B. In this example, each optical sensor 130 comprises a light emitter 130A and two corresponding light detectors 130B. The electrode(s) 120, the light emitters 130A and light detectors 103B are arranged or placed ipsilaterally on the inner surface of the array 700, such that they make contact with the user's head when the apparatus is worn by the user. In such an embodiment, the front band 405 holds the array 700 in place against the front of the head of a user 115 and is configured to more easily provide consistent electrical stimulation to the user 115, and to receive more consistent optical responses from the user 115. Accordingly, the fixed locations on the array for the electrodes 120 and optical sensors 130, when placed on the head of a user 115 in this embodiment, allows the same regions to be stimulated over multiple stimulation sessions. This has the beneficial effect of achieving a high degree of consistency in applying electrical stimulation to desired regions of the head, and to ensure accuracy of measured optical signals—which in turn have beneficial effects on the accuracy of the determination of beneficial effects by the analysis engine 324. In some embodiments, the control device 110 may instruct the electrical stimulation source 350 to provide electrical stimulation to select or specific electrode(s) 120, or specific combination of electrode(s) 120. In other embodiments, the control device 110 is configured to cause the electrical stimulation source 350 to provide electrical stimulation to all electrode(s) in the array 700.

In some embodiments, a different number of electrodes 120 and/or optical sensors 130 may be provided, such as a high number or a lower number, which may depend on the size of the array 700 on the front band 405.

Figure 12:
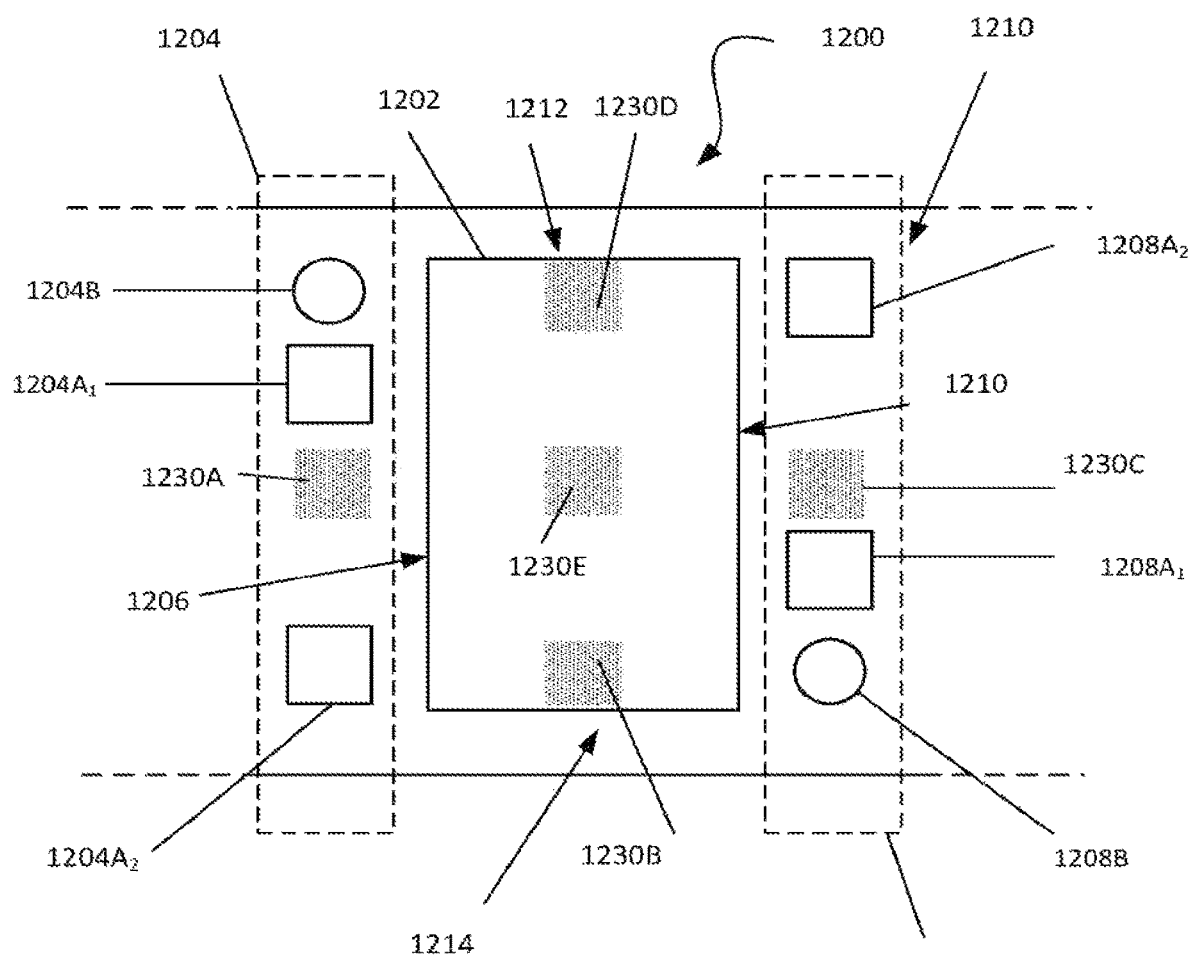
FIG. 12 depicts an electrode and optical sensor mount array of the apparatus of FIG. 1, depicting sensing regions, according to some embodiments.

FIG. 12 depicts a section 1200 of the array 700. The section 1200 comprises an electrode 1202 with a first optical sensor 1204 disposed on a first side 1206 of the electrode 1202 and a second optical sensor 1208 disposed on a second side 1210 of the electrode 1202. The first optical sensor 1204 comprises first and second light detector $1204A_1$ and $1204A_2$, and a light emitter 1204B. The second optical sensor 1208 comprises first and second light detector $1208A_1$, $1208A_2$ and a light emitter 1208B.

As illustrated, in some embodiments, the light emitter 1204B of the first optical sensor 1204 is disposed toward or at a first end 1212 of the electrode 1202 on the first side 1206 of the electrode 1202. The first light detector $1204A_1$ is disposed toward or in proximity to the first end 1212 of the electrode 1202 on the first side 1206 of the electrode 1202, and for example, in proximity to the light emitter 1204B. The second light detector $1204A_2$ of the first optical sensor 1204 is disposed toward, at or in close proximity to the second end 1214 (opposite to the first end 1212) of the electrode 1202 on the first side 1206 of the electrode 1202. In some embodiments, the second light detector $1204A_2$ is positioned closer to the first light detector $1204A_1$ than to the light emitter 1204B. In other words, the first light detector $1204A_1$ is positioned innermost of the light emitter 1204B.

As illustrated, in some embodiments, the light emitter 1208B of the second optical sensor 1208 is disposed toward, at or in proximity to the second end 1214 of the electrode 1202 on the second side 1210 of the electrode 1202. The first light detector $1208A_1$ of the second optical sensor 1208 is disposed toward or in proximity to the second end 1214 on the second side 1210 of the electrode 1202. The second light detector $1208A_2$ of the second optical sensor 1208 is disposed toward, at or in close proximity to the first end 1212. In some embodiments, the second light detector $1208A_2$ is positioned closer to the first light detector $1208A_1$ than to the light emitter 1208B. In other words, the first light detector $1208A_1$ is positioned innermost of the light emitter 1204B.

As explained above, when the apparatus 100 comprising array 700 is applied to a subject's head, the optical sensors 130 are configured to measure brain activity at a location or position of the brain of the subject that is midway, or at the midpoint between a light emitter 130A and a light detector 130B.

Referring again to FIG. 12, when stimulation is applied to the subject head via electrode 1202, the light emitter detector pair $1204A_1$ and 1204B is configured to determine or measure systemic (skin, skull, etc.) changes in blood oxygenation of the subject at a location midway between the position of the light emitter $1204A_1$ and the light detector 1204B.

Referring again to FIG. 12, when stimulation is applied to the subject head via electrode 1202, the light emitter detector pair $1204A_2$ and 1204B is configured to determine or measure brain activity of the subject at a location midway between the position of the light detector $1204A_2$ and the light emitter 1204B, location 1230A in FIG. 12. Similarly, the light emitter detector pair $1204A_2$ and 1208B is configured to determine or measure brain activity of the subject at a location midway between the position of the light detector $1204A_2$ and the light emitter 1208B, location 1230B in FIG. 12; the light emitter detector pair $1208A_2$ and 1204B is configured to determine or measure brain activity of the subject at a location midway between the position of the light detector $1208A_2$ and the light emitter 1204B, location 1230D in FIG. 12: the light emitter detector pair $1208A_2$ and 1208B is configured to determine or measure brain activity of the subject at a location midway between the position of the light detector $1208A_2$ and the light emitter 1208B, location 1230C in FIG. 12: the light emitter detector pair $1208A_1$ and 1208B is configured to determine or measure systemic (skin, skull, etc) changes in blood oxygenation of the subject at a location midway between the position of the light emitter $1208A_1$ and the light detector 1208B: the light emitter detector pair $1208A_1$ and 1204B is configured to determine or measure brain activity of the subject at a location midway between the position of the light detector $1208A_1$ and the light emitter 1204B, location 1230E in FIG. 12: the light emitter detector pair $1204A_1$ and 1204B is configured to determine or measure brain activity of the subject at a location midway between the position of the light detector $1204A_1$ and the light emitter 1204B; and the light emitter detector pair $1204A_1$ and 1208B is configured to determine or measure brain activity of the subject at a location midway between the position of the light detector $1204A_1$ and the light emitter 1208B, location 1230E in FIG. 12.

Emitter-detector pairs $1204A_2$ and 1204B, $1204A_2$ and 1208B, $1208A_2$ and 1204B, $1204A_1$ and 1208B, $1208A_1$ and 1204B, and $1208A_2$ and 1208B each form a relatively long channel. These long channels are arranged to measure brain blood oxygenation at the point mid-way between the emitter-detector pair. Emitter-detector pairs $1204A_1$ and 1204B, and $1208A_1$ and 1208B each form a relatively short channel. These short channels are arrange to measure brain blood oxygenation in the nearby scalp, or scalp region of the subject at the point mid-way between the emitter-detector pair. This information (i.e. the brain blood oxygenation in the nearby scalp) may be used by the analysis engine 324 to remove scalp information from the measurement of the long channel during data processing. By configuring the placement of the optical sensor(s) 130, that is the light emitter 130A and light detector 130B pair, relative to respective electrode(s) 120, specific sites or locations of the brain of the subject can be targeted with stimulation and associated (or responsive) brain activity measured. In some embodiments, the control device 110 is configured to determine brain activity at specific site of the subject's brain based on one or more sensor signals received from one or more light emitter and light detector pairs 130A, 130B of a respective sensor module 130. For example, in the case of a control device 110 comprising an array 700 including the section 1200 of FIG. 12, brain activity at locations in the vicinity and surrounding the site of application of stimulation to the subject (which may be the part or site of the brain of the subject directly under electrode 1202, indicated at location 1230E), as well as at the location of stimulation 1230E can be determined. In some embodiments, brain activity at the location 1230E can be determined using the emitter-detector pairs 1204B and $1208A_1$ and/or 1208B & $1204A_1$.

This arrangement provides an integrated mechanism for fNIRS recording and electrical stimulation of the brain at the same location. The apparatus 100 comprising array 700, or similar, may allow for more precise measurement and analysis of the effect of electrical stimulation of the brain using fNIRS.

In some embodiments, the location of electrode(s) 120 may be based on the EEG 10-5 system, and include positions F3-F4, FP2-F3, P3-FP2, F6-F5, AF7-AF8. However, it will be appreciated that the location of the electrode(s) 120 may include any combination of locations spanning across the line between P7-P8, FT9-FT10, F9-F10, AF7-AF8, FP1-FP2, PO3-PO4, and O1-O2. This includes the 10-5 locations between these landmarks on the same plane. The optical sensors 130 may be placed surrounding the chosen stimulation channels, to ensure close proximity to the site of electrical stimulation. In such embodiments, a different band shape and location may be used to ensure an accurate fit with the head of a user 115. In some embodiments, the adjusting of the front band 405 through the pivot point 420 allows for electrodes 120 to target the desired head regions.

The fit of the array 700 may be specifically configured to allow the placement of the optical sensors 130 at a desired distance from the user's 115 head, to ensure accurate measurements being obtained for a given user 115.

The placement of electrodes for the delivery of neural stimulation is important, as this determines the brain location that is targeted by the stimulation. The apparatus 100 may be configured to fit on or accommodate various head sizes, noting that head size varies between people, and especially between sexes. Due to variation in head sizes, the location of electrodes on a static or fixed arrangement array 700 of apparatus 100 may mean that placement of electrodes 120 (for example, the locations where the electrodes touch the forehead) may vary between individuals, which may result in variations in the results of stimulation and/or the effectiveness of the application of the stimulation.

Accordingly, in some embodiments, the front band 405 and/or array 700 of the apparatus 100 may be adjustable to allow selective placement of the electrode(s) 120 at desired locations on the head of a subject.

In some embodiments, the control device 110 may allow for software allocation of electrode locations relative to the subject's head (for example, a selection of a particular subset of electrodes 120 of the array 700), so that depending on the head size of the user, an appropriate subset of electrodes 120 may be elected for delivering stimulation to the subject.

Figure 13:
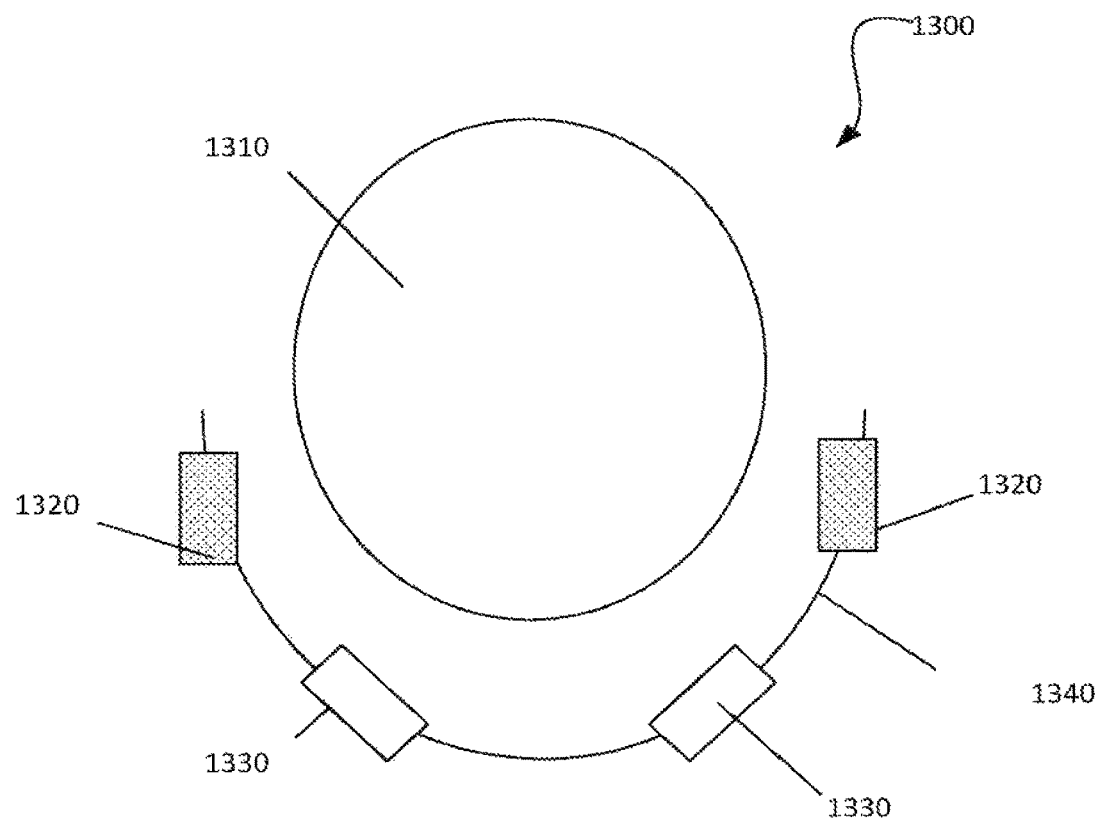
FIG. 13 depicts an overhead view of an electrode array on a user's head, according to some embodiments.
Figure 14:
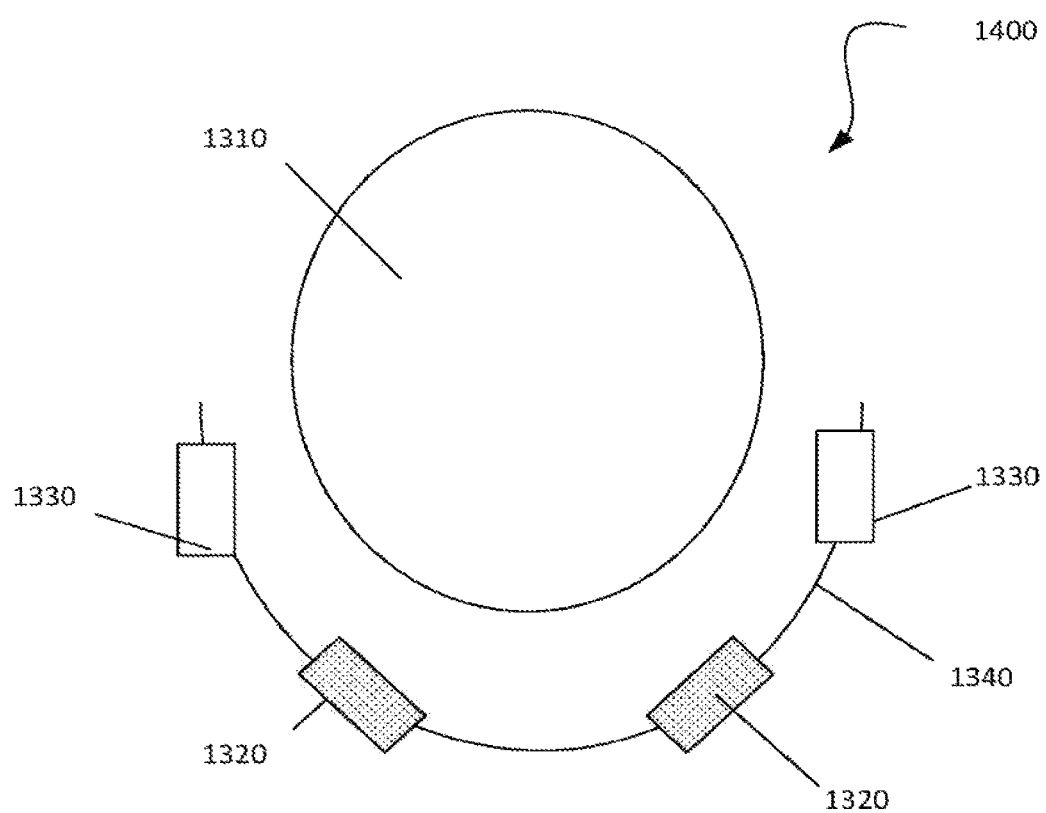
FIG. 14 depicts an overhead view of an electrode array on a user's head, according to some embodiments.

FIG. 13 depicts an overhead arrangement 1300 of array 700 positioned on a subject's head 1310. The array 700 comprises a plurality of electrodes 120, a set of which can be selectively used for delivering stimulation to the subject's head. In this example, the array 700 comprises four electrodes, the outer two of which are elected electrodes 1320, and the inner two of which are unelected electrodes 1330. This selection of electrodes 120 may accommodate or suit a subject with a relatively large head size. Similarly, FIG. 14 depicts an overhead arrangement of array 700 positioned on a subject's head 1310. The array 700 comprises a plurality of electrodes 120, a set of which can be selectively used for delivering stimulation to the subject's head. In this example, the array 700 comprises four electrodes, the outer two of which are unelected electrodes 1330, and the inner two of which are elected electrodes 132 0. This selection of electrodes 120 may accommodate or suit a subject with a relatively smaller head size.

The number of electrodes depicted are merely representative in FIG. 13 and FIG. 14. Accordingly, any number of electrodes may be disposed on array 700, such as 4, 6, or 8 electrodes, etc.

In some embodiments, the control device 110 may be configured to receive input from the subject or other user, for example, via user interface 360, to indicate which size configuration should be accommodated for, and which in turn may dictate which combination of electrodes 120 is used by the control device 110 in administering the stimulation. For example, the user interface 360 may allow a subject to select a small, medium or large head size.

In some embodiments, the control device 110 may be configured to assist in determining an appropriate selection of electrodes for a given subject by administering test stimulation delivered to the head of the subject via one or more sets of electrodes 120, and analysing a response received via respective sensor module(s) 130 to determine accurate placement of the electrodes relative to the subject's head. In some embodiments, the control device 110 may be configured to analyse the response(s) and determine the appropriateness or otherwise of the one or more sets of electrodes, and in some embodiments, to assist in determining or selecting a set of the one or more electrode sets as elected electrodes for the administering of stimulation to the subject. In some embodiments, the control device 110 may transmit the response over network 210 to the cognitive performance monitoring application 225 of the computing device 220 or to the server 230 for analysis to accurate placement of the electrodes relative to the subject's head. For example, the control device 110, the computing device 220 and/or the server 230 may be configured to analyse the response to determine if the response meets conditions associated with a strong or effective electrode placement, indicative of a properly placed array 700. In some embodiments, if the response does not meet the conditions, the control device may select another set of electrodes and again administer a test stimulation and measure the associated response with a view to the response being analysed to determine the appropriate placement of the electrodes. For example, where the analysis is performed by the computing device 220 or the server 230, this may involve the transmission of an appropriate instruction to the control device 110. In some embodiments, the cognitive performance monitoring application 225 may cause an instruction to be outputted to the subject or user, for example, using user interface 228 to direct the user to alter the placement of the array 700 on their head.

By allowing for selective election of sets of electrodes of the array 700 to accommodate different users, the control device 110 and/or apparatus 100 can be tailored for individualized stimulation for the subject, which may be particularly beneficial in an in-home environment.

In some embodiments, a facial recognition filter may be used to assist a subject in reliable or accurate placement of the array 700, and accordingly the electrodes 120 on their head. In such embodiments, the computing device 220 comprises a front-facing camera, which may be configured to allow a user to capture images of themselves. Memory 224 of the computing device 220 may comprise a positioning feedback module 227, which when executed by the processor(s) 222 causes the computing device 220 to assist the subject or user in correct placement of the array 700, and accordingly the electrodes 120 relative to their head based on captured images or image stream. The positioning feedback module 227 may include facial recognition algorithm(s) which allow for facial landmarks such as noses, eyebrows, hairline, and/or other facial features to be determined from the captured images or image stream. Such features may allow for a pose and/or structure of a user's face to be determined. The cognitive performance monitoring application 225 may also be configured to determine the position of the array 700 of the control device 110 relative to the determined facial features, or the pose of the array 700 itself. The cognitive performance monitoring application 225 may also be configured to compare a determined position of the array 700 to an ideal or target position (or range of positions), and based on the comparison, may provide feedback to the subject to direct them to reposition the array 700 with a view to achieving the target position. For example, the cognitive performance monitoring application 225 may display an indication to the user by user interface 228 to indicate the current positioning of the array and the target positioning of the array to assist the subject to achieve the desired placement. One benefit of such a positioning feedback module 227 is that it allows for more accurate and reliable placement of the apparatus 100 when used by a user, which may result in improved stimulation and data capture reliability, particularly in an in-home environment.

Figure 17:
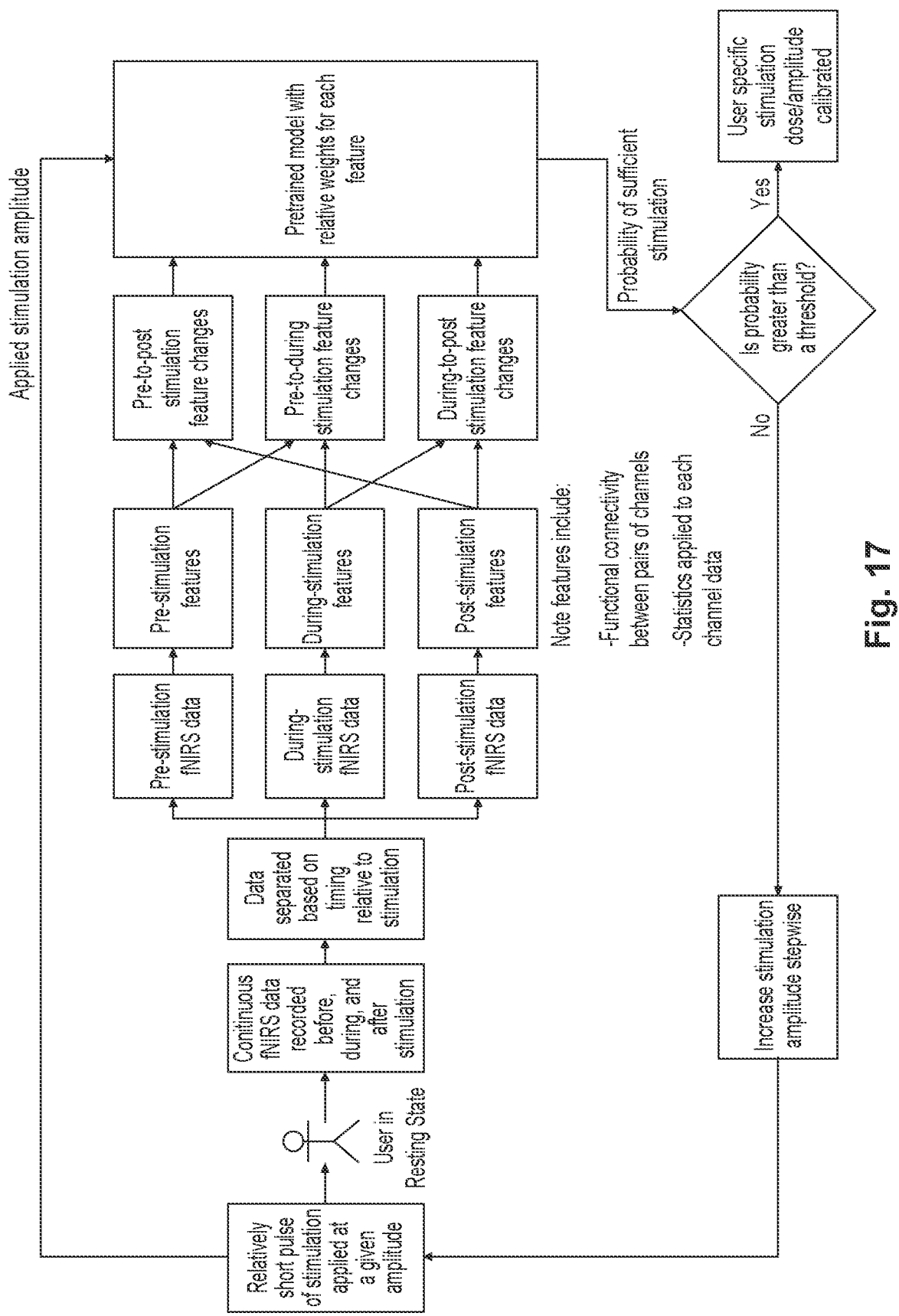
FIG. 17 is a schematic overview of a process of determining an activity measure using an activity determination model, according to some embodiments.

FIG. 8 depicts a process flow diagram for a method 800 of controlling delivery of transcranial electrical stimulation, according to some embodiments. The method may be performed by the processor(s) 310 of control device 110 executing the feature extraction module 322, the analysis engine 324, and the stimulation control module 326 of memory 320, for example. In some embodiments, the method 800 may be performed by the control device 110 and the processor 222 of computing device 220 and/or the server 230. FIG. 17 illustrates an overview of the method of 800, according to some embodiments. The user may be in a rest state while method 800 is being performed.

At 805, the control device 110 sends or transmits an instruction from the stimulation control module 326 to the electrical stimulation source 350 to cause the electrical stimulation source 350 to deliver electrical stimulation to the one or more electrodes 120. The one or more electrodes are arranged or configured for placement on the head of the user 115 to deliver transcranial electrical stimulation to targeted region of the brain of the user 115. The instructions sent by the control device 110 may comprise an instruction defining one or more of voltage, current, frequency, duration and/or offset values for the electrical signal to be applied or delivered to the electrode(s). The electrical stimulation may be applied for a preselected length of time, or until the stimulation is otherwise modified. The instruction may comprise instructions to supply tDCS, tACS, tPCS, tRNS, otDCS or random noise stimulation, or a combination thereof.

The instructions may further comprise instructions to supply relatively short pulses, wherein each pulse is characterised by an amplitude, frequency, duration and offset. Each pulse may be delivered one at a time. In other embodiments the instructions may comprise a single long pulse. In some embodiments, the initial and updated stimulation parameter value(s) for delivery of the electrical stimulation for a user may depend on the specific region of the brain to be targeted and/or the type of task or activity to be performed by the user during the session.

At 810, the control device 110 receives recorded data from one or more respective optical sensors positioned in proximity to the targeting region of the brain. The recorded data may comprise one or more signals from the respective one or more optical sensors. The signals may be indicative of the intensity of the reflected light detected by the detectors 130B of the optical sensors. In some embodiments, and as discussed above, the optical sensor module(s) 340 may be configured to create a lock-in-amplifier effect to improve the signal to noise ratio (SNR) of the detected reflected light signal.

In some embodiments, after the electrical stimulation is delivered to the one or more electrodes 120, the optical sensor module 340 records an optical response detected by the respective optical sensor(s) 130 positioned on the head of the user 115 and transmits or provides the recorded data to the control device 110. In some embodiments, the optical sensor module 340 records the data before the stimulation is applied, during or while the stimulation is being applied, and after the stimulation has been applied, for example in real time or continuously, and transmits the recorded data to the control device 110 for processing, or on-transmission, in real time. In some embodiments, the control device 110 may be configured to transmit or stream the recorded data to the server 230 or computing device 220 for processing. In some embodiments, and as discussed above, the control device 110 may be configured to sample the data at a relatively high frequency, and to down sample and/or demodulate the data before transmitting the data to the computing device, or server, for example.

At 815, the control device 110 (or in some embodiments, the computing device 220 and/or server 230) analyses the recorded data to determine an activity or effectiveness measure. The recorded data may be indicative of changes in blood oxygenation.

In some embodiments, analysing the recorded data comprises removing or lessening scalp effects from the recorded data. This may be achieved, for example, by determining one or more short channels associated with, or in the vicinity of a candidate long channel, and subtracting the signal from the short channel from the long channel. In some embodiments, all short channels signals available are subtracted from a candidate long channel. In some embodiments, the signal from only the closest physically located short channel to the candidate long channel is subtracted from the long channel signal.

In some embodiments, other signal processing techniques may be used to isolate the effect of the stimulation in signals from the measured channels. Examples include bandpass filtering the measured data, regression of accelerometer data from the signal, and/or regression of a baseline drift from the signal.

In some embodiments, the feature extraction module 322 extracts features or characteristics from the recorded data or optical response signal(s) or processed recorded data. The extracted features may correspond to characteristics or biomarkers associated with cognitive function or performance or cortical activity of the user. The extracted features may be provided as inputs to the activity determination model 328, which may provide as an output, an activity measure. In some embodiments, the activity measure comprises a transient increase in HbO.

In some embodiments, and as illustrated in FIG. 17, the control device 110 may determine from the recorded or measured sensor data, pre-stimulation sensor data (i.e. data acquired before stimulation was applied), stimulation sensor data (i.e. data acquired during the application of stimulation), and post-stimulation data (i.e. data acquired after stimulation was applied). The feature extraction module 322 may determine from each of the respective sets of pre-stimulation sensor data, stimulation sensor data, and post-stimulation data, a set of pre-stimulation features, a set of stimulation features and a set of post-stimulation features. In some embodiments, the features comprises functional connectivity between a pair of channels (two regions of the brain), and/or a statistical measure of data acquired from data channels. In some embodiments, features are extracted from sensor data acquired from pairs of optical channels around and between stimulating electrodes.

The control device 110 may determine a first set of inputs for the activity determination model 328 based on the sets of pre-stimulation features and post-stimulation features. The first set of inputs may comprising relative changes in feature values from pre-to post stimulation. The control device 110 may determine a second set of inputs for the activity determination model 328 based on the sets of pre-stimulation features and during-stimulation features. The second set of inputs may comprising relative changes in feature values from pre-to during stimulation. The control device 110 may determine a third set of inputs for the activity determination model 328 based on the sets of during-stimulation features and post-stimulation features. The third set of inputs may comprising relative changes in feature values from during-to post stimulation.

The control device 110 may be configured to provide the first, second and thirds sets of inputs, and the applied stimulation parameter (for example, the amplitude) to the activity determination model 328 to determine an activity measure, such as a probability of sufficient stimulation being applied.

In some embodiments, only two of the three sets of inputs includes a value for a specific features. For example, the first and second sets of inputs may include a value for a first feature, but the third set of inputs does not include a value for that feature.

In some embodiments, the control device 110 determines only two of the first, second and third sets of input, and the provides only the first and second sets of inputs, the first and third sets of inputs, or the first and third sets of inputs, and the and the applied stimulation parameter to the activity determination model 328 to determine an activity measure, such as a probability of sufficient stimulation being applied.

The activity measure may be indicative of whether the user's brain activity is determined to be sufficiently active, underactive, overactive, too responsive, sufficiently responsive, or under responsive. In some embodiments, the activity measure may be compared to one or more activity measure thresholds to determine whether the subject is sufficiently active, underactive, overactive, too responsive, sufficiently responsive, or under responsive.

In some embodiments, the activity measure is compared with a threshold level to determine whether the brain of the subject is unresponsive or responsive to the stimulation. At 820, the control device 110 may modify the stimulation instructions based on the determined activity measure. In some embodiments, the stimulation control module 326 determines one or more stimulation parameter values based on the determined activity measure. The stimulation instructions may comprise the stimulation parameter value(s).

At 825, the control device 110 may transmit updated stimulation instructions comprising the determined one or more stimulation parameter values to the electrical stimulation generator to cause the electrical stimulation generator to modify one or more characteristics of the stimulation.

In some embodiments, responsive to determining that the activity measure is less than a threshold value, the control device 110 increases the stimulation parameter value and reapplies the stimulation at the increased stimulation parameter value. In some embodiments, responsive to determining that the activity measure has reached the threshold value, the control device 110 determines the stimulation parameter value as a user-specific calibrated stimulation parameter.

The updated stimulation instructions may comprise an instruction to modify the frequency, amplitude, voltage, and/or current of the electrical stimulation being delivered to the electrode(s) 120. In embodiments, where an activity measure is indicative of sufficient stimulations having been applied, and for example, a change in the user's 115 brain activity corresponding to a desired effect on the symptoms of neurological conditions, for example, the symptoms of ADHD, the stimulation control module 326 may modify the electrical stimulation by ceasing the delivery of the stimulation, i.e. the stimulation parameter value(s) may include a zero or other indicator for ceasing the stimulation. In some embodiments, the stimulation parameter value(s) generated by the stimulation control module 326 may indicate to or instruct the electrical stimulation generator or source 350 to continue the stimulation at the existing settings for a certain time, or to modify characteristics of the electrical stimulation signal to target a region of the brain, and or to elicit a different response.

If a desired activity level is not met, the stimulation parameter value(s) generated by the stimulation control module 326 may indicate to or instruct the electrical stimulation generator or source 350 to continue delivering the current level of stimulation, increase the level of stimulation, decrease the level of stimulation, or modify the features of the stimulation being applied. The desired activity level or activity level threshold may depend on task information, such as a type and duration of a task or activity being or to be performed by the user during the session.

For example, the control device 110 may determine an average oxygenation concentration change of two micromoles in amplitude from the measured data associated with the optical signals from the respective one or more sensors 130, prior to the application of stimulation. Once the stimulation is applied, the control device 110 may determine (based on the measured data) that the subject's brain activity has increased to changes in oxygenation concentration of three micromoles in amplitude. In this example, the impact the stimulation had on the subject may be the change of 1 micromole of blood oxygenation concentration in the area measured. In some embodiments, this increase may also be accompanied by an increase in performance of a specific task, for example, an increase in accuracy and/or reaction time. The activity determination model 328 may determine that an activity measure using the amplitude of the blood oxygenation concentration, and optionally, the task score(s) achieved while undertaking a task while the sensor data was being recorded, as input(s). If the resulting activity measure meets an activity threshold, the control device 110 may determine that sufficient stimulation has been delivered and instruct the stimulation generator to continue to deliver the appropriate level of stimulation for a period of time and at a predetermined point, cease delivering the stimulation. On the other hand, if the resulting activity measure does not meet an activity threshold, the control device 110 may determine that continued stimulation (at the existing parameter values or at change parameter values) is required and may instruct the stimulation generator to maintain or modify the stimulation accordingly.

In some embodiments, the optical sensors 130 may continue to measure or monitor an optical response from a user 115 at all times during a session, regardless of whether electrical stimulation is being applied. In such embodiments, the optical sensors 130 may detect a change in the brain activity of the user 115 indicating that an electrical signal may need to be applied again, for example, the user's brain activity in the targeted region falls below a threshold activity level. Accordingly, a user 115 using the device for a period of time may activate the device to initiate a stimulation session, where the electrical stimulation is applied via electrodes 120 for a period of time until the threshold activity level is met, and wherein further electrical stimulation is applied via the electrodes 120 after the beneficial effect on the symptoms of neurological conditions, for example, the symptoms of ADHD, of the initial electrical stimulation is no longer detected.

In some embodiments, method 800 may be used to calibrate the apparatus 100 for a particular subject. For example, the determined activity measure (at 815) may be compared with a calibration threshold level to determine whether the brain of the subject is unresponsive to the stimulation. Responsive to the brain being deemed unresponsive, the control device 110 may be configured to modify the stimulation instructions based on the determined activity measure (at 820). For example, the control device 110 may be configured to transmit (at 825) updated stimulation instructions comprising determined stimulation parameter value(s) to the electrical stimulation generator to cause the electrical stimulation generator to modify one or more characteristics of the stimulation. In some embodiments, the stimulation parameter value(s) may be a fixed increase in stimulation to be applied. The activity measure may again be determined (at 815), and the stimulation instructions updated (for example, increased stimulation) until sufficient stimulation is considered to have been applied, or the electrical stimulation generator has reached a maximum safe limit. In some embodiments, once sufficient stimulation is considered to have been applied, or the electrical stimulation generator has reached a maximum safe limit, the control device may instruct the electrical stimulation generator to continue to deliver the deemed sufficient simulation for the session, to deliver the deemed sufficient simulation for particular time windows during the session or to cease delivering stimulation to the subject.

Such a calibration process may be performed at a start of a session with a subject, so that the apparatus is calibrated for the specific subject, and to take in consideration any factors which may impact or alter how well current may be being received by the subject, for example, such as skin oiliness, electrode conductivity, hair growth/thickness/style, etc, which may change from session to session.

In some embodiments, the control device 110 may be activated or initiated by activating the HMI 355 switch. In some embodiments, the control device 110 may be activated or initiated by the cognitive performance monitoring application 225 being executed by processor(s) 222 of the computing device 220. In such embodiments, the user 115 may initiate the instruction using the user interface 228 of computing device 220, while using the application 225. In some embodiments, the control device comprises a user interface 360 configured to allow the user to provide inputs to active/deactivate and/or control the operation of the control device and the system as a whole. The user interface 360 may also comprise a display or audio output to relay information about the operation of the control device 110 to the user.

In some embodiments, the control device 110 may be configured to transmit data associated with the detected brain activity 110 via communication module 330 to the computing device 220 associated with the user, or to the server 230 for processing or storage. This data may comprise metrics associated with the electrical stimulation being applied, the optical response of brain activity being detected, measured data derived from the optical response, the detection of one or more biomarkers, or other data related to the stimulation session. In some embodiments, the application 225 may store this data in memory 224 of the computing device 220, to be accessed by a user 115 and displayed on the user interface 228 of the computing device 220, for example. The application 225 may also display stimulation history, past psychometric test performance, or other information related to a stimulation session. In such embodiments, the data may be received from the control device 110, or retrieved from the database 240 over network 210.

In some embodiments, a treatment session may be instigated by the user activating the HMI switch 355 or other activation mechanism provided on the control device 110 or apparatus 100. In some embodiments, the cognitive performance monitoring application 225 may cooperate with the control device 110 to instigate commencement of a session. For example, a user or clinician may interact with the cognitive performance monitoring application 225 to start the sessions. In some embodiments, the cognitive performance monitoring application 225 transmits task data to the control device 110, to a computing device 220 associated with a clinician, for example, or to the server 230. The task data may comprise information about the type of task(s) being or to be performed by the user. The task data may comprise one or more scores achieved by the user in performing specific task(s).

In some embodiments, the task data may comprise one or more scores achieved by the user in performing the task and which may be used by the control device 110 in combination with the measured data to infer behavioural progress of the subject. In other embodiments, recorded data and/or activity measures and task data including scores may be transmitted to a server, such as a remote server, for processing to infer behavioural progress of the subject.

Figure 10:
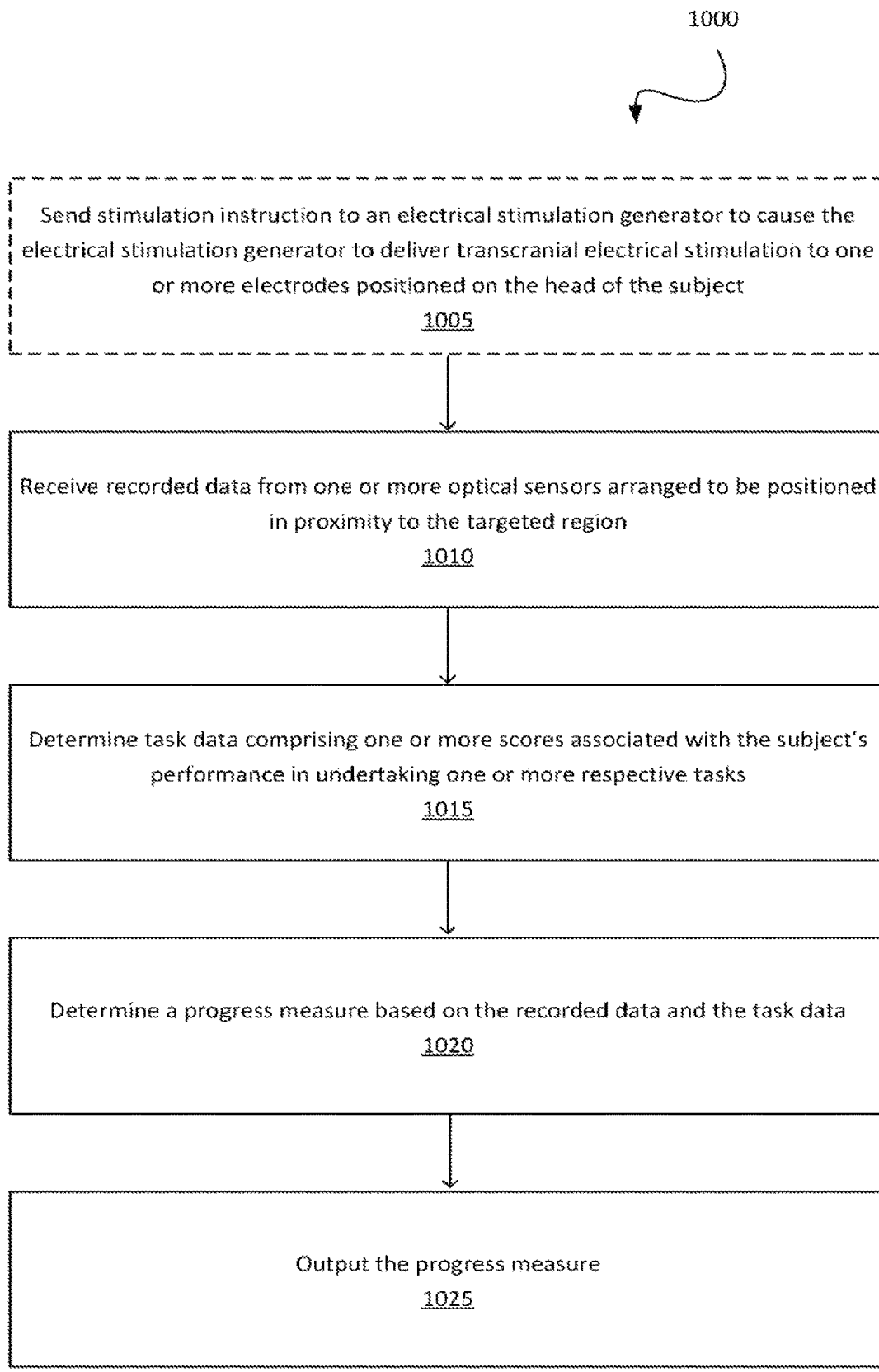
FIG. 10 depicts a process flow of a method of inferring behavioural progress of a subject undergoing treatment for one or more symptoms of a neurological condition, according to some embodiments.
Figure 18:
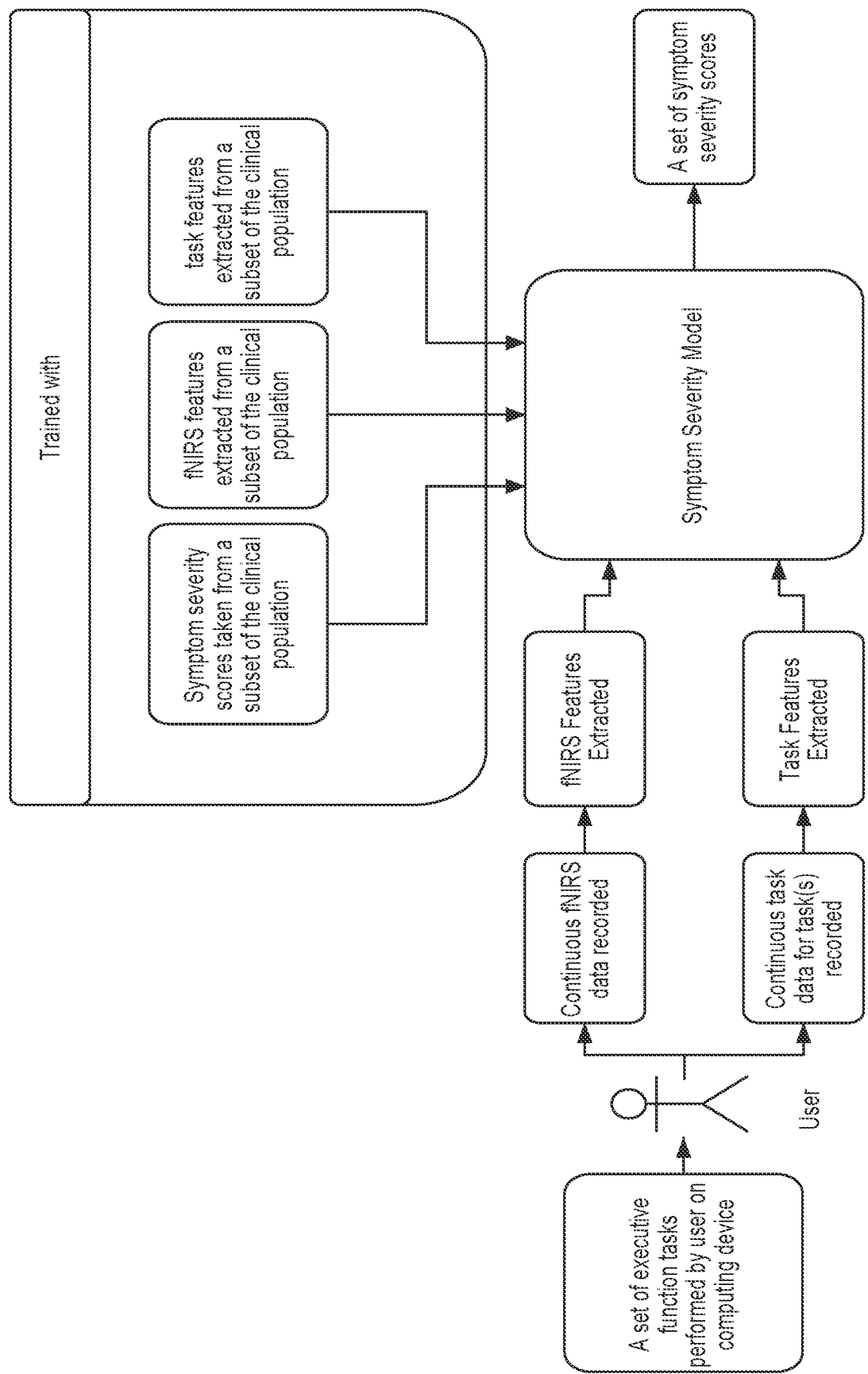
FIG. 18 is a schematic overview of a process of determining a symptom severity or progress measure using a symptom severity or progress determination model, according to some embodiments.

FIG. 10 depicts a process flow diagram of a method 1000 of inferring symptom severity and/or behavioural progress of a subject undergoing treatment for one or more symptoms of a neurological condition, according to some embodiments. In some embodiments, the method 1000 may be performed by the control device 110. In other embodiments, the method 1000 may be performed by the control device 110 in conjunction with a server 230 and/or computing device 220. FIG. 18 illustrates an overview of the method of 1000, according to some embodiments.

At 1005, the control device 110 may send or transmit an instruction to the stimulation control module 322 to cause the stimulation control module 322 to cause the electrical stimulation source 350 to deliver electrical stimulation to the one or more electrodes 120. The one or more electrodes 120 are arranged or configured for placement on the head of the user 115, to deliver transcranial electrical stimulation to targeted region of the brain of the user 115. The instructions sent by the control device 110 may comprise an instruction defining one or more of voltage, current, frequency, duration and/or offset values for the electrical signal to be applied or delivered to the electrode(s). The electrical stimulation may be applied for a preselected length of time, or until the stimulation is otherwise modified. The instruction may comprise instructions to supply tDCS stimulation, tACS stimulation, or random noise stimulation, or a combination thereof. As discussed above with reference to process 800, the instructions may comprise instructions to supply short pulses, or longer pulses. However, in some embodiments of method 1000, it is not necessary to deliver electrical stimulation to the subject, and the symptom severity and/or progress measure may be determined based on task data and sensor data alone.

At 1010, the control device 110 receives or determines recorded data from one or more respective optical sensors positioned in proximity to the targeting region of the brain. The recorded data may comprise one or more signals from the respective one or more optical sensors. The signals may be indicative of the intensity of the reflected light detected by the detectors 130B of the optical sensors. The recorded data may be recorded in the case where no stimulation has been applied (i.e. without any stimulation being applied), after the stimulation has been applied, or concurrently while the stimulation is being applied. In some embodiments, and as discussed above, the optical sensor module(s) 340 may be configured to create a lock-in-amplifier effect to improve the signal to noise ratio (SNR) of the detected reflected light signal.

At 1015, the control device 110, computing device 220 and/or server 230 determines task data. For example, the task data may be determined by the cognitive performance monitoring application 225. The task data may comprise one or more scores associated with the user's performance in undertaking or participating in one or more respective tasks. For example, suitable types of tasks include psychometric tasks or tests measuring executive function performance such as working memory, impulse control, cognitive flexibility and include tasks such as the stroop task, the wisconsin card sorting task, corsi blocking test, go-no-go task, continuous performance tasks and n back tasks, etc. The psychometric tasks or tests may be modified or gamified versions of the standard tests. In some embodiments, the task data is determined substantially simultaneously with the recorded data from one or more respective optical sensors (1005).

In some embodiments, the task data may comprise scores or metrics for one or more behavioural or characteristic symptoms, such as accuracy, reaction time, omission errors and/or commission errors. The system may determine task feature values based on the metrics of the task data. The task feature values may be statistical measures of the metrics, such as mean and/or standard deviation values of accuracy, reaction time, omission errors and/or commission errors.

In some embodiments, feature values derived from the task data metrics for reaction time may be used by the symptom severity and/or progress determination model 328 to determine a primary ADHD core symptom score or measure, an inattention severity score, impulsivity severity score, and/or a hyperactivity severity score.

At 1020, the control device 110, computing device 220 or server 230 determines a symptom severity or progress measure based on the recorded data and the task data. In embodiments where the server 230 or computing device 220 determines the symptom severity or progress measure, the respective server 230 or computing device 220 may be configured to determine or receive the recorded data from the control device 110. In some embodiments, the control device 110 may be configured to transmit or stream the recorded data to the server 230 or computing device 220. In some embodiments, and as discussed above, the control device 110 may be configured to sample the data at a relatively high frequency, and accordingly to down sample and/or demodulate the data before transmitting the data to the computing device, or server, for example.

The symptom severity and/or progress measure may comprise one or more scores for respective one or more behaviours or characteristics of a neurobehavioural disorders, such as ADHD. For example, the symptom severity or progress determination model 238 may be configured to provide scores for one or more of: (i) an overall ADHD rating scale score, (ii) an ADHD core symptom score, (iii) an inattention score, (iv) a hyperactivity score, and (v) an impulsivity score. In such an example, the symptom severity or progress determination model 238 may have been trained using labelled data task and sensor data, labelled with scores determined from an ADHD rating scale questionnaire. For example, a clinical population may have been asked to fill out a standard ADHD rating scale questionnaire which can be used to determine score for a plurality of ADHD symptoms, such as i) an overall ADHD rating scale score, (ii) an ADHD core symptom score, (iii) an inattention score, (iv) a hyperactivity score, and (v) an impulsivity score. Task data and associated sensor data was determined for the clinical population, and labelled as per the determined score for the associated participant. The task data, sensor data and labels were then used to train the symptom severity or progress determination model 238. Accordingly, the symptom severity or progress determination model 238 can be used as an automated symptom severity or progress measuring or monitoring tool for measuring or monitoring neurobehavioural disorders.

Figure 11:
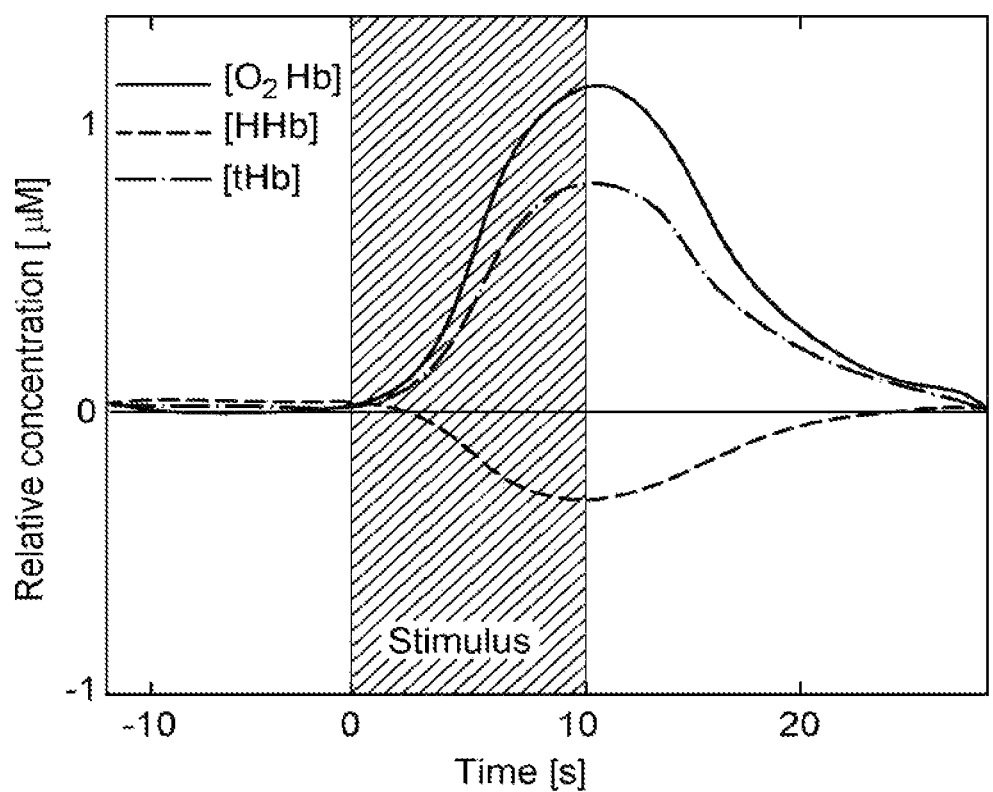
FIG. 11 is an example plot of oxygenated haemoglobin (HbO), deoxygenated haemoglobin (HbR) and total haemoglobin (ThB) concentrations derived from optical signals.

In some embodiments, the control device 110, server 230 or computing device 220 analyses the recorded data comprising the intensity signals to determine measured data. For example, the measured data may include the recorded data, and/or data derived from the recorded data, including one or more of: (i) an oxygenated haemoglobin (HbO) concentration; (ii) a deoxygenated haemoglobin (HbR) concentration; and a total haemoglobin (HbR) concentration. Example plots of HbO, HbR and HbR concentrations are illustrated in FIG. 11.

In some embodiments, the control device 110 is configured to receive sensor data from a plurality of channels, each channel corresponding to an emitter-detector pair of the optical sensors 130. As discussed above, one or more of the channels are relatively short channels, wherein the emitter is disposed in proximity to the respective detector, and one or more of the channels are relatively long channels, wherein the emitter is disposed at a relatively greater distance from the respective detector.

The long channels are configured to measure brain blood oxygenation at the point mid-way between a respective emitter-detector pair. The short channels are configured to measure brain blood oxygenation in the nearby scalp, or scalp region of the subject at the point mid-way between the emitter-detector pair. In some embodiments, only signals from the long channels are used.

In some embodiments, the control device 110, computing device 220 or server 230 is configured to screen for useful biological information being provided by the optical sensors 130. For example, the control device 110, computing device 220 or server 230 may be configured to determine whether the signals from the respective channels are of a sufficient quality. Channels determined as being ineffective at deriving useful information and/or of insufficient quality (i.e. "bad" channels) may be excluded from further analysis. In some embodiments, a quality measure indicative of a quality of each detector channel of the optical sensor(s) is determined, and responsive to the quality measure falling below a quality threshold, sensor data from the respective detector channel is excluded or ignored when determining the symptom severity or progress measure.

In some embodiments, a scalp coupling index (SCI) is determined for each of the channels. The SCI is a measure of the quality of a signal for a channel over a specific measurement duration. Responsive to the SCI falling below a threshold SCI value, the control device 110, computing device 220 or server 230 may be configured to determine that the respective channel is "bad" and exclude measurements from that channel for further analysis. In some embodiments, the control device 110, computing device 220 or server 230 may be configured to determine detector saturation. For example, this may be determined by detecting if voltage measurements fall outside of an acceptable range, such as −1.2V to 1.2V, for example. Responsive to the detector saturation being determined, the control device 110, computing device 220 or server 230 may be configured to determine that the respective channel is "bad" and exclude measurements from that channel for further analysis. In some embodiments, the control device 110, computing device 220 or server 230 may perform motion artefact correction on signals received from the channels to reduce motion artifacts. For example, such motion artefact correction may be configured to model motions using spline interpolation and subtract them from the respective signals. In some embodiments, a Wavelet based method is used. Further details on appropriate spline interpolation and Wavelet based methods can be found in the papers "How to detect and reduce movement artifacts in near-infrared imaging using moving standard deviation and spline interpolation", by Scholkamm et al (https://pubmed.ncbi.nlm.nih.gov/20308772/) and "Wavelet-based motion artifact removal for functional near-infrared spectroscopy", by Molavi et al, (https://iopscience.iop.org/article/10.1088/0967-3334/33/2/259/meta?casa_token=sIIgbEC3gYQAAAAA:gbJBtl-KCd_xpeG2oKUflninh5BHdGFR7UqQWmmj NighCDwWTpWLx7j9NI99HboeTw5zosE80A), both of which are incorporated herein by reference in their entirety.

In some embodiments, the control device 110, computing device 220 or server 230 may perform band pass filtering on the plurality of channels to remove irrelevant information.

In some embodiments, the control device 110, computing device 220 or server 230 may further process the information form the channels to remove other artifacts, such as known artifacts, from the recorded data, for example, to increase, or maximise the prominence of the hemodynamic response in the observed data. These may be achieved by performing a regression with a polynomial drift, short channel data, and accelerometer data. For example, the apparatus 100 and/or control device 110 may comprise an accelerometer (not shown) for capturing accelerometer data. Polynomial drift may be calculated by fitting a polynomial to the data and regression may involve quantifying how much of each time series (e.g. short channel, accelerometer, polynomial drift) contributes to the measured long channel data and then subtracting it.

The control device 110, computing device 220 or server 230 may be configured to separate the sensor data from each channel into sensor data associated with when the subject was at rest, or not performing a task (data under rest conditions), and sensor data associated with when the subject was performing a task (data under task conditions).

This may be achieved by considering time stamps associated with the data. For example, in some embodiments, the task data may comprise one or more timestamps associated with the subject performing respective one or more actions associated with the task (for example, task related timestamp(s)). The sensor data may comprise time series data or time stamped data. The control device 110 (or server 230 or computing device 220) may be configured to determine the symptom severity or progress measure by associating one or more subsets of the sensor data with respective task data based on timing. In some embodiments, the task data may be timestamped according to an interaction or event, such as a recorded button press, or a task being displayed to a subject. The task related timestamp(s) may be additional time stamps to time series time stamps that may be associated with the determined sensor data.

In some embodiments, the control device 110, server 230 or computing device 220 (for example, the cognitive performance monitoring application 225) may be configured to timestamp section(s) or subset(s) of the sensor data with task related timestamp(s). For example, the control device 110 or server 230 may be configured to timestamp the sensor data in response to receiving a timestamp instruction from the cognitive performance monitoring application 225.

In some embodiment, the control device 110 provides or streams sensor data to the computing device 220. As tasks or task related events are occurring, the cognitive performance monitoring application 225 timestamps the sensor data with a respective task or event related timestamp. This may allow the sensor data to be associated with task data occurring at a specific time, such as when a stimulation event or task event occurs, for example, the subject being shown an image on the user interface of the computing device, or the subject performing a specific task or action. This may allow for increased ease of data collection, and/or improved accuracy of analysis of results, as biological data that is time stamped and contextualized to human behaviour tends to be inherently more informative than pure biological data.

The control device 110, computing device 220 or server 230 may be configured to determine a representative response for each channel. For example, the representative response may be indicative of activation during the task as a function of the measured or sensor data associated with performing the task. For example, the response (for example, the hemodynamic response) for a channel may be an average of the measured or sensor data (for example, the blocks of data under task conditions) associated with performing the task as recorded or measured by that channel. Accordingly, a representative response may be determined for each of the plurality of channels considered, which may be the long channels.

In some embodiments, the feature extraction module 322 extracts features or characteristics from the recorded data or measured data. For example, the feature extraction module 322 may extract features or characteristics from the representative responses of one or more channels, as described above, such as HbO amplitude, or area under the curve, for example. The extracted features may correspond to characteristics or biomarkers associated with cognitive function or performance or cortical activity of the user. The extracted features may be provided as input(s) to the symptom severity (or progress) determination model 327, along with the score(s), and the symptom severity or progress determination model 327 may provide as an output, the symptom severity or progress measure. The progress measure may be indicative of the progress the subject is making in treating symptoms of neurological condition.

In some embodiments, the feature extraction module 322 may be configured to determine feature values indicative of or comprising functional connectivity between pairs of optical sensor channels and/or statistical measures of data acquired from optical sensor channels.

In some embodiments, feature values derived from sensor data acquired from optical channels configured to measure activity at the right lateral prefrontal cortex is used by the symptom severity and/or progress determination model 328 to determine an overall ADHD symptom severity measure.

In some embodiments, feature values derived from sensor data acquired from optical channels configured to measure activity at the right lateral prefrontal cortex is used by the symptom severity and/or progress determination model 328 to determine a primary ADHD core symptom score or measure.

In some embodiments, feature values derived from sensor data acquired from optical channels configured to measure activity at the subject's medial prefrontal cortex, and in some cases, at the medial prefrontal cortex toward, overlapping or bordering on the subject's left lateral prefrontal cortex is used by the symptom severity and/or progress determination model 328 to determine an inattention severity measure.

In some embodiments, feature values derived from sensor data acquired from optical channels configured to measure activity at the subject's right lateral prefrontal cortex, the left lateral prefrontal cortex, and/or the region overlapping with the left lateral prefrontal cortex and the medial prefrontal cortex is used by the symptom severity and/or progress determination model 328 to determine a hyperactivity severity measure.

In some embodiments, feature values derived from sensor data acquired from optical channels configured to measure activity at the subject's medial prefrontal cortex, and/or the medial prefrontal cortex toward, overlapping or bordering on the subject's right lateral prefrontal cortex is used by the symptom severity and/or progress determination model 328 to determine an impulsivity severity measure.

At 1025, the control device 110, server 230 or computing device 220 outputs the symptom severity or progress measure. For example, the control device 110 or computing device 220 may output the symptom severity or progress measure by providing the symptom severity or progress measure to the user via the user interface 360, or the control device 110 or server 230 may transmit the symptom severity or progress measure to the cognitive performance monitoring application 225 of the user's computing device 220, or to the clinician's computing device, to server 230 or to database 240, for example.

In some embodiments, steps 1015, 1020 and/or 1025 may be performed by the server 230. In some embodiments, steps 1015, 1020 and/or 1025 may be performed by the computing device 220.

A first study was conducted with a view to determining one or more features that can be extracted from the sensor data that correspond to, or are relatively strong indicators of, characteristics or biomarkers associated with cognitive function or performance or cortical activity of the user in response to applied stimulation.

The study involved 16 participants or subjects. The headset or apparatus 100 (or the array 700 of the apparatus 100) was placed on the forehead of each subject. The apparatus 100 extended between the eyebrows and hairline and from temple to temple. The apparatus 100 was fit with conductive sponges (electrodes 120) to deliver current to the head, and in particular the prefrontal cortex, of the subject. The subject was instructed to lay down with their eyes closed (known as resting state measurement). The control device 110 was used to deliver stimulation from the electrical stimulation generator 350 to the conductive sponges, and accordingly the prefrontal cortex of the subject. In particular, the control device 110 was used to deliver stimulation of varying intensities with breaks of no current in-between each stimulation session. For example, for many of the subjects, eight stimulation and recording sessions were conducted. A first session involved a period of time of no stimulation (for example between 2 and 8 minutes), followed by an application of stimulation at a current of 0.25 mA for an application time period (for example between 2 and 8 minutes). A second session involved a period of time of no stimulation, followed by an application of stimulation at a current of 0.5 mA for an application time period. A third session involved application of stimulation at a current of 0.75 mA for an application time period. A fourth session involved a period of time of no stimulation, followed by an application of stimulation at a current of 1.0 mA for an application time. A fifth session involved a period of time of no stimulation, followed by an application of stimulation at a current of 1.25 mA for an application time period. A sixth session involved a period of time of no stimulation, followed by an application of stimulation at a current of 1.5 mA for an application time period. A seventh session involved a period of time of no stimulation, followed by an application of stimulation at a current of 1.75 mA for an application time period. An eighth session involved a period of time of no stimulation, followed by an application of stimulation at a current of 2.0 mA for an application time period. Sensor data was recorded from the sensors of the apparatus 100 during each session to thereby generate a sensor dataset comprising a set of sensor data for each stimulation current setting from 0.25 mA to 2.0 mA, in steps of 0.25 mA, along with respective application time periods and rest time periods.

A training dataset was generated from the recorded sensor dataset to train a logistic regression model (a sigmoidal model)—the activity determination model 328. The training dataset comprised a first set of examples, each of which corresponded with sensor data recorded during the first stimulation sessions (i.e. stimulation current of 0.25 mA). The first set of examples were labelled as "insufficient", that is, insufficient to elicit a sufficient response from the brain or generate an insufficient activity measure. The training dataset comprised a second set of examples, each of which corresponded with sensors data recorded during the eighth stimulation sessions (i.e. stimulation current of 2.0 mA). The second set of examples were labelled as "sufficient", that is, sufficient to elicit a sufficient response from the brain or generate a sufficient activity measure. The training dataset was used to train the activity determination model 328.

The coefficients of the features were determined by training and testing the activity determination model 328 on 1000 different random samplings of the training set and then averaging the values.

Figure 15:
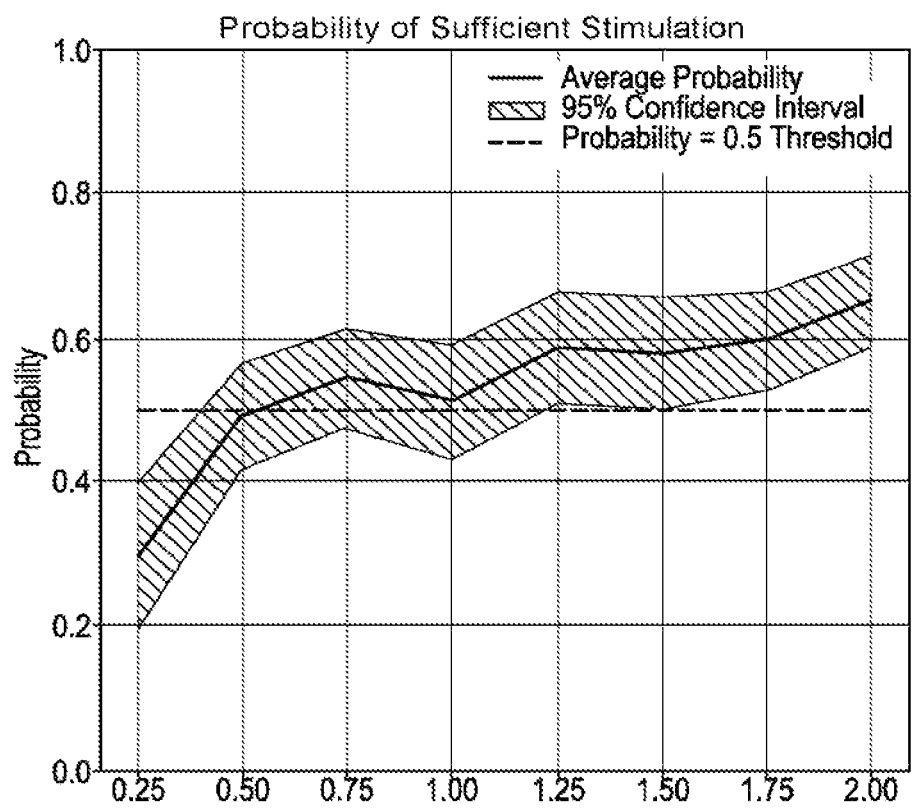
FIG. 15 is an example plot of probability of sufficient stimulation against current (mA)

Once the model was trained, the relevant feature values were extracted from the examples of the remaining sensor data acquired during the second to seventh stimulation sessions to predict a probability of sufficient stimulation being delivered to the respect subject for each of the stimulation currents. The results for the average across all subjects is illustrated in FIG. 15, which is a plot of probability of sufficient stimulation against stimulation current (mA).

The sensor data acquired goes through processing and signal enhancement using standard techniques including short channel removal and accelerometer removal, as discussed above. The sensor data is split into three time blocks: pre, during, and post stimulation. For each time block, the following statistics are calculated for both the Hbr and Hbo data:

For every fNIRS long channel: (i) Mean value (raw_mean) (ii) Standard deviation (raw_std), (iii) Mean value of the derivative (diff_mean) and (iv) Standard deviation of the derivative (diff_std). For every pair of fNIRS long channels: (i) Correlation coefficient (raw_corrcoef) (Note: This is used to determine functional connectivity).

The changes in these statistics between the different time blocks are used to generate features. The three changes used are (i) Before stimulation to during stimulation (before_to_during_change); (ii) Before stimulation to after stimulation (before_to_after_change); and (ii) During stimulation to after stimulation (during_to_after_change.

All of the features for each of the long channels are collected and tested for significant correlation with current of stimulation used. Only features with a correlation with a p-value<0.005 were used in the activity determination model 328.

Features extracted from the sensor data of the examples and used as inputs to the model that were found to be good predictors of activity are shown in Table I, along with the mean value of the weights or coefficients determined by the training of the model. Table I further includes the values for the standard deviation, the t-score, and the coefficient of variance (CoV) of the coefficient value for the feature. The features of Table I are arranged from the most predictive feature, or feature most indicative of the activity level of the subject, to the least predictive feature of that set of features. All of the features with positive coefficient values are positively correlated with the activity measure, and the feature with the negative coefficient value ("S2D6 hbr S3D8 hbr raw corr coeff during to after change") is negatively correlated with correlated with the activity measure. According to the results of Table I, the feature "S3D4 HbR raw std before to after change" is most indicative of whether sufficient stimulation has been applied and a suitable and reliable feature for predicting a probability of whether sufficient stimulation has been applied. The feature "S3D hbo S4D8 hbo raw corr coef before to during change" is a high performing feature indicative of whether sufficient stimulation has been applied to a subject and a suitable and reliable feature for predicting a probability of whether sufficient stimulation has been applied.

Any one, or any combinations of the features of Table I may be used to predict a probability of whether sufficient stimulation has been applied. Such feature(s) may be used to train the activity determination model 328. Once trained, by providing values for those feature(s) extracted from sensor data as inputs to the activity determination model, the activity determination model 328 will an activity measure for the subject.

TABLE I

| | coefficient_mean | coefficient_std | tscore | CoV |
|---|---|---|---|---|
| S3_D4 hbr_raw_std_before_to_after_change | 0.784002 | 0.200759 | 123.493097 | 0.256069 |
| S3_D8 hbo_S4_D8 hbo_raw_corrcoef_before_to_during_change | 0.721617 | 0.116793 | 195.383673 | 0.161850 |
| S4_D8 hbo_S5_D8 hbo_raw_corrcoef_before_to_during_change | 0.560612 | 0.113208 | 156.597854 | 0.201936 |
| S4_D8 hbr_diff_std_during_to_after_change | 0.511265 | 0.112889 | 143.217219 | 0.220803 |
| S4_D6 hbo_diff_std_before_to_after_change | 0.480229 | 0.090511 | 167.783092 | 0.188474 |
| S2_D4 hbo_S3_D4 hbo_diff_corrcoef_before_to_during_change | 0.460770 | 0.136550 | 106.706664 | 0.296352 |

TABLE I-continued

| | coefficient_mean | coefficient_std | tscore | CoV |
|---|---|---|---|---|
| S2_D6 hbr_S3_D6 hbr_diff_corrcoef_beofre_to_during_change | 0.444764 | 0.114132 | 120.075151 | 0.263358 |
| S4_D6 hbr_diff_std_before_to_after_change | 0.388282 | 0.095078 | 129.141378 | 0.244869 |
| S4_D8 hbo_S5_D8 hbr_raw_corrcoef_before_to_during_change | 0.366713 | 0.105675 | 109.736839 | 0.288169 |
| S2_D6 hbr_S3_D8 hbr_raw_corrcoef_during_to_after_change | −0.342503 | 0.163320 | −66.317003 | 0.476843 |
| S2_D4 hbr_S4_D6 hbo_diff_corrcoef_before_to_during_change | 0.327312 | 0.101647 | 101.828010 | 0.310551 |
| S3_D6 hbo_diff_std_before_to_after_change | 0.289173 | 0.123267 | 74.183886 | 0.426276 |
| S3_D8 hbo_S5_D8 hbo_diff_corrcoef_before_to_during_change | 0.284035 | 0.064078 | 140.173335 | 0.225598 |
| S4_D6 hbr_S4_D8 hbr_diff_corrcoef_during_to_after_change | 0.280692 | 0.084771 | 104.708465 | 0.302008 |
| S4_D6 hbo_S4_D8 hbo_diff_corrcoef_before_to_during_change | 0.229936 | 0.067740 | 107.339713 | 0.294605 |
| S4_D8 hbr_diff_std_before_to_after_change | 0.221947 | 0.073822 | 95.074540 | 0.332610 |
| S2_D4 hbo_S3_D8 hbo_diff_corrcoef_before_to_during_change | 0.206023 | 0.091213 | 71.426433 | 0.442732 |
| S3_D6 hbr_diff_std_before_to_after_change | 0.179699 | 0.147208 | 38.602602 | 0.819188 |
| S2_D4 hbo_diff_std_before_to_after_change | 0.165402 | 0.095532 | 54.750828 | 0.577576 |

Table II below provides a description of some of the terminology used for the features of Table 1. Although all of the features from Table I are not included in Table II, it will be appreciated that the description provided as an explanation of the terminology used to define the features can be equally applied to the other features of Table I.

TABLE II

| Feature | Description | Correlation/rank |
|---|---|---|
| S3D4 HbR raw std before to after | The change in standard deviation of deoxygenated blood from before stimulation to after stimulation on the channels around the cathode (negative stim electrode) | Positive correlation with activity measure |
| S4D8 HbO S5D8 HbO raw corr coef before to during or S3D8 HbO S4D8 HbO raw corr coef before to during | The functional connectivity of oxygenated blood within the brain region at the mid point of the anode (pos) and cathode (neg) electrodes. | Positive correlation with activity measure |
| S2D6 HbR S3D8 HbR raw corr coef during to after or S2D4 HbR S3D4 HbR raw corr coef during to after | The functional connectivity change of deoxygenated blood within the brain region around the cathode (neg) electrodes. | Negative correlation with activity measure |
| S3D8 S4D8 HbO diff corr coef before to during | The function connectivity change of oxygenated blood increasing in the area surrounding and underneath the cathode (neg) | Positive correlation with activity measure |
| S4D8 HbR diff std before to after or S4D6 HbR diff std before to after | The change in variation of high frequency fluctuations of deoxygenated blood from before to after stimulation in the regions between the anode (pos) and cathode (neg) | Positive correlation with activity measure |
| S4D8 HbR diff std during to after | The change in variation of high frequency fluctuations of deoxygenated blood from during to after stimulation in the regions between the anode (pos) and cathode (neg) | Positive correlation with activity measure |
| S4D6 HbO diff std before to after | The change in variation of high frequency fluctuations of oxygenated blood from before to after stimulation in the regions between the anode (pos) and cathode (neg) | Positive correlation with activity measure |

With respect to the feature "S3D4 HbR raw std before to after", which is a measure of a change in standard deviation of deoxygenated blood from before the application of stimulation to after the application of stimulation on the channels around the stimulating cathode (negative stimulating electrode), it was found to have a positive correlation with the activity measure. This may be due to an increase in stimulation, causing an increase in the negative current at the cathode. The negative current at the cathode may cause a decrease in activity around the cathode, and therefore an increase in deoxygenated blood activity.

With respect to the features "S4D8 HbO S5D8 HbO raw corr coef before to during" and "S3D8 HbO S4D8 HbO raw corr coef before to during", both of these features are indicative of a functional connectivity of oxygenated blood within the brain region at the mid point of the anode (pos) and cathode (neg) of stimulating electrodes, and were found to have a positive correlation with the activity measure. As current moves from the anode to the cathode, the increase in functional connectivity conveys that increased synchronous activity is occurring at the point between the two electrodes. This is apparent when comparing the functional connectivity before stimulation to during stimulation and is positively correlated with stimulation intensity, showing that the increase in connectivity is likely due to increased activation caused by stimulation.

Table II Referring to FIGS. 7*a* and 7*b*, the locations of the sensor detectors pairs referred to in Tables I and II can be readily understood.

In some embodiments, the feature(s) for the activity determination model 328 are extracted from sensor data acquired from a subject's left lateral prefrontal cortex. For example, the apparatus 100 may be position on the head of the subject such that a first sensor module (comprising sensor S2 and sectors D3 and D4) and a neighbouring second sensor module (comprising sensor S3 and detectors D5 and D6) are positioned to measure or record data from the subject's left lateral prefrontal cortex. For example, sensor data acquired from the subject's left lateral prefrontal cortex may comprise sensor data determined from one or more of: a long channel between a first sensor (S2) and first detector (D4) of the first sensor module, a long channel between a second sensor (S3) and a second detector (D6) of a second neighbouring sensor module, a long channel between the first sensor (S2) of the first sensor module and the second detector (D6) of the second sensor module and a long channel between the second sensor (S3) of the second sensor module and the first detector (D4) of the first sensor module.

In some embodiments, the feature(s) for the activity determination model 328 are extracted from sensor data acquired from a subject's medial prefrontal cortex. For example, the apparatus 100 may be position on the head of the subject such that a third sensor module (comprising sensor S4 and sectors D7 and D8) and a neighbouring fourth sensor module (comprising sensor S5 and detectors D9 and D10) are positioned to measure or record data from the subject's medial prefrontal cortex. For example, sensor data acquired from the subject's medial prefrontal cortex may comprise sensor data determined from one or more of: a long channel between a first sensor (S4) and a first detector (D8) of the third sensor module and a long channel between a second sensor (S5) of the fourth neighbouring sensor module and the first detector (D8) of the third sensor module.

In some embodiments, the feature(s) for the activity determination model 328 are extracted from sensor data acquired from a subject's left lateral prefrontal cortex, the medial prefrontal cortex, and/or a boundary between medial prefrontal and left lateral prefrontal. In some embodiments, the sensor data may be acquired from one or more of: a long channel between the second sensor (S3) of the second sensor module and the first detector (D8) of the third sensor module and a long channel and a long channel between the first sensor (S4) of the third sensor module and the second detector (D6) of the second sensor module. In some embodiments, the sensor data may be acquired from one or more of channels S2D4, S2D6, S3D4, S3D6 and one of more of channels S4D8 and S5D8, and optionally, one or more of S3D8 and S4D6.

A shown in FIG. 7*b*, different regions have some overlap. For example, S4D6 and S3D8 are boundary channels between medial prefrontal and left lateral prefrontal and so can be considered a part of either/both regions. This is true for all places that the circles in FIG. 7*b* cross over.

A second study was conducted with a view to determining one or more features that can be extracted from the sensor data and/or task data that correspond to, or are relatively strong indicators of, characteristics or biomarkers of cognitive function or performance or cortical activity of a subject while the subject is undergoing or undertaking specific tasks.

The study involved 10 participants or subjects with ADHD. The headset or apparatus 100 (or the array 700 of the apparatus 100) was placed on the forehead of each subject between the eyebrows and hairline, and from temple to temple. The headset or apparatus 100 had no conductive sponges and no stimulation was applied. The apparatus 100 was only used to record the brain response, or cortical activity, while the subject was performing a task or test, using the optical sensors 130, which comprised fNIRS sensors in this study.

The subjects each completed an ADHD rating scale questionnaire. The ADHD rating scale questionnaire includes a set of 18 questions that are often given by psychiatrists to aid in a diagnosis of ADHD. Specific questions are designed to assess different symptoms of ADHD and help to identify the type and/or extent of ADHD the person has, being either inattentive type, hyperactive type or combined type. The scale is a self-report scale where the patient can fill out on a scale—from never, to very often— how often they are affected by common symptoms and how severely they are affected by the symptoms. The answers to the questionnaire provided by the subjects were used to assign the subject a set of determined symptom severity or progress scores. For example, each set of determined progress scores included a total or overall ADHD rating scale score, an ADHD core symptom score, an inattention score, a hyperactivity score, and an impulsivity score.

The subjects were asked to perform a first cognitive performance (executive function) task called the "Go-No/Go task", which is a well-known test designed to test a subject's impulse control and attention. The subjects were also asked to perform a second performance (executive function) task called the "N-back task", which is a well-known test designed to test a subject's working memory and attention.

In this study, for each condition of the Go-No/Go and N-back tasks, the following metrics were calculated using recorded button press information:
a. Accuracy–mean value (accuracy_mean)
b. Accuracy–standard deviation (accuracy_std)
c. Reaction time–mean value (reaction_time_mean)
d. Reaction time–standard deviation (reaction_time_std)
e. Omission error–mean value (omission_errors_mean)
f. Omission error–standard deviation (omission_errors_std)
g. Commission error–mean value (commission_errors_mean)
h. Commission error–standard deviation (commission_errors_std)

A set of task scores for each task performed were generated for each subject. For example, the task scores for the first and second performance tasks included values for reaction time, accuracy, omission errors, and commission errors.

For each subject, a first set of sensor data was recorded while the subject undertook the first performance task and a second set of sensor data was recorded while the subject undertook the second performance task.

The sensor data underwent processing and signal enhancement including short channel removal and accelerometer removal, as discussed above.

The sensor data was averaged over all repetitions of each experimental conditions. For Go No/Go the conditions are: (go, gonogo), and for N-Back the conditions are: (0-back, 1-back, 2-back). The sensor data was averaged over each region of interest. In other words, data from particular sensor channels are grouped into regions, as discussed in more detail below. For each region of interest, the following statistics are calculated for both the Hbr and Hbo data:

a. Mean value (raw_mean)
b. Standard deviation (raw_std)
c. Maximum value (raw_max)
d. Minimum value (raw_min)
e. General linear model fitted coefficient (theta)

A training dataset of examples was generated from the sensor data, the sets of task scores, and the determined progress scores (labels). The training dataset was used to train a linear model—the symptom severity (or progress) determination model 327. The symptom severity determination model 327 was configured to receive, as inputs, features from the sensor data acquired while the first performance task was being performed, features from the sensor data acquired while the second performance task was being performed, tasks scores from the first performance task, and tasks scores from second performance task, and provide as an output a progress or a symptom severity measure, or a symptom severity measure for each category of symptoms (for example, overall ADHD score, an ADHD core symptom score, an inattention score, a hyperactivity score, and an impulsivity score).

The symptom severity (or progress) determination model 327 was trained on 75% of the data of the training dataset and tested on the remaining 25%. This was done 1000 times for different sampling of training and test data. All of the features for each of the long channels and task features are collected and tested for significant correlation with symptom severity measure. Only features with the top 10 correlations among all the available features were used in symptom severity (or progress) determination model 327.

Some of the high performing features extracted from the sets of sensor data and/or the sets of task scores of the examples and used as inputs to the model are shown in Tables III to VII below, along with the mean value of the weights or coefficients determined by the training of the model. The tables further include the values for the standard deviation, the t-score, the coefficient of variance (CoV) of the coefficient value, and p-value for the features.

Again with reference to FIGS. 7a and 7b, the regions "left_3", "left_2", "left_1", "mid", "right_1". "right_2", "right_3" mentioned in the Tables below refer to:
left_3=S1D2, S2D2, S1D4
left_2=S2D4, S3D4, S2D6
left_1=S3D6, S4D6, S3D8
mid=S4D8, S4D10, S5D8, S5D10
right_1=S6D10, S5D12, S6D12
right_2=S7D12, S6D14, S7D14
right_3=S8D14, S7D16, S8D16

TABLE III

| | coefficient_mean | coefficient_std | tscore | CoV | pvalue |
|---|---|---|---|---|---|
| 1-back_reaction_time_std | 2.244548 | 1.194139 | 59.439336 | 0.532018 | 0.000000 |
| 1_back_right_2_hbo_raw_mean | −2.101908 | 1.252190 | −53.081523 | 0.595740 | 0.000000 |
| 2-back_omission_errors_std | 1.384634 | 1.028096 | 42.589403 | 0.742503 | 0.000000 |
| gonogo_left_3_hbr_raw_mean | 1.093182 | 0.871831 | 39.651570 | 0.797516 | 0.000000 |
| 1_back_right_2_hbo_raw_min | −0.755032 | 0.499386 | −47.811100 | 0.661411 | 0.000000 |
| gonogo_left_1_hbo_theta | −0.575179 | 0.627704 | −28.976638 | 1.091320 | 0.000000 |
| 2_back_right_3_hbr_raw_mean | 0.508484 | 1.280569 | 12.556668 | 2.518405 | 0.000000 |
| 1_back_left_1_hbo_theta | −0.320053 | 0.607091 | −16.671248 | 1.896845 | 0.000000 |
| gonogo_left_3_hbr_raw_max | 0.255609 | 0.820641 | 9.849689 | 3.210536 | 0.000000 |
| gonogo_right_1_hbo_raw_max | 0.094094 | 0.773660 | 3.846036 | 8.222173 | 0.000128 |

Table III tabulates the top ten features determined to be good predictors of an overall ADHD symptom severity measure, with the first feature ('1-back reaction time std') and third feature, extracted from the task score data, being positively correlated with the symptom severity measure, the forth, seventh, ninth and tenth features (all extracted from the sensor data), being positively correlated with the symptom severity measure, and the four other features, extracted from the sensor data, being negatively correlated with the overall ADHD symptom severity measure. Accordingly, features from both the sensor data and the task data are used as inputs to the trained symptom severity determination model 327 to determine an overall ADHD symptom severity measure for a subject. Of the task data available, the reaction time and omissions metrics have the strongest (positive) correlation with the overall ADHD symptom severity measure. It is notable that of the sensor data available, the channels configured to measure activity at the right lateral prefrontal cortex (S7D12, S6D14, S7D14) have the strongest (negative) correlation with the overall ADHD symptom severity measure.

TABLE IV

|  | coefficient_mean | coefficient_std | tscore | CoV | pvalue |
| --- | --- | --- | --- | --- | --- |
| 1_back_right_2_hbo_raw_mean | −0.956945 | 0.533121 | −56.762457 | 0.557107 | 0.000000 |
| 1_back_mid_hbr_theta | 0.871165 | 0.606536 | 45.419661 | 0.696235 | 0.000000 |
| gonogo_left_2_hbr_raw_std | −0.834898 | 0.592958 | −44.525558 | 0.710216 | 0.000000 |
| 1_back_left_1_hbo_raw_mean | −0.653260 | 0.836472 | −24.696471 | 1.280457 | 0.000000 |
| 1_back_mid_hbo_theta | 0.631417 | 0.926957 | 21.540536 | 1.468059 | 0.000000 |
| gonogo_mid_hbo_theta | 0.613029 | 0.750131 | 25.843078 | 1.223646 | 0.000000 |
| gonogo_left_2_hbr_raw_mean | −0.486064 | 0.442470 | −34.738397 | 0.910312 | 0.000000 |
| gonogo_left_2_hbr_raw_max | −0.455532 | 0.295332 | −48.776214 | 0.648324 | 0.000000 |
| gonogo_right_1_hbo_raw_max | 0.338631 | 0.688645 | 15.550049 | 2.033613 | 0.000000 |
| 1_back_right_2_hbo_raw_min | 0.150772 | 0.494621 | 9.639376 | 3.280583 | 0.000000 |

Table IV tabulates the top ten features determined to be good predictors of a primary ADHD core symptom score, with the first, third, fourth, seventh and eighth features, extracted from the sensor data, being negatively correlated with the primary ADHD core symptom score, and the other features, extracted from the sensor data, being positively correlated with the primary ADHD core symptom score. Accordingly, only features from the sensor data are used as inputs to the trained symptom severity determination model 327 to determine a primary ADHD core symptom score for a subject. It is notable that of the sensor data available, the channels configured to measure activity at the right lateral prefrontal cortex (S7D12, S6D14, S7D14) have the strongest (negative) correlation with the primary ADHD core symptom score.

TABLE V

|  | coefficient_mean | coefficient_std | tscore | CoV | pvalue |
| --- | --- | --- | --- | --- | --- |
| 2_back_right_1_hbo_theta | 0.768204 | 0.371564 | 65.379610 | 0.483679 | 0.000000 |
| 1-back_reaction_time_std | 0.551849 | 0.353224 | 49.404889 | 0.640074 | 0.000000 |
| gonogo_left_3_hbr_raw_max | 0.541322 | 0.309392 | 55.328190 | 0.571549 | 0.000000 |
| gonogo_left_1_hbr_raw_max | −0.348583 | 0.302418 | −36.450096 | 0.867564 | 0.000000 |
| 1-back_omission_errors_mean | 0.253324 | 0.170113 | 47.091058 | 0.671524 | 0.000000 |
| 2_back_mid_hbr_theta | −0.149754 | 0.235921 | −20.072959 | 1.575392 | 0.000000 |
| 2_back_left_1_hbo_theta | 0.100341 | 0.231974 | 13.678608 | 2.311842 | 0.000000 |
| gonogo_left_3_hbr_raw_mean | 0.081239 | 0.293446 | 8.754623 | 3.612123 | 0.000000 |
| 2_back_right_1_hbo_raw_mean | −0.035858 | 0.208646 | −5.434784 | 5.818590 | 0.000000 |
| 1-back_omission_errors_std | 0.035267 | 0.273057 | 4.084234 | 7.742646 | 0.000048 |

Table V tabulates the top ten features determined to be good predictors of the symptom of inattention, with the first, third, seventh and eight features (all extracted from the sensor data), second, fifth and tenth features (extracted from the task score data) being positively correlated with the symptom of inattention, and the other features, all extracted from the sensor data, being negatively correlated with the symptom of inattention. Accordingly, features from both the sensor data and the task data are used as inputs to the trained symptom severity determination model 327 to determine an inattention severity measure for a subject. Of the task data available, the reaction time and omission errors metrics have the strongest (positive) correlation with the symptom of inattention. It is notable that of the sensor data available, the channels configured to measure activity at the subject's medial prefrontal cortex, and in some cases, at the medial prefrontal cortex toward, overlapping or bordering on the subject's right lateral prefrontal cortex (S6D10, S5D12, S6D12) have the strongest correlation with the symptom of inattention.

TABLE VI

|  | coefficient_mean | coefficient_std | tscore | CoV | pvalue |
| --- | --- | --- | --- | --- | --- |
| 1_back_right_2_hbo_raw_mean | −1.188398 | 0.309523 | −121.413931 | 0.260454 | 0.000000 |
| gonogo_left_1_hbo_theta | −0.937263 | 0.501494 | −59.101111 | 0.535062 | 0.000000 |
| 1_back_left_1_hbo_raw_min | 0.561317 | 0.450860 | 39.370139 | 0.803217 | 0.000000 |
| 1_back_left_2_hbo_theta | −0.448590 | 0.294416 | −48.182383 | 0.656314 | 0.000000 |
| 1_back_right_2_hbo_raw_min | −0.277226 | 0.218123 | −40.191331 | 0.786806 | 0.000000 |
| gonogo_mid_hbo_theta | −0.185172 | 0.519825 | −11.264635 | 2.807261 | 0.000000 |
| gonogo_right_1_hbo_raw_max | 0.175440 | 0.420896 | 13.181156 | 2.399090 | 0.000000 |
| 2_back_left_2_hbr_raw_max | −0.145495 | 0.177432 | −25.930891 | 1.219502 | 0.000000 |
| 2_back_left_2_hbr_raw_mean | 0.102297 | 0.320478 | 10.093974 | 3.132837 | 0.000000 |
| 1_back_left_1_hbo_theta | −0.059325 | 0.289072 | −6.489749 | 4.872727 | 0.000000 |

Table VI tabulates the top ten features determined to be good predictors of the symptom of hyperactivity, with the first, second, fourth, fifth, sixth, eighth and tenth features (all extracted from the sensor data), being negatively correlated with the symptom of hyperactivity, and the other features, also all extracted from the sensor data, being positively correlated with the hyperactivity. Accordingly, features from the sensor data only are used as inputs to the trained symptom severity determination model 327 to determine a hyperactivity severity measure for a subject. It is notable that of the sensor data available, the channels configured to measure activity at the right lateral prefrontal cortex (S7D12, S6D14, S7D14) and at the left lateral prefrontal cortex, and/or the region overlapping with the left lateral prefrontal cortex and the medial prefrontal cortex (S2D4, S3D4, S2D6) have the strongest (negative) correlation with the hyperactivity severity measure.

TABLE VII

|  | coefficient_mean | coefficient_std | tscore | CoV | pvalue |
| --- | --- | --- | --- | --- | --- |
| 2-back_reaction_time_std | 1.475761 | 0.457687 | 101.964176 | 0.310136 | 0.000000 |
| 1_back_right_1_hbo_raw_mean | 1.071202 | 0.457760 | 74.000324 | 0.427333 | 0.000000 |
| 2_back_right_3_hbo_raw_max | −0.841258 | 0.370674 | −71.769004 | 0.440619 | 0.000000 |
| 2_back_left_3_hbr_raw_mean | 0.654955 | 0.227334 | 91.105948 | 0.347099 | 0.000000 |
| 2_back_right_3_hbr_raw_mean | 0.592720 | 0.296899 | 63.130766 | 0.500909 | 0.000000 |
| gonogo_left_3_hbr_raw_mean | 0.474359 | 0.338177 | 44.357130 | 0.712913 | 0.000000 |
| 2_back_left_3_hbr_raw_max | 0.254784 | 0.195714 | 41.167227 | 0.768154 | 0.000000 |
| 1_back_left_1_hbo_theta | 0.153493 | 0.352429 | 13.772648 | 2.296056 | 0.000000 |
| 2_back_right_3_hbr_theta | 0.100848 | 0.345465 | 9.231256 | 3.425620 | 0.000000 |
| 1_back_right_2_hbo_raw_mean | −0.088005 | 0.332657 | −8.365900 | 3.779961 | 0.000000 |

Table VII tabulates the top ten features determined to be good predictors of the symptom of impulsivity, with the first feature (extracted from the task score data), second, fourth, fifth, sixth, eighth and ninth features (all extracted from the sensor data), being positively correlated with the symptom of impulsivity, and the other features, also all extracted from the sensor data, being positively correlated with the impulsivity. Accordingly, features from both the sensor data and the task data are used as inputs to the trained symptom severity determination model 327 to determine an impulsivity severity measure for a subject. Of the task data available, the reaction time has the strongest (positive) correlation with the symptom of impulsivity. It is notable that of the sensor data available, the channels configured to measure activity at the subject's medial prefrontal cortex, and in some cases, at the medial prefrontal cortex toward, overlapping or bordering on the subject's right lateral prefrontal cortex (S6D10, S5D12, S6D12) have the strongest correlation with the symptom of impulsivity.

Table VIII below provides a description of some of the terminology used for the features of Tables III to VII. Although all of the features from Tables III to VII are not included in Table VIII, it will be appreciated that the description provided as an explanation of the terminology used to define the features can be equally applied to the other features of those tables.

TABLE VIII

| Feature | Description | Correlation |
| --- | --- | --- |
| 1. N-back right 2 HbO raw mean | The change in the average concentration of oxygenated blood in the right prefrontal cortex during the n back task | Negative correlation with progress/symptom severity measure |
| 1. N-back right 1 HbO theta | The coefficient as output by a general linear model estimating the amplitude of the hemodynamic response of the oxygenated blood in the right lateral/medial prefrontal cortex to the n back task | Positive correlation with progress/symptom severity measure |
| 2. N-back reaction time std | The variability in reaction time of responses to the n back task | Positive correlation with progress/symptom severity measure |
| 3. N-back omission error std | The variability in omission errors when performing the n back task | Positive correlation with progress/symptom severity measure |
| 4. Go/no-go left 2 HbR raw std | The variability in concentration of deoxygenated blood in the left prefrontal cortex during the go no go task | Negative correlation with progress/symptom severity measure |
| 2. Go/no-go right 1 HbO raw max | The maximum concentration of oxygenated blood in the right lateral/medial prefrontal cortex during the go no go task | Positive correlation with progress/symptom severity measure |
| 4. Go/no-go reaction time std | The variability in reaction time of responses made during the go no go task | Positive correlation with progress/symptom severity measure |
| 1. N-back right 1 HbO raw mean | The change in the average concentration of oxygenated blood in the right lateral/medial prefrontal cortex during the n back task | Positive correlation with progress/symptom severity measure |

Figure 16A:
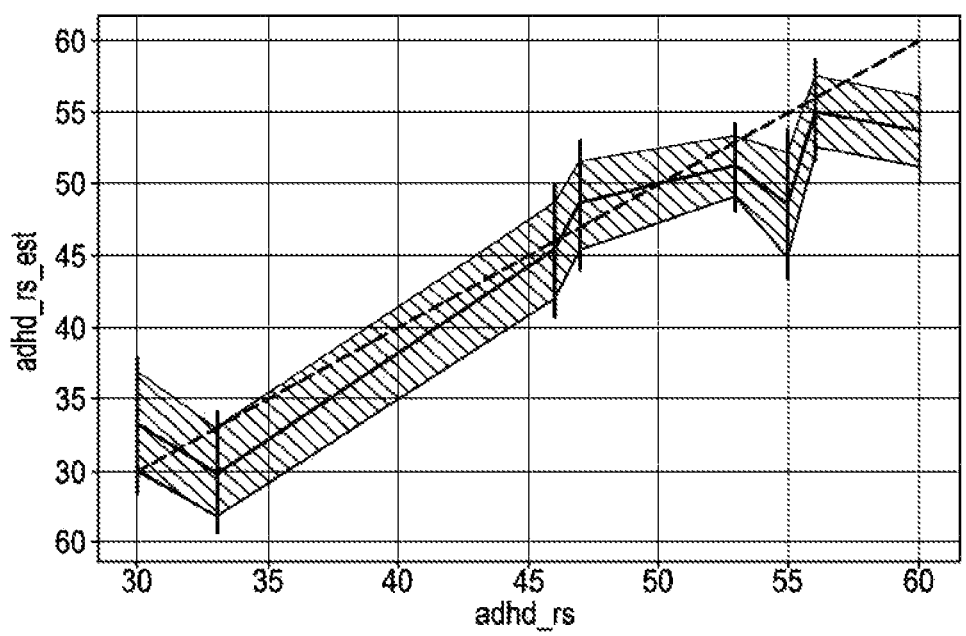
FIGS. 16a to 16c are example plots of actual symptom severity measures/scores (as per ADHD rating scale questionnaire scores) against predicted symptom severity measures/scores (as predicted by the symptom severity determination model 327) for each of the categories of overall ADHD score (FIG. 16a), primary ADHD diagnosis score (FIG. 16b), inattention (FIG. 16c), hyperactivity (FIG. 16a), impulsivity (FIG. 16e)
Figure 16B:
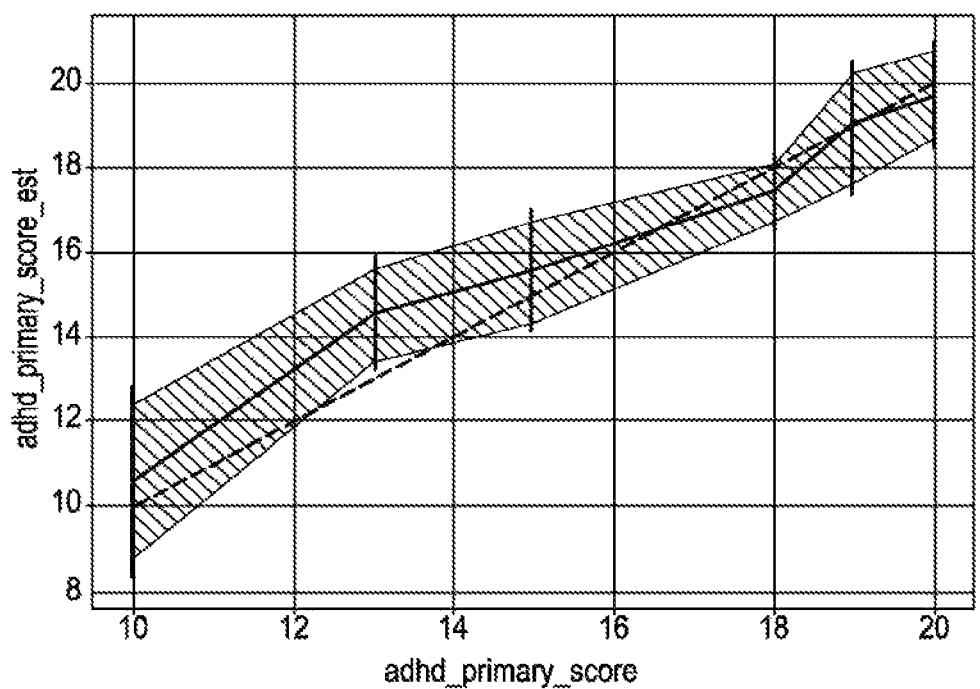
Figure 16C:
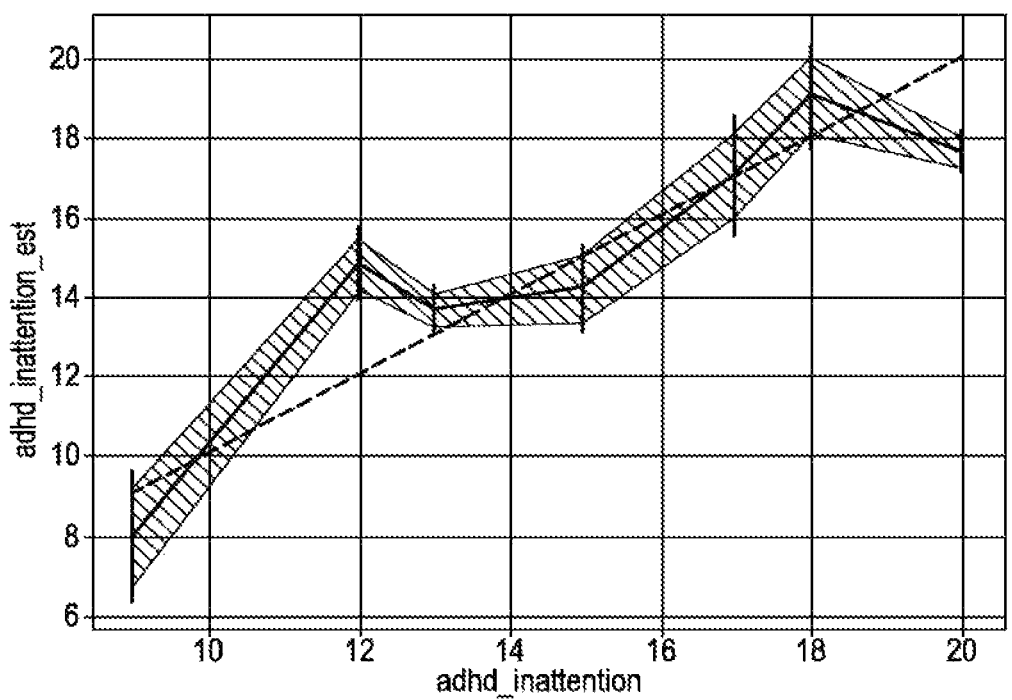
Figure 16D:
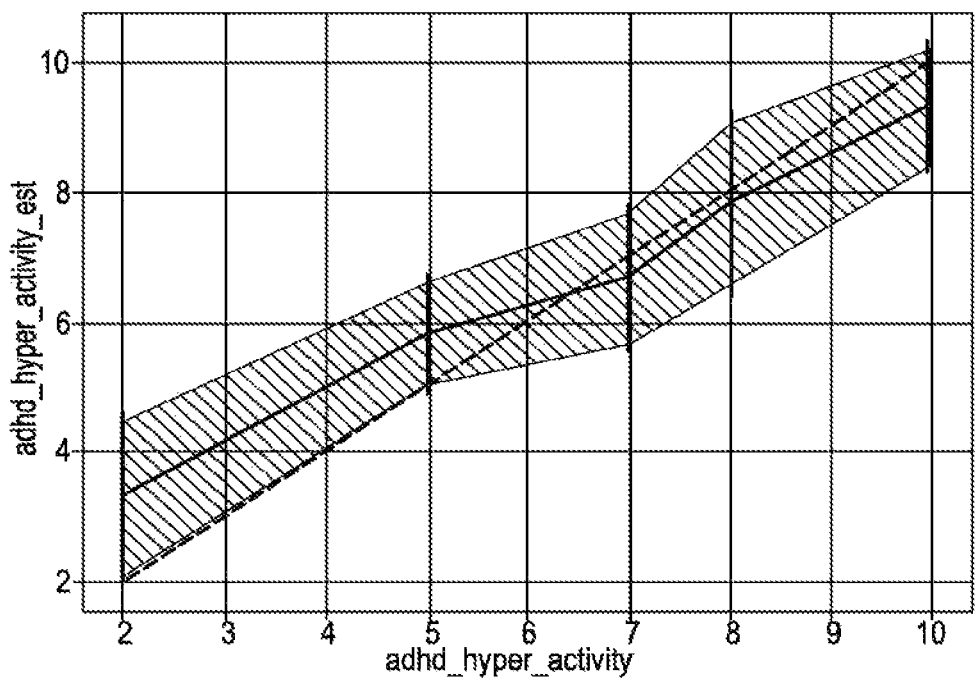
Figure 16E:
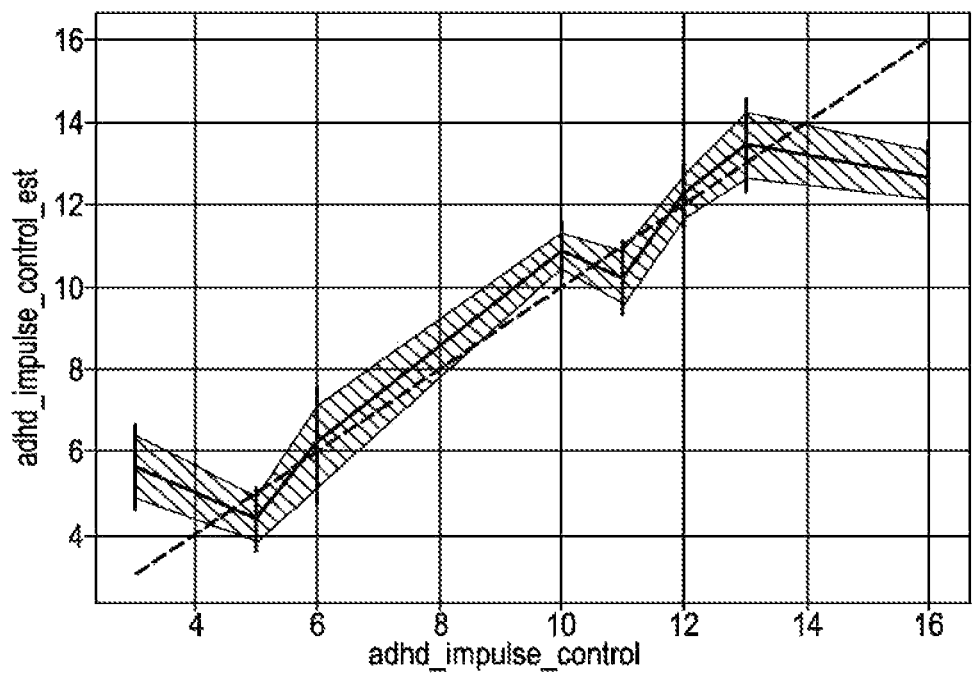

Referring to FIGS. 16*a* to 16*e*, there are shown plots of actual symptom severity measures/scores (as per ADHD rating scale questionnaire scores) against predicted symptom severity measures/scores (as predicted by the symptom severity determination model 327) for each of the categories of overall ADHD score (FIG. 16*a*), primary ADHD core symptom score (FIG. 16*b*), inattention (FIG. 16*c*), hyperactivity (FIG. 16*d*), impulsivity (FIG. 16*e*).

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A system, comprising:
   a headset configured to be worn on a forehead of a user, the headset comprising:
      a first optical sensor configured to be located on a first side of an area of interest of the user's head, the first optical sensor including a first light emitter and at least two light detectors, and
      a second optical sensor configured to be located on a second side of the area of interest of the user's head opposite the first side, the second optical sensor including a second light emitter and at least two light detectors,
      the first optical sensor and the second optical sensor configured to (a) detect a first signal indicative of a brain blood oxygenation of the user, and (b) detect a second signal indicative of a scalp blood oxygenation of the user; and
   a controller communicatively coupled to the first optical sensor and the second optical sensor, the controller configured to:
      receive the first signal and the second signal and determine the brain blood oxygenation level of the user based on the first signal, and the scalp blood oxygenation level of the user based on the second signal.

2. The apparatus of claim 1, wherein the controller is further configured to:
   generate a signal indicative of at least one of the brain blood oxygenation level and the scalp blood oxygenation level.

3. The apparatus of claim 1, wherein when the headset is worn on the forehead of the user:
   the first light emitter is disposed proximate to a first transverse end of the area of interest, a first light detector of the first optical sensor is disposed proximate to the first transverse end and inward of the first light emitter, and a second light detector of the first optical sensor is disposed proximate to a second transverse end of the area of interest, the second transverse end opposite the first transverse end.

4. The apparatus of claim 3, wherein when the headset is worn on the forehead of the user:
the second light emitter is disposed proximate to the second transverse end of the area of interest, a first light detector of the second optical sensor is disposed proximate to the second transverse end and inward of the second light emitter, and a second light detector of the second optical sensor is disposed proximate to the first transverse end of the area of interest.

5. The system of claim 3, wherein the second light detector of the first optical sensor is disposed closer to the first light detector of the first optical sensor than to the first light emitter, and the second light detector of the second optical sensor is disposed closer to the first light detector of the second optical sensor than to the second light emitter.

6. The apparatus of claim 1, wherein the headset further comprises:
an electrode disposed on the headset, the electrode configured to be disposed over the area of interest of the user's head when the headset is worn by the user.

7. The system of claim 6, wherein the controller is further configured to:
cause the electrode to stimulate the area of interest of the user's head based on at least one of the brain blood oxygenation level and the scalp blood oxygenation level.

8. The system of claim 1, wherein the area of interest of the user's head corresponds to at least one of the user's left lateral prefrontal cortex, medial prefrontal cortex, or a boundary region between the user's medial prefrontal and left lateral prefrontal irrespective of the head size of the user.

9. A system, comprising:
a memory;
a processor operatively coupled to the memory and configured to:
receive a first signal from a first optical sensor and a second signal from a second optical sensor, the first optical sensor and the second optical sensor associated with a headset configured to be worn on a forehead of a user;
determine a brain blood oxygenation level of the user based on the first signal, and a scalp blood oxygenation level of the user based on the second signal;
determine task data comprising one or more scores associated with a user's performance in undertaking one or more respective tasks;
subtract the scalp blood oxygenation level from the brain blood oxygenation level to obtain an activity data;
determine at least one of a symptom severity or a progress measure based on at least one of the activity data and the task data; and
generate a signal indicative of the at least one of the symptom severity or the progress measure.

10. The system of claim 9, wherein the processor is further configured to:
determine an activity measure based on one or more features extracted from the activity data, the activity measure corresponding to a level of neural activity in the area of interest of the user's head.

11. The system of 10, wherein:
the headset includes a plurality of electrodes; and
the processor is configured to transmit signals to a plurality of electrodes, the processor further configured to:
determine one or more updated stimulation parameter values; and
generate a signal for stimulating at least one or more of the plurality of electrodes based on the activity measure.

12. The system of claim 11, wherein the stimulation parameter includes at least one of a voltage, a current, a frequency, a duration, or an offset of the transcranial stimulation delivered.

13. The system of claim 9, wherein the symptom severity measure is based on at least one of the task data or one or more features extracted from the activity data, the symptom severity measure and/or progress measure corresponding to at least one clinically relevant symptom.

14. The system of 13, wherein the one or more features extracted from the activity data includes functional connectivity between the first and second optical sensors.

15. The system of claim 9, wherein the symptom severity measure is based on the activity data corresponding to at least one of the right lateral prefrontal cortex, the left lateral prefrontal cortex, the medial prefrontal cortex, a boundary region between the user's medial prefrontal cortex and left lateral prefrontal cortex, or a boundary region between the user's medial prefrontal cortex and right lateral prefrontal cortex.

16. A system, comprising:
a headset configured to be worn on a forehead of a user, the headset comprising:
a first optical sensor including a light emitter and a light detector;
a second optical sensor including a light emitter and a light detector, the first optical sensor and the second optical sensor configured to detect at least one of a first signal and a second signal different from the first signal; and
a controller communicatively coupled to the first optical sensor and the second optical sensor, the controller configured to:
receive the first signal and the second signal and determine a first parameter corresponding to the user's brain based on the first signal, and a second parameter corresponding to the user's brain based on the second signal, the second parameter different from the first parameter, and
cause light emitters of each of the first optical sensor and the second optical sensor to modulate at a flashing frequency to create a lock-in-amplifier effect to improve the signal to noise ratio (SNR) of at least one of the first signal and the second signal.

17. The system of claim 16, wherein the light detector of each of the first optical sensor and the second optical sensor is a first light detector, the first optical sensor and the second optical sensor each including a second light detector.

18. The system of claim 17, wherein for each of the first and second optical sensors, a distance between the light emitter and the first light detector is larger than distance between light emitter and the second light detector.

19. The system of claim 17, wherein when the headset is worn on the forehead of the user, the first optical sensor is configured to be located on a first side of an area of interest of the user's head, and the second optical sensor configured to be located on a second side of the area of interest of the user's head opposite the first side.

20. The system of claim 16, wherein the first signal corresponds to a brain oxygenation level and the second signal corresponds to a scalp blood oxygenation level.

21. The system of claim 16, wherein the first optical sensor and the second optical sensor are configured to measure two distinct wavelengths of light.

22. The system of claim 16, further comprising:
an electrode disposed on the headset and communicatively coupled to the controller, the electrode configured to be disposed over the area of interest of the user's head and selectively provide stimulation to the area of interest.

23. A system, comprising:
a headset configured to be worn on a forehead of a user, the headset comprising:
an optical sensor configured to be positioned proximate to an area of interest of a user's head, the optical sensor including a light emitter, a first light detector, and a second light detector,
the first light detector configured to measure an intensity of light reflected from the user's brain, and the second light detector configured to measure an intensity of light reflected from the user's scalp; and
a controller communicatively coupled to the optical sensor, the controller configured to:
receive a first signal indicative of the intensity of light reflected from the user's brain, and a second signal indicative of the intensity of light reflected from the user's scalp,
determine a brain blood oxygenation level based on the first signal and a scalp blood oxygenation level based on the second signal, and
subtract the scalp blood oxygenation level from the brain blood oxygenation level to obtain an activity data associated with the area of interest of the user's brain.

24. The system of claim 23, wherein the controller is further configured to:
generate a signal indicative of the activity data.

25. The system of claim 23, wherein the controller is further configured to:
determine an activity measure based on one or more features extracted from the activity data, the activity measure corresponding to a level of neural activity in the area of interest of the user's head.

26. The system of 23, wherein the controller is further configured to:
determine at least one of a symptom severity measure and progress measure, the symptom severity measure and/or progress measure corresponding to at least one clinically relevant symptom based on the activity data.

27. The system of claim 26, wherein the controller is further configured to:
determine task data including one or more scores associated with a user's performance in undertaking one or more respective tasks, the symptom severity measure being based on at least one of the task data and the activity data.

28. The system of claim 23, wherein the headset further comprises:
an electrode disposed on the headset and communicatively coupled to the controller, the electrode configured to be disposed over the area of interest of the user's head and provide stimulation to the area of interest.

29. The system of claim 28, wherein the controller is further configured to:
generate a signal indicative of at least one of the brain blood oxygenation level, the scalp blood oxygenation level, or the activity data; and
cause the electrode to stimulate the area of interest of the user's brain based on the signal indicative of at least one of the brain blood oxygenation level, the scalp blood oxygenation level, or the activity data.

30. The system of claim 23, wherein the area of interest of the user's head corresponds to at least one of the user's left lateral prefrontal cortex, medial prefrontal cortex, or a boundary region between the user's medial prefrontal and left lateral prefrontal irrespective of the head size of the user.

* * * * *